US010913965B2

(12) United States Patent
Lawrence et al.

(10) Patent No.: US 10,913,965 B2
(45) Date of Patent: Feb. 9, 2021

(54) MICROBIAL PRODUCTION OF NICOTAMIDE RIBOSIDE

(71) Applicants: DSM IP ASSETS B.V., Heerlen (NL); Adam G. Lawrence, Arlington, MA (US); Celine ViArouge, Kaiseraugst (CH)

(72) Inventors: Adam G. Lawrence, Arlington, MA (US); Celine ViArouge, Kaiseraugst (CH)

(73) Assignee: DSM IP ASSETS B.V., Heerlen (NL)

(*) Notice: Subject to any disclaimer, the term of this patent is extended or adjusted under 35 U.S.C. 154(b) by 0 days.

(21) Appl. No.: 15/774,721

(22) PCT Filed: Nov. 14, 2016

(86) PCT No.: PCT/US2016/061905
§ 371 (c)(1),
(2) Date: May 9, 2018

(87) PCT Pub. No.: WO2017/083858
PCT Pub. Date: May 18, 2017

(65) Prior Publication Data
US 2018/0327797 A1 Nov. 15, 2018

Related U.S. Application Data

(60) Provisional application No. 62/254,736, filed on Nov. 13, 2015.

(51) Int. Cl.
*C12P 19/38* (2006.01)
*C12N 9/00* (2006.01)
*C12N 9/14* (2006.01)
*A23L 33/15* (2016.01)

(52) U.S. Cl.
CPC ............... *C12P 19/38* (2013.01); *A23L 33/15* (2016.08); *C12N 9/14* (2013.01); *C12N 9/93* (2013.01); *C12Y 306/01022* (2013.01); *C12Y 603/01005* (2013.01); *A23V 2002/00* (2013.01)

(58) Field of Classification Search
None
See application file for complete search history.

(56) References Cited

U.S. PATENT DOCUMENTS

2009/0202680 A1 8/2009 Brenner et al.
2016/0287621 A1* 10/2016 Sinclair ................ A61K 31/455
2018/0327797 A1* 11/2018 Lawrence ...... C12Y 603/01005

OTHER PUBLICATIONS

GenBank Accession No. ACT31020.1, published Dec. 24, 2013 (Year: 2013).*
International Search Report for PCT/US2016/061905 dated May 22, 2017, 6 pages.
Written Opinion of the ISA for PCT/US2016/061905 dated May 22, 2017, 7 pages.

(Continued)

*Primary Examiner* — Richard C Ekstrom
(74) *Attorney, Agent, or Firm* — Nixon & Vanderhye, PC

(57) ABSTRACT

The present disclosure relates to a novel method, expression vectors, and host cells for producing nicotinamide riboside by regulating the pathways that lead to the production of nicotinamide riboside.

3 Claims, 8 Drawing Sheets

Specification includes a Sequence Listing.

(56) References Cited

OTHER PUBLICATIONS

Sorci et al., "Nicotinamide mononucleotide synthetase is the key enzyme for an alternative route of NAD biosynthesis in Francisella tularensis", Proc Nat Acad Sci, Mar. 3, 2009, vol. 9, pp. 3083-3088.
Unknown, UniProt Accession Q5NFH5. NH(3)-dependent NAD(+) synthetase [online], Sep. 16, 2015 (retrieved Feb. 10, 2017).

* cited by examiner quinolate phosphoribosyl pyrophosphate (PRPP)

nictotinic acid mononucleotide (NaMN)

adenine triphosphate (ATP)

nictotinic acid adenine dinucleotide (NaAD)

nictotinamide adenine dinucleotide (NAD)

nictotinic acid mononucleotide (NaMN)

nictotinamide adenine dinucleotide (NAD)

nicotinamide mononucleotide (NMN)

nicotinamide riboside (NR)

phosphoribose nicotinamide riboside (NR)

nicotinic acid (NA)

nicotinamide (Nam)

nicotinic acid mononucleotide (NaMN)

nicotinamide mononucleotide (NMN)

```
                1          10         20         30         40         50         60
                |          |          |          |          |          |          |
 SEQ ID NO: 1   MKIVKDFSPKEYSQKLVNWLSDSCMN-YPAEGFVIGLSGGIDSAVAASLAVKTGLPTTAL
 SEQ ID NO:15   MKIVKDFSPKEYSQKLVNWLSDSCMN-YPAEGFVIGLSGGIDSAVAASLAVKTGLPTTAL
SEQ ID NO: 14   MKIVKDFSPKEYSQKLVNWLSDSCMN-YPAEGFVIGLSGGIDSAVAASLAVKTGLPTTAL
SEQ ID NO: 12   MKIVKDFSPKEYSQKLVNWLSDSCMN-YPAEGFVIGLSGGIDSAVAASLAVKTGLPTTAL
SEQ ID NO: 13   MKIVKDFSPKEYSQKLVNWLSDSCMN-YPAEGFVIGLSGGIDSAVAASLAVKTGLPITAL
SEQ ID NO: 11   MKIVKDFSPKEYSQNLVNWLSDTCIN-YPAEGFVIGISGGIDSAVAASLAVKTGLPTTAL
SEQ ID NO: 10   MKIVKDFNIKEYSQKLIDWLSDTCMN-YPAEGFVIGLSGGIDSAVAASLAVKTGLSTTAL
 SEQ ID NO: 6   MKIIKNFIAEEYSKKLIEWLKKICIN-YPAEGFVIGISGGIDSAVAASLAVKTGLPTTAL
 SEQ ID NO: 7   MKIIKNFIAEEYSKKLIEWLKKICIN-YPAEGFVIGISGGIDSAVAASLAVKTGLPTTAL
 SEQ ID NO: 8   MKIIKNFIAKEYSKKLIEWLKKICIN-YPAEGFVIGISGGIDSAVAASLAVKTGLPTTAL
 SEQ ID NO: 9   MKIIKNFIVEKYSKKLIEWLKKICIN-YPAEGFVIGISGGIDSAVAASLAVKTGLPTTAL
 SEQ ID NO: 5   MKIVKNFIVEQYSNNLIKWLKENCIK-YPAEGFVIGISGGIDSAVAASLAVKTGLPTTAL
 SEQ ID NO: 4   MNVVKNFTPEKYSEKLIQWLTNSCIK-YPAEGFVIGVSGGIDSAVCASLLSKTDLPTTAF
 SEQ ID NO: 3   MSVVKNFKPNEYANKITEWLKDSCLN-YPAEGFVVGISGGIDSAVAVSLAVNTGLPVTGL
SEQ ID NO: 17   ----KRMKTAAYADYLIQWLENQRTELYGMDGYTLGVSGGIDSAVCAHLAARTGAPVQAL
SEQ ID NO: 18   -----------YVDYLVRWLETQRTELYGMDGYTLGVSGGIDSAVCAHLAARTGAPVQAL
 SEQ ID NO:16   -----------QYIDYLLVWLEEQRAHLYASDGYTLGVSGGIDSAVCLHLLAKTGKPVQAL

 SEQ ID NO: 1   ILPSDNNQHQDMQDALELIEMLNIEHYTISIQPAYEAFLASTQSFTNLQNNRQLVIKGNA
 SEQ ID NO:15   ILPSDNNQHQDMQDALELIEMLNIEHYTISIQPAYEAFLASTQSFTNLQNNRQLVIKGNA
SEQ ID NO: 14   ILPSDNNQHQDMQDALELIEMLNIEHYTISIQLAYEAFLASTQSFTNLQNNRQLVIKGNA
SEQ ID NO: 12   ILPSDNNQHQDMQDALDLIEMLNIEHYTISIQPAYEAFLASTQRFTNLQNNRQLVIKGNA
SEQ ID NO: 13   ILPSDNNQHQDMQDALDLIEMLNIEHYTISIQPAYEAFLASTQSFTNLQNNRQLVIKGNA
SEQ ID NO: 11   ILPSKNNQHQDIQDALELVEKLNIEHHIVTIQPAYENFLASTQEFINTDNNRQLVIKGNA
SEQ ID NO: 10   ILPSKNNQHQDIQDALELADKINIEHHTITIQTVYETFLASIKKITNTERDRQLVIKGNA
 SEQ ID NO: 6   ILPSKNNQDQDMKDGLELIKNLDIEHHIVPIQPAYDTFIESTLNFTNSQNDRQHVIKGNA
 SEQ ID NO: 7   ILPSKNNQDQDMKDGLELIKNLDIEHHIVPIQPAYDTFIESTLNFTNSQNDRQHVIKGNA
 SEQ ID NO: 8   ILPSKNNQDQDMKDGLELIKNLDIEHHIVPIQPAYDTFIESTFNFTNAQNNRQHVIKGNA
 SEQ ID NO: 9   ILPSKNNQDQDMKDGLELIKNLDIEHHIVPIQPAYDTFIESTFNFTNAQNNRQHVIKGNA
 SEQ ID NO: 5   ILPSKNNQDQDMRDGIELIENLNIEYHTVSIQPAYDTFIESTFNFTNSQNDRQHVIKGNA
 SEQ ID NO: 4   ILPSKNNSDQDMIDALELINKLNIPYHIIPIQPVYESFLKSTQLFTNPQNDRQNVIKGNA
 SEQ ID NO: 3   IMPSKNNDDKDTLDAIELAKKLNIEYHLIPIQPVYETFLDSAEDIKNSANDRQHVIKGNA
SEQ ID NO: 17   ILPAEVTSPSDVADAQATLESAGIDGQIISIAPWYDLIMQQLSPVLNSEPERVNVLKGNL
SEQ ID NO: 18   ILPAEVTSPEDVADAQITLESAGIDGRIISIAPWYDLIMLQLTPALNAESERINVLKGNL
 SEQ ID NO:16   VLPINAN-ANDCEDAELVLKNANISGNIIALDDVYTAAQNTLAPVLNRDYERMPVLNGNL

 SEQ ID NO: 1   QARLRMMYLYAYAQQYNRIVIGTDNACEWYMGYFTKFGDGAADILPLVNLKKSQVFELGK
 SEQ ID NO:15   QTRLRMMYLYAYAQQYNRIVIGTDNACEWYMGYFTKFGDGAADILPLVNLKKSQVFELGK
SEQ ID NO: 14   QARLRMMYLYAYAQQYNRIVIGTDNACEWYMGYFTKFGDGAADILPLVNLKKSQVFELGK
SEQ ID NO: 12   QARLRMMYLYAYAQQYNRIVIGTDNACEWYMGYFTKFGDGAADILPLVNLKKSQVFELGK
SEQ ID NO: 13   QARLRMMYLYAYAQQYNRIVIGTDNACEWYMGYFTKFGDGAADILPLVNLKKSQVFELGK
SEQ ID NO: 11   QARLRMMYLYAYAQQYNRIVIGTDNACEWYMGYFTKFGDGAADIFPLINLKKSQVFELGK
SEQ ID NO: 10   QARLRMMYLYAYAQQYNRVVIGTDNACEWYMGYFTKFGDGAADILPLVNLKKSHVFELGK
 SEQ ID NO: 6   QARLRMMYLYAYAQQNNRIVIGTDNACEWYMGYFTKFGDGAADILPLVNLKKSQVFEMGK
 SEQ ID NO: 7   QARLRMMYLYAYAQQNNRIVIGTDNACEWYMGYFTKFGDGAADILPLVNLKKSQVFEMGE
 SEQ ID NO: 8   QARLRMMYLYAYAQQNNRIVIGTDNACEWYMGYFTKFGDGAADILPLVNLKKSQVFELGK
 SEQ ID NO: 9   QARLRMMYLYAYAQQNNRIVIGTDNACEWYMGYFTKFGDGAADILPLVNLKKSQVFELGK
 SEQ ID NO: 5   QARLRMMYLYAYAQQNNRIVIGTDNACEWYMGYFTKFGDGAADILPLINLKKSQVFELGK
 SEQ ID NO: 4   QARFRMMYLYAYAQQNNRIVVGTDNACEWYMGYFTKFGDGAADILPLINLKKSQVFELGK
 SEQ ID NO: 3   QARFRMIYLYAYAQQNNRMVIGTDNACEWYMGYFTKFGDGAADILPLIKLKKSQVFELGS
SEQ ID NO: 17   MARLRMIALFTTAQSHRSIVLGTDNAAEWLTGYFTKFGDGAADVLPLAGLRKEQVFELGR
SEQ ID NO: 18   MARLRMIALFTTAQSHRSIVLGTDNAAEMLTGYFTKFGDGAADVLPLARLRKEQVFELGR
 SEQ ID NO:16   MARLRMVMLYTVAQSHRSVVVGTDNAVEYYLGYFTKFGDGACDILPLAKLTKSEVGQLAK
```

Figure 5.

| | |
|---|---|
| SEQ ID NO: 1 | YLDVPKNILDKAPSAGLWQGQTDEDEMGVTYQEIDDFLDGKQVSAKALERINFWHNRSHH |
| SEQ ID NO:15 | YLDVPKNILDKAPSAGLWQGQTDEDEMGVTYQEIDDFLDGKQVSAKALERINFWHNRSHH |
| SEQ ID NO: 14 | YLDVPKNILDKAPSAGLWQGQTDEDEMGVTYQEIDDFLDGKQVSAKALEIINFWHNRSHH |
| SEQ ID NO: 12 | YLDVPKNILDKAPSAGLWQGQTDEDEMGVTYQEIDDFLDGKQVSAKALERINFWHNRSHH |
| SEQ ID NO: 13 | YLDVPKNILDKAPSAGLWQGQTDEDEMGVTYQEIDDFLDGKQVSAKALERINFWHNRSHH |
| SEQ ID NO: 11 | YLDVPKNIIDKAPSAGLWQGQTDEDEMGVTYQEIDDFLDGKQISAKALERINFWHNRSHH |
| SEQ ID NO: 10 | YLGVPKNILDKAPSAGLWQGQTDEDEMGVTYQEIDDFLDGKQVSAKALERINFWHNRSHH |
| SEQ ID NO: 6 | YLKVPQNIIDKAPSAGLWQGQTDEDEMGVTYQEIDNFLDGKEVSAKALERINFWHNRSHH |
| SEQ ID NO: 7 | YLKVPQNIIDKAPSAGLWQGQTDEDEMGVTYQEIDNFLDGKEVSAKALERINFWHNRSHH |
| SEQ ID NO: 8 | YLKVPQNIIDKAPSAGLWQGQTDEDEMGVSYKEIDDFLDGKEVSEKALERINFWHNRSHH |
| SEQ ID NO: 9 | YLKVPQNIIDKAPSAGLWQGQTDEDEMGVSYKEIDDFLDGKEVSEKALERINFWHNRSHH |
| SEQ ID NO: 5 | YLKVPKNIIQKDPSAGLWQGQTDEDEMGVTYKEIDDFLDGKEVSEKALERISFWHNRSHH |
| SEQ ID NO: 4 | YLDVPRNILTKAPSAGLWQGQTDEGEMGVTYQEIDNFLDGKEVSPATFEKISYWHNRSHH |
| SEQ ID NO: 3 | YLNVPNNILTKAPSAGLWLGQTDEAEMGVSYQEIDDFLDGKHVSDYALNQIKFWHNRSHH |
| SEQ ID NO: 17 | YLGVPQSVLDKKPSAGLWAGQTDEAEMGVTYAEIDAYLRGETVSPQALQQIRFWHNRSHH |
| SEQ ID NO: 18 | YLGVPKSVLEKKPSAGLWAGQTDEGEMGVSYAEIDAYLRGETVSPQALKQIQFWHNRSHH |
| SEQ ID NO:16 | ALGVPKKIREKAPSAGLWQGQTDENEIGVSYADLDAFLCGKTVDDAVREKIAYWHQRSHH |

| | |
|---|---|
| SEQ ID NO: 1 | KRKLALTPNF |
| SEQ ID NO:15 | KRKLALTPNF |
| SEQ ID NO: 14 | KRKLALTPNF |
| SEQ ID NO: 12 | KRKLALTPNF |
| SEQ ID NO: 13 | KRKLALTPNF |
| SEQ ID NO: 11 | KRKLALTPNF |
| SEQ ID NO: 10 | KRKLALIPNF |
| SEQ ID NO: 6 | KRSMAFTPNF |
| SEQ ID NO: 7 | KRSMAFTPNF |
| SEQ ID NO: 8 | KRSIAFTPDF |
| SEQ ID NO: 9 | KRSIAFTPDF |
| SEQ ID NO: 5 | KRSMAFTPNF |
| SEQ ID NO: 4 | KRKMALTPDF |
| SEQ ID NO: 3 | KRIMAKAPDF |
| SEQ ID NO: 17 | KRMLPPKPK- |
| SEQ ID NO: 18 | KRMLPPTPE- |
| SEQ ID NO:16 | KRMLPPMPEI |

Figure 5 cont.

SEQUENCE LISTING

```
<160> NUMBER OF SEQ ID NOS: 104

<210> SEQ ID NO 1
<211> LENGTH: 249
<212> TYPE: PRT
<213> ORGANISM: Francisella tularensis

<400> SEQUENCE: 1

Met Lys Ile Val Lys Asp Phe Ser Pro Lys Glu Tyr Ser Gln Lys Leu
1               5                   10                  15

Val Asn Trp Leu Ser Asp Ser Cys Met Asn Tyr Pro Ala Glu Gly Phe
            20                  25                  30

Val Ile Gly Leu Ser Gly Gly Ile Asp Ser Ala Val Ala Ala Ser Leu
        35                  40                  45
```

-continued

```
Ala Val Lys Thr Gly Leu Pro Thr Thr Ala Leu Ile Leu Pro Ser Asp
    50                  55                  60

Asn Asn Gln His Gln Asp Met Gln Asp Ala Leu Glu Leu Ile Glu Met
65                  70                  75                  80

Leu Asn Ile Glu His Tyr Thr Ile Ser Ile Gln Pro Ala Tyr Glu Ala
                85                  90                  95

Phe Leu Ala Ser Thr Gln Ser Phe Thr Asn Leu Gln Asn Asn Arg Gln
            100                 105                 110

Leu Val Ile Lys Gly Asn Ala Gln Ala Arg Leu Arg Met Met Tyr Leu
        115                 120                 125

Tyr Ala Tyr Ala Gln Gln Tyr Asn Arg Ile Val Ile Gly Thr Asp Asn
    130                 135                 140

Ala Cys Glu Trp Tyr Met Gly Tyr Phe Thr Lys Phe Gly Asp Gly Ala
145                 150                 155                 160

Ala Asp Ile Leu Pro Leu Val Asn Leu Lys Lys Ser Gln Val Phe Glu
                165                 170                 175

Leu Gly Lys Tyr Leu Asp Val Pro Lys Asn Ile Leu Asp Lys Ala Pro
            180                 185                 190

Ser Ala Gly Leu Trp Gln Gly Gln Thr Asp Glu Asp Glu Met Gly Val
        195                 200                 205

Thr Tyr Gln Glu Ile Asp Asp Phe Leu Asp Gly Lys Gln Val Ser Ala
    210                 215                 220

Lys Ala Leu Glu Arg Ile Asn Phe Trp His Asn Arg Ser His His Lys
225                 230                 235                 240

Arg Lys Leu Ala Leu Thr Pro Asn Phe
                245
```

<210> SEQ ID NO 2
<211> LENGTH: 750
<212> TYPE: DNA
<213> ORGANISM: Francisella tularensis

<400> SEQUENCE: 2

```
atgaaaatag ttaaagattt tagtcctaaa gaatattcac aaaagttagt taattggcta     60

agtgatagtt gtatgaatta tcctgctgaa ggatttgtga ttggtcttag tggcggtata    120

gattcagcag ttgcggcttc tttagctgtc aaaactggat taccaactac agctttaata    180

ctaccttcag ataataatca acaccaagat atgcaagatg ctctagagct tattgaaatg    240

cttaatattg aacattatac catttcgatt caaccagctt atgaggcttt tcttgcttca    300

acgcaaagct ttacaaatct acaaaacaat agacaacttg tgatcaaggg aaatgctcaa    360

gcacgtttaa ggatgatgta tttgtatgcc tatgcgcaac aatataacag aatagttata    420

ggtactgata atgcttgtga gtggtatatg ggatatttta caaaattcgg tgatggggct    480

gccgatatac ttccactagt taatctcaaa aaatctcaag tttttgaatt aggcaaatac    540

ctagatgtcc ctaaaaacat acttgataaa gctccatctg caggactatg gcaaggacaa    600

actgatgagg atgaaatggg tgtaacttat caagaaattg atgatttctt agatggtaaa    660

caagtttcag caaaagctct agaaagaata aatttctggc ataatcgtag tcaccataag    720

agaaaattag ctttaactcc taatttctag                                     750
```

<210> SEQ ID NO 3
<211> LENGTH: 249
<212> TYPE: PRT
<213> ORGANISM: Francisella sp. FSC1006

-continued

<400> SEQUENCE: 3

Met Ser Val Val Lys Asn Phe Lys Pro Asn Glu Tyr Ala Asn Lys Ile
1 5 10 15

Thr Glu Trp Leu Lys Asp Ser Cys Leu Asn Tyr Pro Ala Glu Gly Phe
20 25 30

Val Val Gly Ile Ser Gly Gly Ile Asp Ser Ala Val Ala Val Ser Leu
35 40 45

Ala Val Asn Thr Gly Leu Pro Val Thr Gly Leu Ile Met Pro Ser Lys
50 55 60

Asn Asn Asp Asp Lys Asp Thr Leu Asp Ala Ile Glu Leu Ala Lys Lys
65 70 75 80

Leu Asn Ile Glu Tyr His Leu Ile Pro Ile Gln Pro Val Tyr Glu Thr
85 90 95

Phe Leu Asp Ser Ala Glu Asp Ile Lys Asn Ser Ala Asn Asp Arg Gln
100 105 110

His Val Ile Lys Gly Asn Ala Gln Ala Arg Phe Arg Met Ile Tyr Leu
115 120 125

Tyr Ala Tyr Ala Gln Gln Asn Asn Arg Met Val Ile Gly Thr Asp Asn
130 135 140

Ala Cys Glu Trp Tyr Met Gly Tyr Phe Thr Lys Phe Gly Asp Gly Ala
145 150 155 160

Ala Asp Ile Leu Pro Leu Ile Lys Leu Lys Lys Ser Gln Val Phe Glu
165 170 175

Leu Gly Ser Tyr Leu Asn Val Pro Asn Asn Ile Leu Thr Lys Ala Pro
180 185 190

Ser Ala Gly Leu Trp Leu Gly Gln Thr Asp Glu Ala Glu Met Gly Val
195 200 205

Ser Tyr Gln Glu Ile Asp Asp Phe Leu Asp Gly Lys His Val Ser Asp
210 215 220

Tyr Ala Leu Asn Gln Ile Lys Phe Trp His Asn Arg Ser His His Lys
225 230 235 240

Arg Ile Met Ala Lys Ala Pro Asp Phe
245

<210> SEQ ID NO 4
<211> LENGTH: 249
<212> TYPE: PRT
<213> ORGANISM: Francisella guangzhouensis strain 08HL01032

<400> SEQUENCE: 4

Met Asn Val Val Lys Asn Phe Thr Pro Glu Lys Tyr Ser Glu Lys Leu
1 5 10 15

Ile Gln Trp Leu Thr Asn Ser Cys Ile Lys Tyr Pro Ala Glu Gly Phe
20 25 30

Val Ile Gly Val Ser Gly Gly Ile Asp Ser Ala Val Cys Ala Ser Leu
35 40 45

Leu Ser Lys Thr Asp Leu Pro Thr Thr Ala Phe Ile Leu Pro Ser Lys
50 55 60

Asn Asn Ser Asp Gln Asp Met Ile Asp Ala Leu Glu Leu Ile Asn Lys
65 70 75 80

Leu Asn Ile Pro Tyr His Ile Ile Pro Ile Gln Pro Val Tyr Glu Ser
85 90 95

Phe Leu Lys Ser Thr Gln Leu Phe Thr Asn Pro Gln Asn Asp Arg Gln
100 105 110

-continued

```
Asn Val Ile Lys Gly Asn Ala Gln Ala Arg Phe Arg Met Met Tyr Leu
        115                 120                 125

Tyr Ala Tyr Ala Gln Gln Asn Asn Arg Ile Val Val Gly Thr Asp Asn
    130                 135                 140

Ala Cys Glu Trp Tyr Met Gly Tyr Phe Thr Lys Phe Gly Asp Gly Ala
145                 150                 155                 160

Ala Asp Ile Leu Pro Leu Ile Asn Leu Lys Lys Ser Gln Val Phe Glu
                165                 170                 175

Leu Gly Lys Tyr Leu Asp Val Pro Arg Asn Ile Leu Thr Lys Ala Pro
            180                 185                 190

Ser Ala Gly Leu Trp Gln Gly Gln Thr Asp Glu Gly Glu Met Gly Val
        195                 200                 205

Thr Tyr Gln Glu Ile Asp Asn Phe Leu Asp Gly Lys Glu Val Ser Pro
    210                 215                 220

Ala Thr Phe Glu Lys Ile Ser Tyr Trp His Asn Arg Ser His His Lys
225                 230                 235                 240

Arg Lys Met Ala Leu Thr Pro Asp Phe
                245


<210> SEQ ID NO 5
<211> LENGTH: 249
<212> TYPE: PRT
<213> ORGANISM: Francisella sp. TX077308

<400> SEQUENCE: 5

Met Lys Ile Val Lys Asn Phe Ile Val Glu Gln Tyr Ser Asn Asn Leu
1               5                   10                  15

Ile Lys Trp Leu Lys Glu Asn Cys Ile Lys Tyr Pro Ala Glu Gly Phe
            20                  25                  30

Val Ile Gly Ile Ser Gly Gly Ile Asp Ser Ala Val Ala Ala Ser Leu
        35                  40                  45

Ala Val Lys Thr Gly Leu Pro Thr Thr Ala Leu Ile Leu Pro Ser Lys
    50                  55                  60

Asn Asn Gln Asp Gln Asp Met Arg Asp Gly Ile Glu Leu Ile Glu Asn
65                  70                  75                  80

Leu Asn Ile Glu Tyr His Thr Val Ser Ile Gln Pro Ala Tyr Asp Thr
                85                  90                  95

Phe Ile Glu Ser Thr Phe Asn Phe Thr Asn Ser Gln Asn Asp Arg Gln
            100                 105                 110

His Val Ile Lys Gly Asn Ala Gln Ala Arg Leu Arg Met Met Tyr Leu
        115                 120                 125

Tyr Ala Tyr Ala Gln Gln Asn Asn Arg Ile Val Ile Gly Thr Asp Asn
    130                 135                 140

Ala Cys Glu Trp Tyr Met Gly Tyr Phe Thr Lys Phe Gly Asp Gly Ala
145                 150                 155                 160

Ala Asp Ile Leu Pro Leu Ile Asn Leu Lys Lys Ser Gln Val Phe Glu
                165                 170                 175

Leu Gly Lys Tyr Leu Lys Val Pro Lys Asn Ile Ile Gln Lys Asp Pro
            180                 185                 190

Ser Ala Gly Leu Trp Gln Gly Gln Thr Asp Glu Asp Glu Met Gly Val
        195                 200                 205

Thr Tyr Lys Glu Ile Asp Asp Phe Leu Asp Gly Lys Glu Val Ser Glu
    210                 215                 220

Lys Ala Leu Glu Arg Ile Ser Phe Trp His Asn Arg Ser His His Lys
225                 230                 235                 240
```

Arg Ser Met Ala Phe Thr Pro Asn Phe
245

<210> SEQ ID NO 6
<211> LENGTH: 249
<212> TYPE: PRT
<213> ORGANISM: Francisella philomiragia subsp. philomiragia ATCC 25017

<400> SEQUENCE: 6

```
Met Lys Ile Ile Lys Asn Phe Ile Ala Glu Glu Tyr Ser Lys Lys Leu
1               5                   10                  15

Ile Glu Trp Leu Lys Lys Ile Cys Ile Asn Tyr Pro Ala Glu Gly Phe
            20                  25                  30

Val Ile Gly Ile Ser Gly Gly Ile Asp Ser Ala Val Ala Ala Ser Leu
        35                  40                  45

Ala Val Lys Thr Gly Leu Pro Thr Thr Ala Leu Ile Leu Pro Ser Lys
    50                  55                  60

Asn Asn Gln Asp Gln Asp Met Lys Asp Gly Leu Glu Leu Ile Lys Asn
65                  70                  75                  80

Leu Asp Ile Glu His His Ile Val Pro Ile Gln Pro Ala Tyr Asp Thr
                85                  90                  95

Phe Ile Glu Ser Thr Leu Asn Phe Thr Asn Ser Gln Asn Asp Arg Gln
            100                 105                 110

His Val Ile Lys Gly Asn Ala Gln Ala Arg Leu Arg Met Met Tyr Leu
        115                 120                 125

Tyr Ala Tyr Ala Gln Gln Asn Asn Arg Ile Val Ile Gly Thr Asp Asn
    130                 135                 140

Ala Cys Glu Trp Tyr Met Gly Tyr Phe Thr Lys Phe Gly Asp Gly Ala
145                 150                 155                 160

Ala Asp Ile Leu Pro Leu Val Asn Leu Lys Lys Ser Gln Val Phe Glu
                165                 170                 175

Met Gly Lys Tyr Leu Lys Val Pro Gln Asn Ile Ile Asp Lys Ala Pro
            180                 185                 190

Ser Ala Gly Leu Trp Gln Gly Gln Thr Asp Glu Asp Glu Met Gly Val
        195                 200                 205

Thr Tyr Gln Glu Ile Asp Asn Phe Leu Asp Gly Lys Glu Val Ser Ala
    210                 215                 220

Lys Ala Leu Glu Arg Ile Asn Phe Trp His Asn Arg Ser His His Lys
225                 230                 235                 240

Arg Ser Met Ala Phe Thr Pro Asn Phe
                245
```

<210> SEQ ID NO 7
<211> LENGTH: 249
<212> TYPE: PRT
<213> ORGANISM: Francisella philomiragia strain O#319-036 [FSC 153

<400> SEQUENCE: 7

```
Met Lys Ile Ile Lys Asn Phe Ile Ala Glu Glu Tyr Ser Lys Lys Leu
1               5                   10                  15

Ile Glu Trp Leu Lys Lys Ile Cys Ile Asn Tyr Pro Ala Glu Gly Phe
            20                  25                  30

Val Ile Gly Ile Ser Gly Gly Ile Asp Ser Ala Val Ala Ala Ser Leu
        35                  40                  45

Ala Val Lys Thr Gly Leu Pro Thr Thr Ala Leu Ile Leu Pro Ser Lys
    50                  55                  60
```

```
Asn Asn Gln Asp Gln Asp Met Lys Asp Gly Leu Glu Leu Ile Lys Asn
65                  70                  75                  80

Leu Asp Ile Glu His His Ile Val Pro Ile Gln Pro Ala Tyr Asp Thr
                85                  90                  95

Phe Ile Glu Ser Thr Leu Asn Phe Thr Asn Ser Gln Asn Asp Arg Gln
            100                 105                 110

His Val Ile Lys Gly Asn Ala Gln Ala Arg Leu Arg Met Met Tyr Leu
        115                 120                 125

Tyr Ala Tyr Ala Gln Gln Asn Asn Arg Ile Val Ile Gly Thr Asp Asn
    130                 135                 140

Ala Cys Glu Trp Tyr Met Gly Tyr Phe Thr Lys Phe Gly Asp Gly Ala
145                 150                 155                 160

Ala Asp Ile Leu Pro Leu Val Asn Leu Lys Lys Ser Gln Val Phe Glu
                165                 170                 175

Met Gly Glu Tyr Leu Lys Val Pro Gln Asn Ile Ile Asp Lys Ala Pro
            180                 185                 190

Ser Ala Gly Leu Trp Gln Gly Gln Thr Asp Glu Asp Glu Met Gly Val
        195                 200                 205

Thr Tyr Gln Glu Ile Asp Asn Phe Leu Asp Gly Lys Glu Val Ser Ala
    210                 215                 220

Lys Ala Leu Glu Arg Ile Asn Phe Trp His Asn Arg Ser His His Lys
225                 230                 235                 240

Arg Ser Met Ala Phe Thr Pro Asn Phe
                245


<210> SEQ ID NO 8
<211> LENGTH: 249
<212> TYPE: PRT
<213> ORGANISM: Francisella noatunensis subsp. orientalis str. Toba 04

<400> SEQUENCE: 8

Met Lys Ile Ile Lys Asn Phe Ile Ala Lys Glu Tyr Ser Lys Lys Leu
1               5                   10                  15

Ile Glu Trp Leu Lys Lys Ile Cys Ile Asn Tyr Pro Ala Glu Gly Phe
            20                  25                  30

Val Ile Gly Ile Ser Gly Gly Ile Asp Ser Ala Val Ala Ala Ser Leu
        35                  40                  45

Ala Val Lys Thr Gly Leu Pro Thr Thr Ala Leu Ile Leu Pro Ser Lys
    50                  55                  60

Asn Asn Gln Asp Gln Asp Met Lys Asp Gly Leu Glu Leu Ile Lys Asn
65                  70                  75                  80

Leu Asp Ile Glu His His Ile Val Pro Ile Gln Pro Ala Tyr Asp Thr
                85                  90                  95

Phe Ile Glu Ser Thr Phe Asn Phe Thr Asn Ala Gln Asn Asn Arg Gln
            100                 105                 110

His Val Ile Lys Gly Asn Ala Gln Ala Arg Leu Arg Met Met Tyr Leu
        115                 120                 125

Tyr Ala Tyr Ala Gln Gln Asn Asn Arg Ile Val Ile Gly Thr Asp Asn
    130                 135                 140

Ala Cys Glu Trp Tyr Met Gly Tyr Phe Thr Lys Phe Gly Asp Gly Ala
145                 150                 155                 160

Ala Asp Ile Leu Pro Leu Val Asn Leu Lys Lys Ser Gln Val Phe Glu
                165                 170                 175

Leu Gly Lys Tyr Leu Lys Val Pro Gln Asn Ile Ile Asp Lys Ala Pro
```

```
            180                 185                 190

Ser Ala Gly Leu Trp Gln Gly Gln Thr Asp Glu Asp Glu Met Gly Val
        195                 200                 205

Ser Tyr Lys Glu Ile Asp Asp Phe Leu Asp Gly Lys Glu Val Ser Glu
    210                 215                 220

Lys Ala Leu Glu Arg Ile Asn Phe Trp His Asn Arg Ser His His Lys
225                 230                 235                 240

Arg Ser Ile Ala Phe Thr Pro Asp Phe
                245


<210> SEQ ID NO 9
<211> LENGTH: 249
<212> TYPE: PRT
<213> ORGANISM: Francisella philomiragia strain GA01-2794

<400> SEQUENCE: 9

Met Lys Ile Ile Lys Asn Phe Ile Val Glu Lys Tyr Ser Lys Lys Leu
1               5                   10                  15

Ile Glu Trp Leu Lys Lys Ile Cys Ile Asn Tyr Pro Ala Glu Gly Phe
            20                  25                  30

Val Ile Gly Ile Ser Gly Gly Ile Asp Ser Ala Val Ala Ala Ser Leu
        35                  40                  45

Ala Val Lys Thr Gly Leu Pro Thr Thr Ala Leu Ile Leu Pro Ser Lys
    50                  55                  60

Asn Asn Gln Asp Gln Asp Met Lys Asp Gly Leu Glu Leu Ile Lys Asn
65                  70                  75                  80

Leu Asp Ile Glu His His Ile Val Pro Ile Gln Pro Ala Tyr Asp Thr
                85                  90                  95

Phe Ile Glu Ser Thr Phe Asn Phe Thr Asn Ala Gln Asn Asn Arg Gln
            100                 105                 110

His Val Ile Lys Gly Asn Ala Gln Ala Arg Leu Arg Met Met Tyr Leu
        115                 120                 125

Tyr Ala Tyr Ala Gln Gln Asn Asn Arg Ile Val Ile Gly Thr Asp Asn
    130                 135                 140

Ala Cys Glu Trp Tyr Met Gly Tyr Phe Thr Lys Phe Gly Asp Gly Ala
145                 150                 155                 160

Ala Asp Ile Leu Pro Leu Val Asn Leu Lys Lys Ser Gln Val Phe Glu
                165                 170                 175

Leu Gly Lys Tyr Leu Lys Val Pro Gln Asn Ile Ile Asp Lys Ala Pro
            180                 185                 190

Ser Ala Gly Leu Trp Gln Gly Gln Thr Asp Glu Asp Glu Met Gly Val
        195                 200                 205

Ser Tyr Lys Glu Ile Asp Asp Phe Leu Asp Gly Lys Glu Val Ser Glu
    210                 215                 220

Lys Ala Leu Glu Arg Ile Asn Phe Trp His Asn Arg Ser His His Lys
225                 230                 235                 240

Arg Ser Ile Ala Phe Thr Pro Asp Phe
                245


<210> SEQ ID NO 10
<211> LENGTH: 249
<212> TYPE: PRT
<213> ORGANISM: Francisella persica ATCC VR-331

<400> SEQUENCE: 10

Met Lys Ile Val Lys Asp Phe Asn Ile Lys Glu Tyr Ser Gln Lys Leu
```

-continued

```
1               5                   10                  15

Ile Asp Trp Leu Ser Asp Thr Cys Met Asn Tyr Pro Ala Glu Gly Phe
            20                  25                  30

Val Ile Gly Leu Ser Gly Gly Ile Asp Ser Ala Val Ala Ala Ser Leu
        35                  40                  45

Ala Val Lys Thr Gly Leu Ser Thr Thr Ala Leu Ile Leu Pro Ser Lys
    50                  55                  60

Asn Asn Gln His Gln Asp Ile Gln Asp Ala Leu Glu Leu Ala Asp Lys
65                  70                  75                  80

Ile Asn Ile Glu His His Thr Ile Thr Ile Gln Thr Val Tyr Glu Thr
                85                  90                  95

Phe Leu Ala Ser Ile Lys Lys Ile Thr Asn Thr Glu Arg Asp Arg Gln
            100                 105                 110

Leu Val Ile Lys Gly Asn Ala Gln Ala Arg Leu Arg Met Met Tyr Leu
        115                 120                 125

Tyr Ala Tyr Ala Gln Gln Tyr Asn Arg Val Val Ile Gly Thr Asp Asn
    130                 135                 140

Ala Cys Glu Trp Tyr Met Gly Tyr Phe Thr Lys Phe Gly Asp Gly Ala
145                 150                 155                 160

Ala Asp Ile Leu Pro Leu Val Asn Leu Lys Lys Ser His Val Phe Glu
                165                 170                 175

Leu Gly Lys Tyr Leu Gly Val Pro Lys Asn Ile Leu Asp Lys Ala Pro
            180                 185                 190

Ser Ala Gly Leu Trp Gln Gly Gln Thr Asp Glu Asp Glu Met Gly Val
        195                 200                 205

Thr Tyr Gln Glu Ile Asp Asp Phe Leu Asp Gly Lys Gln Val Ser Ala
    210                 215                 220

Lys Ala Leu Glu Arg Ile Asn Phe Trp His Asn Arg Ser His His Lys
225                 230                 235                 240

Arg Lys Leu Ala Leu Ile Pro Asn Phe
                245
```

<210> SEQ ID NO 11
<211> LENGTH: 249
<212> TYPE: PRT
<213> ORGANISM: Francisella cf. novicida 3523

<400> SEQUENCE: 11

```
Met Lys Ile Val Lys Asp Phe Ser Pro Lys Glu Tyr Ser Gln Asn Leu
1               5                   10                  15

Val Asn Trp Leu Ser Asp Thr Cys Ile Asn Tyr Pro Ala Glu Gly Phe
            20                  25                  30

Val Ile Gly Ile Ser Gly Gly Ile Asp Ser Ala Val Ala Ala Ser Leu
        35                  40                  45

Ala Val Lys Thr Gly Leu Pro Thr Thr Ala Leu Ile Leu Pro Ser Lys
    50                  55                  60

Asn Asn Gln His Gln Asp Ile Gln Asp Ala Leu Glu Leu Val Glu Lys
65                  70                  75                  80

Leu Asn Ile Glu His His Ile Val Thr Ile Gln Pro Ala Tyr Glu Asn
                85                  90                  95

Phe Leu Ala Ser Thr Gln Glu Phe Ile Asn Thr Asp Asn Asn Arg Gln
            100                 105                 110

Leu Val Ile Lys Gly Asn Ala Gln Ala Arg Leu Arg Met Met Tyr Leu
        115                 120                 125
```

```
Tyr Ala Tyr Ala Gln Gln Tyr Asn Arg Ile Val Ile Gly Thr Asp Asn
    130                 135                 140

Ala Cys Glu Trp Tyr Met Gly Tyr Phe Thr Lys Phe Gly Asp Gly Ala
145                 150                 155                 160

Ala Asp Ile Phe Pro Leu Ile Asn Leu Lys Lys Ser Gln Val Phe Glu
                165                 170                 175

Leu Gly Lys Tyr Leu Asp Val Pro Lys Asn Ile Ile Asp Lys Ala Pro
            180                 185                 190

Ser Ala Gly Leu Trp Gln Gly Gln Thr Asp Glu Asp Glu Met Gly Val
        195                 200                 205

Thr Tyr Gln Glu Ile Asp Asp Phe Leu Asp Gly Lys Gln Ile Ser Ala
    210                 215                 220

Lys Ala Leu Glu Arg Ile Asn Phe Trp His Asn Arg Ser His His Lys
225                 230                 235                 240

Arg Lys Leu Ala Leu Thr Pro Asn Phe
                245


<210> SEQ ID NO 12
<211> LENGTH: 249
<212> TYPE: PRT
<213> ORGANISM: Francisella tularensis subsp. novicida D9876

<400> SEQUENCE: 12

Met Lys Ile Val Lys Asp Phe Ser Pro Lys Glu Tyr Ser Gln Lys Leu
1               5                   10                  15

Val Asn Trp Leu Ser Asp Ser Cys Met Asn Tyr Pro Ala Glu Gly Phe
            20                  25                  30

Val Ile Gly Leu Ser Gly Gly Ile Asp Ser Ala Val Ala Ala Ser Leu
        35                  40                  45

Ala Val Lys Thr Gly Leu Pro Thr Thr Ala Leu Ile Leu Pro Ser Asp
    50                  55                  60

Asn Asn Gln His Gln Asp Met Gln Asp Ala Leu Asp Leu Ile Glu Met
65                  70                  75                  80

Leu Asn Ile Glu His Tyr Thr Ile Ser Ile Gln Pro Ala Tyr Glu Ala
                85                  90                  95

Phe Leu Ala Ser Thr Gln Arg Phe Thr Asn Leu Gln Asn Asn Arg Gln
            100                 105                 110

Leu Val Ile Lys Gly Asn Ala Gln Ala Arg Leu Arg Met Met Tyr Leu
        115                 120                 125

Tyr Ala Tyr Ala Gln Gln Tyr Asn Arg Ile Val Ile Gly Thr Asp Asn
    130                 135                 140

Ala Cys Glu Trp Tyr Met Gly Tyr Phe Thr Lys Phe Gly Asp Gly Ala
145                 150                 155                 160

Ala Asp Ile Leu Pro Leu Val Asn Leu Lys Lys Ser Gln Val Phe Glu
                165                 170                 175

Leu Gly Lys Tyr Leu Asp Val Pro Lys Asn Ile Leu Asp Lys Ala Pro
            180                 185                 190

Ser Ala Gly Leu Trp Gln Gly Gln Thr Asp Glu Asp Glu Met Gly Val
        195                 200                 205

Thr Tyr Gln Glu Ile Asp Asp Phe Leu Asp Gly Lys Gln Val Ser Ala
    210                 215                 220

Lys Ala Leu Glu Arg Ile Asn Phe Trp His Asn Arg Ser His His Lys
225                 230                 235                 240

Arg Lys Leu Ala Leu Thr Pro Asn Phe
                245
```

<210> SEQ ID NO 13
<211> LENGTH: 249
<212> TYPE: PRT
<213> ORGANISM: Francisella tularensis subsp. novicida F6168

<400> SEQUENCE: 13

```
Met Lys Ile Val Lys Asp Phe Ser Pro Lys Glu Tyr Ser Gln Lys Leu
1               5                   10                  15

Val Asn Trp Leu Ser Asp Ser Cys Met Asn Tyr Pro Ala Glu Gly Phe
            20                  25                  30

Val Ile Gly Leu Ser Gly Gly Ile Asp Ser Ala Val Ala Ala Ser Leu
        35                  40                  45

Ala Val Lys Thr Gly Leu Pro Ile Thr Ala Leu Ile Leu Pro Ser Asp
    50                  55                  60

Asn Asn Gln His Gln Asp Met Gln Asp Ala Leu Asp Leu Ile Glu Met
65                  70                  75                  80

Leu Asn Ile Glu His Tyr Thr Ile Ser Ile Gln Pro Ala Tyr Glu Ala
                85                  90                  95

Phe Leu Ala Ser Thr Gln Ser Phe Thr Asn Leu Gln Asn Asn Arg Gln
            100                 105                 110

Leu Val Ile Lys Gly Asn Ala Gln Ala Arg Leu Arg Met Met Tyr Leu
        115                 120                 125

Tyr Ala Tyr Ala Gln Gln Tyr Asn Arg Ile Val Ile Gly Thr Asp Asn
    130                 135                 140

Ala Cys Glu Trp Tyr Met Gly Tyr Phe Thr Lys Phe Gly Asp Gly Ala
145                 150                 155                 160

Ala Asp Ile Leu Pro Leu Val Asn Leu Lys Lys Ser Gln Val Phe Glu
                165                 170                 175

Leu Gly Lys Tyr Leu Asp Val Pro Lys Asn Ile Leu Asp Lys Ala Pro
            180                 185                 190

Ser Ala Gly Leu Trp Gln Gly Gln Thr Asp Glu Asp Glu Met Gly Val
        195                 200                 205

Thr Tyr Gln Glu Ile Asp Asp Phe Leu Asp Gly Lys Gln Val Ser Ala
    210                 215                 220

Lys Ala Leu Glu Arg Ile Asn Phe Trp His Asn Arg Ser His His Lys
225                 230                 235                 240

Arg Lys Leu Ala Leu Thr Pro Asn Phe
                245
```

<210> SEQ ID NO 14
<211> LENGTH: 249
<212> TYPE: PRT
<213> ORGANISM: Francisella tularensis subsp. tularensis strain NIH B-38

<400> SEQUENCE: 14

```
Met Lys Ile Val Lys Asp Phe Ser Pro Lys Glu Tyr Ser Gln Lys Leu
1               5                   10                  15

Val Asn Trp Leu Ser Asp Ser Cys Met Asn Tyr Pro Ala Glu Gly Phe
            20                  25                  30

Val Ile Gly Leu Ser Gly Gly Ile Asp Ser Ala Val Ala Ala Ser Leu
        35                  40                  45

Ala Val Lys Thr Gly Leu Pro Thr Thr Ala Leu Ile Leu Pro Ser Asp
    50                  55                  60

Asn Asn Gln His Gln Asp Met Gln Asp Ala Leu Glu Leu Ile Glu Met
65                  70                  75                  80
```

Leu Asn Ile Glu His Tyr Thr Ile Ser Ile Gln Leu Ala Tyr Glu Ala
85 90 95

Phe Leu Ala Ser Thr Gln Ser Phe Thr Asn Leu Gln Asn Asn Arg Gln
100 105 110

Leu Val Ile Lys Gly Asn Ala Gln Ala Arg Leu Arg Met Met Tyr Leu
115 120 125

Tyr Ala Tyr Ala Gln Gln Tyr Asn Arg Ile Val Ile Gly Thr Asp Asn
130 135 140

Ala Cys Glu Trp Tyr Met Gly Tyr Phe Thr Lys Phe Gly Asp Gly Ala
145 150 155 160

Ala Asp Ile Leu Pro Leu Val Asn Leu Lys Lys Ser Gln Val Phe Glu
165 170 175

Leu Gly Lys Tyr Leu Asp Val Pro Lys Asn Ile Leu Asp Lys Ala Pro
180 185 190

Ser Ala Gly Leu Trp Gln Gly Gln Thr Asp Glu Asp Glu Met Gly Val
195 200 205

Thr Tyr Gln Glu Ile Asp Asp Phe Leu Asp Gly Lys Gln Val Ser Ala
210 215 220

Lys Ala Leu Glu Ile Ile Asn Phe Trp His Asn Arg Ser His His Lys
225 230 235 240

Arg Lys Leu Ala Leu Thr Pro Asn Phe
245

<210> SEQ ID NO 15
<211> LENGTH: 249
<212> TYPE: PRT
<213> ORGANISM: Francisella tularensis subsp. holarctica F92

<400> SEQUENCE: 15

Met Lys Ile Val Lys Asp Phe Ser Pro Lys Glu Tyr Ser Gln Lys Leu
1 5 10 15

Val Asn Trp Leu Ser Asp Ser Cys Met Asn Tyr Pro Ala Glu Gly Phe
20 25 30

Val Ile Gly Leu Ser Gly Gly Ile Asp Ser Ala Val Ala Ala Ser Leu
35 40 45

Ala Val Lys Thr Gly Leu Pro Thr Thr Ala Leu Ile Leu Pro Ser Asp
50 55 60

Asn Asn Gln His Gln Asp Met Gln Asp Ala Leu Glu Leu Ile Glu Met
65 70 75 80

Leu Asn Ile Glu His Tyr Thr Ile Ser Ile Gln Pro Ala Tyr Glu Ala
85 90 95

Phe Leu Ala Ser Thr Gln Ser Phe Thr Asn Leu Gln Asn Asn Arg Gln
100 105 110

Leu Val Ile Lys Gly Asn Ala Gln Thr Arg Leu Arg Met Met Tyr Leu
115 120 125

Tyr Ala Tyr Ala Gln Gln Tyr Asn Arg Ile Val Ile Gly Thr Asp Asn
130 135 140

Ala Cys Glu Trp Tyr Met Gly Tyr Phe Thr Lys Phe Gly Asp Gly Ala
145 150 155 160

Ala Asp Ile Leu Pro Leu Val Asn Leu Lys Lys Ser Gln Val Phe Glu
165 170 175

Leu Gly Lys Tyr Leu Asp Val Pro Lys Asn Ile Leu Asp Lys Ala Pro
180 185 190

Ser Ala Gly Leu Trp Gln Gly Gln Thr Asp Glu Asp Glu Met Gly Val

-continued

```
        195                 200                 205

Thr Tyr Gln Glu Ile Asp Asp Phe Leu Asp Gly Lys Gln Val Ser Ala
    210                 215                 220

Lys Ala Leu Glu Arg Ile Asn Phe Trp His Asn Arg Ser His His Lys
225                 230                 235                 240

Arg Lys Leu Ala Leu Thr Pro Asn Phe
                245


<210> SEQ ID NO 16
<211> LENGTH: 239
<212> TYPE: PRT
<213> ORGANISM: Dichelobacter nodosus VCS1703A

<400> SEQUENCE: 16

Gln Tyr Ile Asp Tyr Leu Leu Val Trp Leu Glu Glu Gln Arg Ala His
1               5                   10                  15

Leu Tyr Ala Ser Asp Gly Tyr Thr Leu Gly Val Ser Gly Gly Ile Asp
            20                  25                  30

Ser Ala Val Cys Leu His Leu Leu Ala Lys Thr Gly Lys Pro Val Gln
        35                  40                  45

Ala Leu Val Leu Pro Ile Asn Ala Asn Ala Asn Asp Cys Glu Asp Ala
    50                  55                  60

Glu Leu Val Leu Lys Asn Ala Asn Ile Ser Gly Asn Ile Ile Ala Leu
65                  70                  75                  80

Asp Asp Val Tyr Thr Ala Ala Gln Asn Thr Leu Ala Pro Val Leu Asn
                85                  90                  95

Arg Asp Tyr Glu Arg Met Pro Val Leu Asn Gly Asn Leu Met Ala Arg
            100                 105                 110

Leu Arg Met Val Met Leu Tyr Thr Val Ala Gln Ser His Arg Ser Val
        115                 120                 125

Val Val Gly Thr Asp Asn Ala Val Glu Tyr Tyr Leu Gly Tyr Phe Thr
    130                 135                 140

Lys Phe Gly Asp Gly Ala Cys Asp Ile Leu Pro Leu Ala Lys Leu Thr
145                 150                 155                 160

Lys Ser Glu Val Gly Gln Leu Ala Lys Ala Leu Gly Val Pro Lys Lys
                165                 170                 175

Ile Arg Glu Lys Ala Pro Ser Ala Gly Leu Trp Gln Gly Gln Thr Asp
            180                 185                 190

Glu Asn Glu Ile Gly Val Ser Tyr Ala Asp Leu Asp Ala Phe Leu Cys
        195                 200                 205

Gly Lys Thr Val Asp Asp Ala Val Arg Glu Lys Ile Ala Tyr Trp His
    210                 215                 220

Gln Arg Ser His His Lys Arg Met Leu Pro Pro Met Pro Glu Ile
225                 230                 235


<210> SEQ ID NO 17
<211> LENGTH: 245
<212> TYPE: PRT
<213> ORGANISM: Mannheimia succiniciproducens MBEL55E

<400> SEQUENCE: 17

Lys Arg Met Lys Thr Ala Ala Tyr Ala Asp Tyr Leu Ile Gln Trp Leu
1               5                   10                  15

Glu Asn Gln Arg Thr Glu Leu Tyr Gly Met Asp Gly Tyr Thr Leu Gly
            20                  25                  30

Val Ser Gly Gly Ile Asp Ser Ala Val Cys Ala His Leu Ala Ala Arg
```

-continued

```
        35                  40                  45

Thr Gly Ala Pro Val Gln Ala Leu Ile Leu Pro Ala Glu Val Thr Ser
    50                  55                  60

Pro Ser Asp Val Ala Asp Ala Gln Ala Thr Leu Glu Ser Ala Gly Ile
65                  70                  75                  80

Asp Gly Gln Ile Ile Ser Ile Ala Pro Trp Tyr Asp Leu Ile Met Gln
                85                  90                  95

Gln Leu Ser Pro Val Leu Asn Ser Glu Pro Glu Arg Val Asn Val Leu
            100                 105                 110

Lys Gly Asn Leu Met Ala Arg Leu Arg Met Ile Ala Leu Phe Thr Thr
        115                 120                 125

Ala Gln Ser His Arg Ser Ile Val Leu Gly Thr Asp Asn Ala Ala Glu
    130                 135                 140

Trp Leu Thr Gly Tyr Phe Thr Lys Phe Gly Asp Gly Ala Ala Asp Val
145                 150                 155                 160

Leu Pro Leu Ala Gly Leu Arg Lys Glu Gln Val Phe Glu Leu Gly Arg
                165                 170                 175

Tyr Leu Gly Val Pro Gln Ser Val Leu Asp Lys Lys Pro Ser Ala Gly
            180                 185                 190

Leu Trp Ala Gly Gln Thr Asp Glu Ala Glu Met Gly Val Thr Tyr Ala
        195                 200                 205

Glu Ile Asp Ala Tyr Leu Arg Gly Glu Thr Val Ser Pro Gln Ala Leu
    210                 215                 220

Gln Gln Ile Arg Phe Trp His Asn Arg Ser His His Lys Arg Met Leu
225                 230                 235                 240

Pro Pro Lys Pro Lys
                245


<210> SEQ ID NO 18
<211> LENGTH: 238
<212> TYPE: PRT
<213> ORGANISM: Actinobacillus succinogenes 130Z

<400> SEQUENCE: 18

Tyr Val Asp Tyr Leu Val Arg Trp Leu Glu Thr Gln Arg Thr Glu Leu
1               5                   10                  15

Tyr Gly Met Asp Gly Tyr Thr Leu Gly Val Ser Gly Gly Ile Asp Ser
            20                  25                  30

Ala Val Cys Ala His Leu Ala Ala Arg Thr Gly Ala Pro Val Gln Ala
        35                  40                  45

Leu Ile Leu Pro Ala Glu Val Thr Ser Pro Glu Asp Val Ala Asp Ala
    50                  55                  60

Gln Ile Thr Leu Glu Ser Ala Gly Ile Asp Gly Arg Ile Ile Ser Ile
65                  70                  75                  80

Ala Pro Trp Tyr Asp Leu Ile Met Leu Gln Leu Thr Pro Ala Leu Asn
                85                  90                  95

Ala Glu Ser Glu Arg Ile Asn Val Leu Lys Gly Asn Leu Met Ala Arg
            100                 105                 110

Leu Arg Met Ile Ala Leu Phe Thr Thr Ala Gln Ser His Arg Ser Ile
        115                 120                 125

Val Leu Gly Thr Asp Asn Ala Ala Glu Met Leu Thr Gly Tyr Phe Thr
    130                 135                 140

Lys Phe Gly Asp Gly Ala Ala Asp Val Leu Pro Leu Ala Arg Leu Arg
145                 150                 155                 160
```

-continued

```
Lys Glu Gln Val Phe Glu Leu Gly Arg Tyr Leu Gly Val Pro Lys Ser
                165                 170                 175

Val Leu Glu Lys Lys Pro Ser Ala Gly Leu Trp Ala Gly Gln Thr Asp
            180                 185                 190

Glu Gly Glu Met Gly Val Ser Tyr Ala Glu Ile Asp Ala Tyr Leu Arg
        195                 200                 205

Gly Glu Thr Val Ser Pro Gln Ala Leu Lys Gln Ile Gln Phe Trp His
    210                 215                 220

Asn Arg Ser His His Lys Arg Met Leu Pro Pro Thr Pro Glu
225                 230                 235
```

```
<210> SEQ ID NO 19
<211> LENGTH: 753
<212> TYPE: DNA
<213> ORGANISM: Mannheimia succiniciproducens MBEL55E

<400> SEQUENCE: 19

atgaaaacgg cagcatacgc agattattta attcaatggc tggaaaacca acgaaccgaa      60

ctttacggga tggacggcta tacactgggc gtcagcggcg gtattgacag cgccgtctgc     120

gctcatttgg cagcgcgcac cggcgcaccg gtacaagcct taattttgcc cgccgaagta     180

accagtccgt cagatgtggc ggatgcgcaa gccacactgg aaagcgccgg tattgacgga     240

caaataattt ccattgcacc ttggtacgat ttaattatgc aacaactttc cccggtatta     300

aattccgaac cggagcgcgt taacgtatta aagggtaatt taatggcaag actgcgtatg     360

attgcgctgt ttaccacggc acaaagccat cgttctattg tgttaggcac cgataatgcg     420

gcggaatggc tgacgggtta ttttaccaaa ttcggcgacg gcgcagcgga cgtactgcct     480

ttagcgggat tgcgcaaaga gcaggtattt gaactcggac gttatcttgg cgtaccgcaa     540

agcgtgctgg ataaaaaacc gagcgccggt ttatgggcag gacaaacgga cgaagctgaa     600

atgggtgtta cttatgcgga aatcgacgct tatctgcgcg gcgaaaccgt tagcccgcag     660

gcattgcaac aaatccgttt ctggcacaac cgttctcatc acaaacgtat gttgccacct     720

aaaccgaaat cacccgatga agcggagtgt taa                                  753
```

```
<210> SEQ ID NO 20
<211> LENGTH: 747
<212> TYPE: DNA
<213> ORGANISM: Dichelobacter nodosus VCS1703A

<400> SEQUENCE: 20

atgaccgttc atcaatacat cgattattta ctcgtgtggt tagaagagca gcgcgctcat      60

ctttatgcat cagatggtta tacgttgggc gtcagcggcg gcatcgattc cgccgtttgt     120

ctgcatttac tcgccaaaac gggaaaaccc gtgcaagcgt tagttttgcc gatcaatgcg     180

aacgcgaacg attgtgaaga tgccgaatta gtgttaaaaa atgctaatat ttccggcaat     240

attatcgcgc tcgatgatgt ttataccgcc gcacaaaaca ccttggcgcc tgttttaaat     300

cgcgattatg aacgtatgcc cgtattaaac ggcaatttaa tggcgcggct gcgtatggtt     360

atgctttata ccgtggcgca aagtcatcgt tcggtggtcg tgggaacgga taacgcggtg     420

gaatattatt taggttactt tacaaaattt ggcgacggcg cctgcgatat tttgccgctg     480

gcaaaactga caaaatcaga agtaggacaa ttggcaaaag cgttaggcgt tccgaaaaaa     540

atccgagaaa aagcgccgag cgcaggcttg tggcaagggc aaaccgatga aaacgaaatc     600

ggcgtatcgt acgcggattt agatgctttt ttgtgcggta aaaccgttga tgatgccgtc     660
```

agagaaaaaa ttgcttattg gcatcaacgc tcgcatcata aaagaatgtt gccgccgatg 720
ccggaaatcg gattatcttt ggcgtaa 747

<210> SEQ ID NO 21
<211> LENGTH: 750
<212> TYPE: DNA
<213> ORGANISM: Actinobacillus succinogenes 130Z

<400> SEQUENCE: 21
atgagaacgg cagcatacgt agattattta gtgcgatggc tggaaaccca gcgtaccgaa 60
ttatacggta tggacggcta cacgctgggg gtcagcggcg gtatcgacag tgccgtttgc 120
gcccatttag cggcacgcac cggcgccccc gtacaggcat tgattttacc cgccgaagtc 180
accagccctg aagatgtggc ggatgctcag attaccttgg aaagtgcagg tattgacggg 240
cggattattt ctatcgctcc ttggtacgat ttaattatgc tacaacttac ccccgcatta 300
aatgcggaat ctgaacgcat taacgtattg aaaggtaact taatggcgcg cttacgtatg 360
atcgcattat ttaccacggc gcaaagccac cgttctatcg tattgggtac ggataacgcc 420
gccgaaatgt taacgggcta tttcaccaaa ttcggcgacg gtgcggcgga cgtattgccg 480
ttagcgaggt tgcgcaaaga acaggtattc gaattagggc gttatcttgg cgtaccgaaa 540
tccgtgctgg agaaaaaacc gagtgcgggc ttatgggcgg ggcaaacgga cgagggggaa 600
atgggtgtca gttatgcgga aatcgacgcc tatctgcgcg gcgaaaccgt cagtccgcag 660
gcgttaaagc agattcaatt ctggcacaac cgttctcatc acaaacgtat gctgccgccg 720
acgccagaac cgccggatga aatcgattaa 750

<210> SEQ ID NO 22
<211> LENGTH: 750
<212> TYPE: DNA
<213> ORGANISM: Francisella philomiragia subsp. philomiragia

<400> SEQUENCE: 22
atgaaaataa taaaaaattt tattgcagaa gagtattcta aaaaattaat agaatggtta 60
aaaaaaattt gtataaacta tcctgcagaa ggttttgtta ttggtattag tggtggcata 120
gattcagcag tagcggcatc tttagcggtt aaaactggat tacctacaac agcactaata 180
ctaccatcaa aaaataatca agatcaagat atgaaagatg gactagagct cattaaaaat 240
cttgatatag aacatcatat tgttccaata caacctgctt atgatacatt tatagagtca 300
actcttaact ttacaaactc acaaaatgac cgccaacatg tcatcaaagg taatgctcaa 360
gctcgtctta ggatgatgta tctatatgcc tatgctcaac aaaataacag aattgtaata 420
ggcacagata atgcctgcga atggtatatg ggttatttca caaaatttgg cgatggtgca 480
gcagatatac taccccttgt taatctaaag aaatcacaag tctttgaaat gggcaagtat 540
ctcaaagtgc cgcaaaatat tatagataaa gctccatctg ctggtctatg gcaaggtcaa 600
actgatgaag atgaaatggg tgtcacatat caagaaattg ataacttttt agatggtaaa 660
gaagtctcag ccaaagctct tgagagaata aacttttggc ataatcgtag tcatcacaaa 720
agatctatgg cttttactcc aaacttttaa 750

<210> SEQ ID NO 23
<211> LENGTH: 750
<212> TYPE: DNA
<213> ORGANISM: Francisella cf. novicida 3523

<400> SEQUENCE: 23
atgaaaatag ttaaagattt tagtcctaaa gaatattcac aaaatttagt taattggcta 60
agtgatactt gtataaatta tcctgctgaa ggatttgtaa tcggcattag cggtggtata 120
gattcagctg ttgcagcttc tttagctgtc aaaactggat taccaactac agctttaata 180
ctaccttcaa aaaacaatca acaccaagat atccaagatg ctctagaact tgttgagaaa 240
cttaatattg aacatcatat tgttacaatt caaccagcat acgaaaattt tctagcatca 300
acacaggaat ttataaatac agataataat agacaacttg tgatcaaggg aaatgctcaa 360
gcacgtttaa ggatgatgta tttatatgcc tatgcccaac aatataacag aatagttata 420
ggtactgata atgcttgtga gtggtatatg ggatatttta caaaatttgg tgatggcgct 480
gctgatatat ttccgctaat taatcttaaa aaatcacaag tttttgaatt aggtaaatac 540
ttagatgttc cgaaaaatat aattgataaa gctccgtctg ctggactatg gcaaggacaa 600
actgatgagg atgaaatggg cgtaacttat caagaaattg atgatttctt agatggtaaa 660
caaatttcag caaaagccct agaaagaata aacttctggc ataatcgtag tcatcataag 720
agaaaactag ctttaactcc taatttctaa 750

<210> SEQ ID NO 24
<211> LENGTH: 750
<212> TYPE: DNA
<213> ORGANISM: Francisella sp. TX077308

<400> SEQUENCE: 24
atgaaaatag taaaaaactt tattgtagaa cagtattcta ataatttaat aaaatggtta 60
aaagagaatt gcataaaata tcctgctgaa ggttttgtga ttggtattag tggtggtatc 120
gattcggcag tagccgcatc tttagcagtc aaaacaggat tacctacaac tgctctaata 180
ttgccatcga agaacaatca agaccaagat atgcgagatg gaatagaact aatcgaaaat 240
cttaatatag agtatcatac tgtttcaata caacctgctt atgacacgtt tatagagtca 300
acatttaact ttacaaactc acaaaatgat cgccaacatg ttatcaaagg aaatgcccaa 360
gcgcgtctta gaatgatgta tttatatgct tatgctcagc aaaataatag aattgttata 420
ggtacagata acgcatgtga atggtacatg ggatatttca ctaaatttgg tgatggtgca 480
gcagatatat taccacttat taatctcaaa aaatctcaag tttttgaact aggtaaatac 540
ttaaaagtgc caaaaaacat tatccaaaaa gatccttctg ccggtctatg gcaaggtcaa 600
actgatgagg atgaaatggg tgtcacatac aaagaaattg atgacttctt agacggtaaa 660
gaagtctcag aaaaagctct cgaaagaata agcttctggc ataatcgtag tcaccataaa 720
agatccatgg cttttacccc taatttttaa 750

<210> SEQ ID NO 25
<211> LENGTH: 750
<212> TYPE: DNA
<213> ORGANISM: Francisella sp. FSC1006

<400> SEQUENCE: 25
atgagtgtag taaaaaattt taaacctaat gaatatgcca ataaaattac tgaatggctg 60
aaagactctt gtttaaatta tcccgctgaa ggttttgtgg taggtattag tggaggtata 120
gattcagcag tagcagtctc tttagcagta aatactggac tacctgttac agggctaata 180
atgccatcaa aaaataatga tgataaagat accttagatg ctatagaatt agctaaaaaa 240
ttaaatatag aatatcatct catacccatt caaccagtat atgaaacatt tctagattca 300

-continued

```
gctgaagata tcaaaaacag tgctaatgac cgtcaacatg taatcaaagg aaatgcacaa    360

gctcgtttta gaatgatata cttgtatgct tacgctcagc aaaataatag aatggtaatt    420

ggtacagata atgcttgtga atggtatatg ggctatttta caaaatttgg agatggagcc    480

gctgatatac tgcctcttat aaaattaaaa aaatcacaag tttttgaatt aggtagctat    540

cttaatgtac ccaataacat cctcacaaaa gctccttccg caggactttg gcttggacaa    600

actgatgaag cagagatggg ggtttcatat caagaaatag atgatttcct tgatggtaaa    660

catgtctcag attatgctct taatcaaata aaattctggc ataaccgtag tcatcataaa    720

agaatcatgg ctaaggctcc agatttttaa                                     750
```

<210> SEQ ID NO 26
<211> LENGTH: 753
<212> TYPE: DNA
<213> ORGANISM: Francisella guangzhouensis strain 08HL01032

<400> SEQUENCE: 26

```
atgaacgtag taaaaaattt cactcctgaa aaatattcag aaaaacttat acaatggctc     60

actaatagct gtataaaata tcctgcagaa ggtttcgtaa ttggtgtaag tggtggtata    120

gattctgcag tatgtgcatc acttttatcc aaaactgatc ttcctacaac agcttttata    180

ctaccatcaa aaaataactc tgatcaagat atgatcgatg cattagaact tataaataaa    240

ttaaatattc cataccatat aataccaatc cagccagttt atgaaagttt tctaaagtcc    300

acacagctat ttacaaatcc acaaaatgac agacaaaatg tcataaaagg taacgctcaa    360

gctcgtttta gaatgatgta tttatatgct tatgcacaac aaaataatcg tatagtagtt    420

ggaacagata atgcttgtga atggtatatg ggttatttca ccaaatttgg cgatggagct    480

gctgatatac taccattaat aaatcttaaa aagtcccagg tatttgagtt aggtaaatac    540

ttagatgttc caaggaatat cctaactaag gcaccctctg ctggtctttg gcaaggccaa    600

actgatgaag gtgaaatggg agttacttat caggaaatag ataattttct cgacggtaaa    660

gaagtatcgc cagcaacttt tgaaaaaata agctactggc ataatcgctc tcaccacaaa    720

agaaagatgg ctttaacgcc agattttaac taa                                 753
```

<210> SEQ ID NO 27
<211> LENGTH: 750
<212> TYPE: DNA
<213> ORGANISM: Francisella persica ATCC VR-331

<400> SEQUENCE: 27

```
atgaaaatag ttaaagattt caacatcaaa gaatattcac aaaagttaat tgattggcta     60

agtgatactt gtatgaatta ccctgctgaa ggatttgtca ttggtcttag cggtggtata    120

gattcggcag ttgcagcttc tttagctgtc aaaactggat tatcaactac agctttaata    180

ttaccatcaa aaaacaatca acaccaagat atacaagatg ctctagaact tgcagataaa    240

attaatattg aacatcatac tattacaatt caaacagtat acgaaacttt tcttgcgtca    300

ataaaaaaaa ttacaaatac cgaacgtgat agacaacttg tcattaaagg aaatgctcaa    360

gctcgtttga ggatgatgta tttatatgcc tatgctcaac aatataatag agtggttatt    420

ggtactgata atgcttgtga atggtatatg ggatatttta caaagtttgg tgatggtgct    480

gctgatattc ttccactagt taatctcaaa aaatctcacg tttttgaatt aggtaaatac    540

ttaggtgttc ctaaaaatat acttgataaa gctccatctg ctgggctatg gcaaggacaa    600

actgatgaag atgaaatggg cgtaacttat caagaaattg atgatttctt agatggtaag    660
```

-continued

```
caagtttcag cgaaagctct agaaagaata aatttctggc ataatcgtag tcatcataag    720

agaaaactag ctttaattcc taatttctaa                                     750
```

<210> SEQ ID NO 28
<211> LENGTH: 753
<212> TYPE: DNA
<213> ORGANISM: Mannheimia succiniciproducens

<400> SEQUENCE: 28

```
atgaaaacgg cagcatacgc agattatctg attcaatggc tggaaaacca acgcaccgaa     60

ctgtacggca tggacggcta taccctgggc gtcagcggcg gtattgacag cgccgtctgc    120

gctcatctgg cagcgcgcac cggcgcgccg gtacaagccc tgattctgcc ggcggaagta    180

accagtccgt cagatgtggc ggatgcgcaa gccaccctgg aaagcgccgg tattgacggc    240

caaattattt ccattgcacc gtggtacgat ctgattatgc aacaactgtc cccggtactg    300

aatagcgaac cggagcgcgt taacgtactg aaaggtaatc tgatggcacg cctgcgtatg    360

attgcgctgt ttaccacggc acaaagccat cgttctattg tgctgggcac cgataatgcg    420

gcggaatggc tgacgggtta ttttaccaaa ttcggcgacg gcgcagcgga cgtactgccg    480

ctggcgggcc tgcgcaaaga gcaggtattt gaactgggcc gttatctggg cgtaccgcaa    540

agcgtgctgg ataaaaaacc gagcgccggt ctgtgggcag gccaaacgga cgaagctgaa    600

atgggtgtta cctatgcgga aatcgacgct tatctgcgcg gcgaaaccgt tagcccgcag    660

gcactgcaac aaatccgttt ctggcacaac cgttctcatc acaaacgtat gctgccgccg    720

aaaccgaaat caccggatga agcggagtgt taa                                 753
```

<210> SEQ ID NO 29
<211> LENGTH: 747
<212> TYPE: DNA
<213> ORGANISM: Dichelobacter nodosus VCS1703A

<400> SEQUENCE: 29

```
atgaccgttc atcaatacat tgattatctg ctggtgtggc tggaagagca gcgcgctcat     60

ctgtatgcat cagatggtta tacgctgggc gtcagcggcg gcattgattc cgccgtttgt    120

ctgcatctgc tggccaaaac gggcaaacca gtgcaagcgc tggttctgcc gatcaatgcg    180

aacgcgaacg attgtgaaga tgccgaactg gtgctgaaaa atgctaatat ttccggcaat    240

attatcgcgc tggatgatgt ttataccgcc gcacaaaaca ccctggcgcc ggttctgaat    300

cgcgattatg aacgtatgcc ggtactgaac ggcaatctga tggcgcgcct gcgtatggtt    360

atgctgtata ccgtggcgca aagtcatcgt tcggtggtcg tgggcacgga taacgcggtg    420

gaatattatc tgggttactt taccaaattt ggcgacggcg cctgcgatat tctgccgctg    480

gcaaaactga ccaaatcaga agtaggccaa ctggcaaaag cgctgggcgt tccgaaaaaa    540

atccgcgaaa aagcgccgag cgcgggcctg tggcaaggcc aaaccgatga aaacgaaatc    600

ggcgtatcgt acgcggatct ggatgctttt ctgtgcggta aaaccgttga tgatgccgtc    660

cgcgaaaaaa ttgcttattg gcatcaacgc tcgcatcata aacgtatgct gccgccgatg    720

ccggaaatcg gcctgtctct ggcgtaa                                        747
```

<210> SEQ ID NO 30
<211> LENGTH: 750
<212> TYPE: DNA
<213> ORGANISM: Actinobacillus succinogenes 130Z

<400> SEQUENCE: 30
atgcgcacgg cagcatacgt agattatctg gtgcgctggc tggaaaccca gcgtaccgaa 60
ctgtacggta tggacggcta cacgctgggc gtcagcggcg gtatcgacag tgccgtttgc 120
gcccatctgg cggcacgcac cggcgccccg gtacaggcac tgattctgcc ggcggaagtc 180
accagcccgg aagatgtggc ggatgctcag attaccctgg aaagtgcagg tattgatggc 240
cgcattattt ctatcgctcc gtggtacgat ctgattatgc tgcaactgac cccggcactg 300
aatgcggaat ctgaacgcat taacgtactg aaaggtaacc tgatggcgcg cctgcgtatg 360
atcgcactgt ttaccacggc gcaaagccac cgttctatcg tactgggtac ggataacgcc 420
gccgaaatgc tgacgggcta tttcaccaaa ttcggcgacg gtgcggcgga cgtactgccg 480
ctggcgcgcc tgcgcaaaga acaggtattc gaactgggcc gttatctggg cgtaccgaaa 540
tccgtgctgg agaaaaaacc gagtgcgggc ctgtgggcgg gccaaacgga cgagggcgaa 600
atgggtgtca gttatgcgga aatcgacgcc tatctgcgcg gcgaaaccgt cagtccgcag 660
gcgctgaaac agattcaatt ctggcacaac cgttctcatc acaaacgtat gctgccgccg 720
acgccggaac cgccggatga aattgattaa 750

<210> SEQ ID NO 31
<211> LENGTH: 750
<212> TYPE: DNA
<213> ORGANISM: Francisella philomiragia subsp. philomiragia

<400> SEQUENCE: 31
atgaaaatta ttaaaaattt tattgcagaa gagtattcta aaaaactgat tgaatggctg 60
aaaaaaattt gtattaacta tccggcagaa ggttttgtta ttggtattag tggtggcatt 120
gattcagcag tagcggcatc tctggcggtt aaaaccggcc tgccgaccac cgcactgatt 180
ctgccgtcaa aaaataatca agatcaagat atgaaagatg gcctggagct gattaaaaat 240
ctggatattg aacatcatat tgttccgatt caaccggctt atgatacctt tattgagtca 300
accctgaact ttaccaactc acaaaatgac cgccaacatg tcatcaaagg taatgctcaa 360
gctcgtctgc gcatgatgta tctgtatgcc tatgctcaac aaaataaccg cattgtaatt 420
ggcaccgata atgcctgcga atggtatatg ggttatttca ccaaatttgg cgatggtgca 480
gcagatattc tgccgctggt taatctgaaa aaatcacaag tctttgaaat gggcaaatat 540
ctgaaagtgc cgcaaaatat tattgataaa gctccgtctg ctggtctgtg gcaaggtcaa 600
accgatgaag atgaaatggg tgtcacctat caagaaattg ataactttct ggatggtaaa 660
gaagtctcag ccaaagctct ggagcgcatt aacttttggc ataatcgtag tcatcacaaa 720
cgctctatgg cttttacccc gaacttttaa 750

<210> SEQ ID NO 32
<211> LENGTH: 750
<212> TYPE: DNA
<213> ORGANISM: Francisella cf. novicida 3523

<400> SEQUENCE: 32
atgaaaattg ttaaagattt tagtccgaaa gaatattcac aaaatctggt taattggctg 60
agtgatacct gtattaatta tccggctgaa ggctttgtaa tcggcattag cggtggtatt 120
gattcagcgg ttgcagcttc tctggctgtc aaaaccggcc tgccgaccac cgctctgatt 180
ctgccgtcaa aaaacaatca acaccaagat attcaagatg ctctggaact ggttgagaaa 240
ctgaatattg aacatcatat tgttaccatt caaccggcat acgaaaattt tctggcatca 300
acccaggaat ttattaatac cgataataat cgccaactgg tgatcaaagg caatgctcaa 360
gcacgtctgc gcatgatgta tctgtatgcc tatgcccaac aatataaccg cattgttatt 420
ggtaccgata atgcttgtga gtggtatatg ggctatttta ccaaatttgg tgatggcgct 480
gctgatattt ttccgctgat taatctgaaa aaatcacaag tttttgaact gggtaaatac 540
ctggatgttc cgaaaaatat tattgataaa gctccgtctg ctggcctgtg gcaaggccaa 600
accgatgagg atgaaatggg cgtaacctat caagaaattg atgatttcct ggatggtaaa 660
caaatttcag caaaagccct ggaacgcatt aacttctggc ataatcgtag tcatcataaa 720
cgcaaactgg ctctgacccc gaatttctaa 750

<210> SEQ ID NO 33
<211> LENGTH: 750
<212> TYPE: DNA
<213> ORGANISM: Francisella sp. TX077308

<400> SEQUENCE: 33
atgaaaattg taaaaaactt tattgtagaa cagtattcta ataatctgat taaatggctg 60
aaagagaatt gcattaaata tccggctgaa ggttttgtga ttggtattag tggtggtatt 120
gattcggcag tagccgcatc tctggcagtc aaaaccggcc tgccgaccac cgctctgatt 180
ctgccgtcga aaaacaatca agaccaagat atgcgcgatg gcattgaact gatcgaaaat 240
ctgaatattg agtatcatac cgtttcaatt caaccggctt atgacacgtt tattgagtca 300
acctttaact ttaccaactc acaaaatgat cgccaacatg ttatcaaagg caatgcccaa 360
gcgcgtctgc gcatgatgta tctgtatgct tatgctcagc aaaataatcg cattgttatt 420
ggtaccgata acgcatgtga atggtacatg ggctatttca ccaaatttgg tgatggtgca 480
gcagatattc tgccgctgat taatctgaaa aaatctcaag tttttgaact gggtaaatac 540
ctgaaagtgc cgaaaaacat tatccaaaaa gatccgtctg ccggtctgtg gcaaggtcaa 600
accgatgagg atgaaatggg tgtcacctac aaagaaattg atgacttcct ggacggtaaa 660
gaagtctcag aaaaagctct ggaacgcatt agcttctggc ataatcgtag tcaccataaa 720
cgcagcatgg cttttacccc gaatttttaa 750

<210> SEQ ID NO 34
<211> LENGTH: 750
<212> TYPE: DNA
<213> ORGANISM: Francisella sp. FSC

<400> SEQUENCE: 34
atgagtgtag taaaaaattt taaaccgaat gaatatgcca ataaaattac cgaatggctg 60
aaagactctt gtctgaatta tccggctgaa ggttttgtgg taggtattag tggcggtatt 120
gattcagcag tagcagtctc tctggcagta aataccggcc tgccggttac cggcctgatt 180
atgccgtcaa aaaataatga tgataaagat accctggatg ctattgaact ggctaaaaaa 240
ctgaatattg aatatcatct gattccgatt cagccggtat atgaaacctt tctggattca 300
gcggaagata ttaaaaacag tgctaatgac cgtcaacatg taatcaaagg caatgcacaa 360
gctcgttttc gcatgattta cctgtatgct tacgctcagc aaaataatcg catggtaatt 420
ggtaccgata atgcttgtga atggtatatg ggctatttta ccaaatttgg cgatggcgcc 480
gctgatattc tgccgctgat taaactgaaa aaatcacaag tttttgaact gggtagctat 540
ctgaatgtac cgaataacat cctgaccaaa gctccgagcg cgggcctgtg gctgggccaa 600
accgatgaag cagagatggg cgtttcatat caagaaattg atgatttcct ggatggtaaa 660
catgtctcag attatgctct gaatcaaatt aaattctggc ataaccgtag tcatcataaa 720
cgcatcatgg ctaaagctcc ggatttttaa 750

<210> SEQ ID NO 35
<211> LENGTH: 753
<212> TYPE: DNA
<213> ORGANISM: Francisella guangzhouensis strain 08HL01032

<400> SEQUENCE: 35
atgaacgtag taaaaaattt caccccggaa aaatattcag aaaaactgat tcaatggctg 60
accaatagct gtattaaata tccggcagaa ggtttcgtaa ttggtgtaag tggtggtatt 120
gattctgcgg tatgtgcatc actgctgtcc aaaaccgatc tgccgaccac cgcttttatt 180
ctgccgtcaa aaaataactc tgatcaagat atgattgatg cactggaact gattaataaa 240
ctgaatattc cgtaccatat tattccgatc cagccggttt atgaaagttt tctgaaatcc 300
acccaactgt ttaccaatcc gcaaaatgac cgccaaaatg tcattaaagg taacgctcaa 360
gctcgttttc gcatgatgta tctgtatgct tatgcacaac aaaataatcg tattgtagtt 420
ggcaccgata atgcttgtga atggtatatg ggttatttca ccaaatttgg cgatggcgct 480
gctgatattc tgccgctgat taatctgaaa aaatcccagg tatttgagct gggtaaatac 540
ctggatgttc cgcgcaatat cctgaccaaa gcaccgtctg ctggtctgtg gcaaggccaa 600
accgatgaag gtgaaatggg cgttacctat caggaaattg ataattttct ggacggtaaa 660
gaagtatcgc cggcaacctt tgaaaaaatt agctactggc ataatcgctc tcaccacaaa 720
cgcaaaatgg ctctgacgcc ggattttaac taa 753

<210> SEQ ID NO 36
<211> LENGTH: 750
<212> TYPE: DNA
<213> ORGANISM: Francisella persica ATCC VR-331

<400> SEQUENCE: 36
atgaaaattg ttaaagattt caacatcaaa gaatattcac aaaaactgat tgattggctg 60
agtgatacct gtatgaatta cccggctgaa ggctttgtca ttggtctgag cggtggtatt 120
gattcggcag ttgcagcttc tctggctgtc aaaaccggcc tgtcaaccac cgctctgatt 180
ctgccgtcaa aaaacaatca acaccaagat attcaagatg ctctggaact ggcagataaa 240
attaatattg aacatcatac cattaccatt caaaccgtat acgaaacctt tctggcgtca 300
attaaaaaaa ttaccaatac cgaacgtgat cgccaactgg tcattaaagg caatgctcaa 360
gctcgtctgc gcatgatgta tctgtatgcc tatgctcaac aatataatcg cgtggttatt 420
ggtaccgata atgcttgtga atggtatatg ggctatttta ccaaatttgg tgatggtgct 480
gctgatattc tgccgctggt taatctgaaa aaatctcacg tttttgaact gggtaaatac 540
ctgggtgttc cgaaaaatat tctggataaa gctccgtctg ctggcctgtg gcaaggccaa 600
accgatgaag atgaaatggg cgtaacctat caagaaattg atgatttcct ggatggtaaa 660
caagtttcag cgaaagctct ggaacgcatt aatttctggc ataatcgtag tcatcataaa 720
cgcaaactgg ctctgattcc gaatttctaa 750

<210> SEQ ID NO 37
<211> LENGTH: 750
<212> TYPE: DNA
<213> ORGANISM: FtNadE_star_optimized

<400> SEQUENCE: 37
atgaaaatcg tcaaagactt ctccccgaaa gaatattccc aaaaactggt gaactggctg 60
agcgactcgt gtatgaacta tccggcagaa ggctttgtca ttggtctgag tggcggtatc 120
gattccgctg tggcggcctc actggccgtt aaaaccggcc tgccgaccac ggcactgatt 180
ctgccgtctg acaacaatca gcatcaagat atgcaggacg cgctggaact gattgaaatg 240
ctgaacatcg aacactacac catttccatc cagccggcgt atgaagcgtt tctggcgagc 300
acccaatctt tcacgaacct gcagaacaat cgtcaactgg tgatcaaagg caatgcgcag 360
gcccgtctgc gcatgatgta tctgtacgcg tatgcgcagc aatacaaccg cattgttatc 420
ggcaccgata atgcctgcga atggtacatg ggttatttta cgaaattcgg cgatggtgca 480
gctgacattc tgccgctggt caacctgaaa aaatcgcagg tgtttgaact gggtaaatac 540
ctggatgttc cgaaaaatat cctggacaaa gcaccgagcg caggtctgtg gcagggtcaa 600
accgatgaag acgaaatggg cgttacgtat caggaaattg atgacttcct ggatggtaaa 660
caagtcagcg cgaaagccct ggaacgtatc aacttctggc acaaccgctc acatcataaa 720
cgcaaactgg cactgacccc gaacttctaa 750

<210> SEQ ID NO 38
<211> LENGTH: 782
<212> TYPE: DNA
<213> ORGANISM: Optimized_FtNadE_star_Bacillus

<400> SEQUENCE: 38
gctacctgag aagcttatga aaatcgttaa agacttctct ccgaaagaat attctcaaaa 60
acttgtgaac tggcttagcg actcttgtat gaactatccg gcagaaggct ttgttattgg 120
tctttctggc ggtatcgact ctgctgtggc ggcttcactt gctgttaaaa caggtcttcc 180
gacaacagca cttattcttc cgtctgacaa caatcagcat caagatatgc aggacgcgct 240
tgaacttatt gaaatgctta acatcgaaca ctacacaatt tctatccagc cggcgtatga 300
agcgtttctt gcgagcacac aatctttcac aaaccttcag aacaatcgtc aacttgtgat 360
caaaggcaat gcgcaggctc gtcttcgcat gatgtatctt tacgcgtatg cgcagcaata 420
caaccgcatt gttatcggca cagataatgc ttgcgaatgg tacatgggtt attttacaaa 480
attcggcgat ggtgctgctg acattcttcc gcttgttaac cttaaaaaat ctcaggtgtt 540
tgaacttggt aaataccttg atgttccgaa aaatatcctt gacaaagcac cgagcgcagg 600
tctttggcag ggtcaaacag atgaagacga aatgggcgtt acatatcagg aaattgatga 660
cttccttgat ggtaaacaag ttagcgcgaa agctcttgaa cgtatcaact tctggcacaa 720
ccgctcacat cataaacgca aacttgcact tacaccgaac ttctaagcat gcagtaagta 780
gc 782

<210> SEQ ID NO 39
<211> LENGTH: 785
<212> TYPE: DNA
<213> ORGANISM: Optimized_AE016827_Bacillus Mannheimia
succiniciproducens MBEL55E

<400> SEQUENCE: 39
gctacctgag aagcttatga aaacagcagc atacgcagat tatcttattc aatggcttga 60
aaaccaacgc acagaacttt acggcatgga cggctataca cttggcgtta gcggcggtat 120
tgacagcgct gtttgcgctc atcttgcagc gcgcacaggc gcgccggtac aagctcttat 180

```
tcttccggcg gaagtaacat ctccgtcaga tgtggcggat gcgcaagcta cacttgaaag    240

cgctggtatt gacggccaaa ttatttctat tgcaccgtgg tacgatctta ttatgcaaca    300

actttctccg gtacttaata gcgaaccgga acgcgttaac gtacttaaag gtaatcttat    360

ggcacgcctt cgtatgattg cgctttttac aacagcacaa agccatcgtt ctattgtgct    420

tggcacagat aatgcggcgg aatggcttac aggttatttt acaaaattcg gcgacggcgc    480

agcggacgta cttccgcttg cgggccttcg caaagaacag gtatttgaac ttggccgtta    540

tcttggcgta ccgcaaagcg tgcttgataa aaaaccgagc gctggtcttt gggcaggcca    600

aacagacgaa gctgaaatgg gtgttacata cgcggaaatc gacgcttatc ttcgcggcga    660

aacagttagc ccgcaggcac ttcaacaaat ccgtttctgg cacaaccgtt ctcatcacaa    720

acgtatgctt ccgccgaaac cgaaatcacc ggatgaagcg gaatgttaag catgcagtaa    780

gtagc                                                                785
```

<210> SEQ ID NO 40
<211> LENGTH: 782
<212> TYPE: DNA
<213> ORGANISM: Optimized_CP002558_Bacillus Francisella cf. novicida
      3523

<400> SEQUENCE: 40

```
gctacctgag aagcttatga aaattgttaa agatttttct ccgaaagaat attcacaaaa     60

tcttgttaat tggctttctg atacatgtat taattatccg gctgaaggct ttgtaatcgg    120

cattagcggt ggtattgatt cagcggttgc agcttctctt gctgttaaaa caggccttcc    180

gacaacagct cttattcttc cgtcaaaaaa caatcaacac caagatattc aagatgctct    240

tgaacttgtt gaaaaactta atattgaaca tcatattgtt acaattcaac cggcatacga    300

aaatttttctt gcatcaacac aggaatttat taatacagat aataatcgcc aacttgtgat    360

caaaggcaat gctcaagcac gtcttcgcat gatgtatctt tatgcttatg ctcaacaata    420

taaccgcatt gttattggta cagataatgc ttgtgaatgg tatatgggct attttacaaa    480

atttggtgat ggcgctgctg atatttttcc gcttattaat cttaaaaaat cacaagtttt    540

tgaacttggt aaataccttg atgttccgaa aaatattatt gataaagctc cgtctgctgg    600

cctttggcaa ggccaaacag atgaagatga aatgggcgta acatatcaag aaattgatga    660

tttccttgat ggtaaacaaa tttcagcaaa agctcttgaa cgcattaact tctggcataa    720

tcgttctcat cataaacgca aacttgctct tacaccgaat ttctaagcat gcagtaagta    780

gc                                                                   782
```

<210> SEQ ID NO 41
<211> LENGTH: 782
<212> TYPE: DNA
<213> ORGANISM: Optimized_CP002872_Bacillus Francisella sp. TX077308

<400> SEQUENCE: 41

```
gctacctgag aagcttatga aaattgtaaa aaactttatt gtagaacagt attctaataa     60

tcttattaaa tggcttaaag aaaattgcat taaatatccg gctgaaggtt ttgtgattgg    120

tatttctggt ggtattgatt ctgcagtagc tgcatctctt gcagttaaaa caggccttcc    180

gacaacagct cttattcttc cgtctaaaaa caatcaagac caagatatgc gcgatggcat    240

tgaacttatc gaaaatctta atattgaata tcatacagtt tcaattcaac cggcttatga    300

cacatttatt gaatcaacat ttaactttac aaactcacaa aatgatcgcc aacatgttat    360
```

-continued caaaggcaat gctcaagcgc gtcttcgcat gatgtatctt tatgcttatg ctcagcaaaa 420
taatcgcatt gttattggta cagataacgc atgtgaatgg tacatgggct atttcacaaa 480
atttggtgat ggtgcagcag atattcttcc gcttattaat cttaaaaaat ctcaagtttt 540
tgaacttggt aaatacctta aagtgccgaa aaacattatc caaaaagatc cgtctgctgg 600
tctttggcaa ggtcaaacag atgaagatga aatgggtgtt acatacaaag aaattgatga 660
cttccttgac ggtaaagaag tttcagaaaa agctcttgaa cgcattagct tctggcataa 720
tcgttctcac cataaacgca gcatggcttt tacaccgaat ttttaagcat gcagtaagta 780
gc 782

<210> SEQ ID NO 42
<211> LENGTH: 750
<212> TYPE: DNA
<213> ORGANISM: Reverted FtNadE_star

<400> SEQUENCE: 42
atgaaaatcg tcaaagactt ctccccgaaa gaatattccc aaaaactggt gaactggctg 60
agcgactcgt gtatgaacac tccggcagaa ggctttgtca ttggtctgag tggcggtatc 120
gattccgctg tggcggcctc actggccgtt aaaaccggcc tgccgaccac ggcactgatt 180
ctgccgtctg acaacaatca gcatcaagat atgcaggacg cgctggaact gattgaaatg 240
ctgaacatcg aacactacac catttccatc cagccggcgt atgaagcgtt tctggcgagc 300
acccaatctt tcacgaacct gcagaacaat cgtcaactgg tgatcaaagg caatgcgcag 360
gcccgtctgc gcatgatgta tctgtacgcg tatgcgggtc aatacaaccg cattgttatc 420
ggcaccgata atgcctgcga atggtacatg ggttatttta cgaaattcgg cgatggtgca 480
gctgacattc tgccgctggt caacctgaaa aaatcgcagg tgtttgaact gggtaaatac 540
ctggatgttc cgaaaaatat cctggacaaa gcaccgagcg caggtctgtg gcagggtcaa 600
accgatgaag acgaaatggg cgttacgtat caggaaattg atgacttcct ggatggtaaa 660
caagtcagcg cgaaagccct ggaacgtatc aacttctggc acaacgtctc acatcataaa 720
cgcaaactgg cactgacccc gaacttctaa 750

<210> SEQ ID NO 43
<211> LENGTH: 753
<212> TYPE: DNA
<213> ORGANISM: Optimized_AE016827_Reverted Mannheimia
succiniciproducens MBEL55E

<400> SEQUENCE: 43
atgaaaacgg cagcatacgc agattatctg attcaatggc tggaaaacca acgcaccgaa 60
ctgaccggca tggacggcta taccctgggc gtcagcggcg gtattgacag cgccgtctgc 120
gctcatctgg cagcgcgcac cggcgcgccg gtacaagccc tgattctgcc ggcggaagta 180
accagtccgt cagatgtggc ggatgcgcaa gccaccctgg aaagcgccgg tattgacggc 240
caaattattt ccattgcacc gtggtacgat ctgattatgc aacaactgtc cccggtactg 300
aatagcgaac cggagcgcgt taacgtactg aaaggtaatc tgatggcacg cctgcgtatg 360
attgcgctgt ttaccacggc aggcagccat cgttctattg tgctgggcac cgataatgcg 420
gcggaatggc tgacgggtta ttttaccaaa ttcggcgacg gcgcagcgga cgtactgccg 480
ctggcgggcc tgcgcaaaga gcaggtattt gaactgggcc gttatctggg cgtaccgcaa 540
agcgtgctgg ataaaaaacc gagcgccggt ctgtgggcag gccaaacgga cgaagctgaa 600

-continued atgggtgtta cctatgcgga aatcgacgct tatctgcgcg gcgaaaccgt tagcccgcag 660
gcactgcaac aaatccgttt ctggcacaac gtttctcatc acaaacgtat gctgccgccg 720
aaaccgaaat caccggatga agcggagtgt taa 753

<210> SEQ ID NO 44
<211> LENGTH: 750
<212> TYPE: DNA
<213> ORGANISM: Optimized_CP002558_Reverted Francisella cf. novicida 3523

<400> SEQUENCE: 44
atgaaaattg ttaaagattt tagtccgaaa gaatattcac aaaatctggt taattggctg 60
agtgatacct gtattaatac tccggctgaa ggctttgtaa tcggcattag cggtggtatt 120
gattcagcgg ttgcagcttc tctggctgtc aaaaccggcc tgccgaccac cgctctgatt 180
ctgccgtcaa aaaacaatca acaccaagat attcaagatg ctctggaact ggttgagaaa 240
ctgaatattg aacatcatat tgttaccatt caaccggcat acgaaaattt tctggcatca 300
acccaggaat ttattaatac cgataataat cgccaactgg tgatcaaagg caatgctcaa 360
gcacgtctgc gcatgatgta tctgtatgcc tatgccggcc aatataaccg cattgttatt 420
ggtaccgata atgcttgtga gtggtatatg ggctatttta ccaaatttgg tgatggcgct 480
gctgatattt ttccgctgat taatctgaaa aaatcacaag tttttgaact gggtaaatac 540
ctggatgttc cgaaaaatat tattgataaa gctccgtctg ctggcctgtg gcaaggccaa 600
accgatgagg atgaaatggg cgtaacctat caagaaattg atgatttcct ggatggtaaa 660
caaatttcag caaaagccct ggaacgcatt aacttctggc ataatgttag tcatcataaa 720
cgcaaactgg ctctgacccc gaatttctaa 750

<210> SEQ ID NO 45
<211> LENGTH: 750
<212> TYPE: DNA
<213> ORGANISM: Optimized_CP002872_Reverted Francisella sp. TX077308

<400> SEQUENCE: 45
atgaaaattg taaaaaactt tattgtagaa cagtattcta ataatctgat taaatggctg 60
aaagagaatt gcattaaaac tccggctgaa ggttttgtga ttggtattag tggtggtatt 120
gattcggcag tagccgcatc tctggcagtc aaaaccggcc tgccgaccac cgctctgatt 180
ctgccgtcga aaaacaatca agaccaagat atgcgcgatg gcattgaact gatcgaaaat 240
ctgaatattg agtatcatac cgtttcaatt caaccggctt atgacacgtt tattgagtca 300
acctttaact ttaccaactc acaaaatgat cgccaacatg ttatcaaagg caatgcccaa 360
gcgcgtctgc gcatgatgta tctgtatgct tatgctgggc aaaataatcg cattgttatt 420
ggtaccgata acgcatgtga atggtacatg ggctatttca ccaaatttgg tgatggtgca 480
gcagatattc tgccgctgat taatctgaaa aaatctcaag tttttgaact gggtaaatac 540
ctgaaagtgc cgaaaaacat tatccaaaaa gatccgtctg ccggtctgtg gcaaggtcaa 600
accgatgagg atgaaatggg tgtcacctac aaagaaattg atgacttcct ggacggtaaa 660
gaagtctcag aaaaagctct ggaacgcatt agcttctggc ataatgttag tcaccataaa 720
cgcagcatgg cttttacccc gaatttttaa 750

<210> SEQ ID NO 46
<211> LENGTH: 828

<212> TYPE: DNA
<213> ORGANISM: Escherichia coli

<400> SEQUENCE: 46
atgacattgc aacaacaaat aataaaggcg ctgggcgcaa aaccgcagat taatgccgaa 60
gaggaaattc gtcgtagtgt cgattttctg aaaagctacc tgcgaactta tccgttcatt 120
aaatcactgg tgctcgggat cagcggcggt caggactcca cgcttgccgg aaagctgtgc 180
cagatggcga ttaatgagct gcgccaggaa accggcaacg aatcactgca atttattgcc 240
gtacgcctgc cctatggtgt tcaggccgac gaacaagatt gccaggatgc cattgccttt 300
attcaaccgg atcgcgtatt aaccgttaat atcaagggcg cggtattggc tagcgagcag 360
gcattgcggg aagcaggcat tgaactgagc gattttgtcc gtggcaatga aaaagcgcgt 420
gagcggatga aagcacaata tagcattgcg ggtatgacca gcggtgtcgt ggtgggcacc 480
gatcatgcag cagaagccat taccggattc ttcactaaat atggtgacgg cggtacggat 540
attaatccgc tgtatcgtct caacaaacgt cagggtaaac agttactggc ggcattaggt 600
tgcccggaac acctttataa gaaagcgcca acggccgatc tggaagatga tcgcccttct 660
ctgccagatg aagtggcact cggcgtgacc tatgacaata tcgacgacta tctggaaggg 720
aaaaacgtac ctcaacaggt cgccagaaca atagagaact ggtatctgaa aaccgaacat 780
aaacgccgtc cgccaattac cgttttcgat gatttctgga aaaagtaa 828

<210> SEQ ID NO 47
<211> LENGTH: 789
<212> TYPE: DNA
<213> ORGANISM: Optimized_CP002558_Corynebacterium Francisella cf. novicida 3523

<400> SEQUENCE: 47
cagagaattc aaaggaggac aaccatggat gaaaattgtg aaagattttt ccccaaaaga 60
atattcccaa aatctggtga attggctgtc cgatacctgt attaattatc cagcagaagg 120
ctttgtgatc ggcatttccg gtggtattga ttccgcagtg gcagcatccc tggcagtgaa 180
aaccggcctg ccaaccaccg cactgattct gccatccaaa aacaatcaac accaagatat 240
tcaagatgca ctggaactgg tggaaaaact gaatattgaa catcatattg tgaccattca 300
accagcatac gaaaatttc tggcatccac ccaggaattt attaataccg ataataatcg 360
ccaactggtg atcaaaggca atgcacaagc acgcctgcgc atgatgtatc tgtatgcata 420
tgcacaacaa tataaccgca ttgtgattgg caccgataat gcatgtgaat ggtatatggg 480
ctattttacc aaatttggtg atggcgcagc agatattttt ccactgatta atctgaaaaa 540
atcccaagtg tttgaactgg gtaaatacct ggatgtgcca aaaaatatta ttgataaagc 600
accatccgca ggcctgtggc aaggccaaac cgatgaagat gaaatgggcg tgacctatca 660
agaaattgat gatttcctgg atggtaaaca aatttccgca aaagcactgg aacgcattaa 720
cttctggcat aatcgctccc atcataaacg caaactggca ctgaccccaa atttctaagg 780
tacccgggg 789

<210> SEQ ID NO 48
<211> LENGTH: 1611
<212> TYPE: DNA
<213> ORGANISM: B. subtilis Tetracyclin cassette 1611bp

<400> SEQUENCE: 48
aaagagtagt tcaacaaacg ggccatattg ttgtataagt gatgaaatac tgaatttaaa 60

```
acttagttta tatgtggtaa aatgttttaa tcaagtttag gaggaattaa ttatgaagtg    120
taatgaatgt aacagggttc aattaaaaga gggaagcgta tcattaaccc tataaactac    180
gtctgccctc attattggag ggtgaaatgt gaatacatcc tattcacaat cgaatttacg    240
acacaaccaa attttaattt ggctttgcat tttatctttt tttagcgtat taaatgaaat    300
ggttttgaac gtctcattac ctgatattgc aaatgatttt aataaaccac ctgcgagtac    360
aaactgggtg aacacagcct ttatgttaac cttttccatt ggaacagctg tatatggaaa    420
gctatctgat caattaggca tcaaaaggtt actcctattt ggaattataa taaattgttt    480
cgggtcggta attgggtttg ttggccattc tttcttttcc ttacttatta tggctcgttt    540
tattcaaggg gctggtgcag ctgcatttcc agcactcgta atggttgtag ttgcgcgcta    600
tattccaaag gaaaataggg gtaaagcatt tggtcttatt ggatcgatag tagccatggg    660
agaaggagtc ggtccagcga ttggtggaat gatagcccat tatattcatt ggtcctatct    720
tctactcatt cctatgataa caattatcac tgttccgttt cttatgaaat tattaaagaa    780
agaagtaagg ataaaaggtc attttgatat caaaggaatt atactaatgt ctgtaggcat    840
tgtatttttt atgttgttta caacatcata tagcatttct tttcttatcg ttagcgtgct    900
gtcattcctg atatttgtaa aacatatcag gaaagtaaca gatccttttg ttgatcccgg    960
attagggaaa aatatacctt ttatgattgg agttctttgt gggggaatta tatttggaac   1020
agtagcaggg tttgtctcta tggttcctta tatgatgaaa gatgttcacc agctaagtac   1080
tgccgaaatc ggaagtgtaa ttattttccc tggaacaatg agtgtcatta ttttcggcta   1140
cattggtggg atacttgttg atagaagagg tcctttatac gtgttaaaca tcggagttac   1200
atttcttttct gttagctttt taactgcttc ctttctttta gaaacaacat catggttcat   1260
gacaattata atcgtatttg ttttaggtgg gctttcgttc accaaaacag ttatatcaac   1320
aattgtttca agtagcttga aacagcagga agctggtgct ggaatgagtt tgcttaactt   1380
taccagcttt ttatcagagg gaacaggtat tgcaattgta ggtggtttat tatccatacc   1440
cttacttgat caaaggttgt tacctatgga agttgatcag tcaacttatc tgtatagtaa   1500
tttgttatta ctttttttcag gaatcattgt cattagttgg ctggttacct tgaatgtata   1560
taaacattct caaagggatt tctaaatcgt taagggatca actttgggag a            1611
```

```
<210> SEQ ID NO 49
<211> LENGTH: 1430
<212> TYPE: DNA
<213> ORGANISM: B. subtilis Neomycin cassette 1430bp

<400> SEQUENCE: 49

gcttgggctg caggtcgaga tcagggaatg agtttataaa ataaaaaaag cacctgaaaa     60
ggtgtctttt tttgatggtt ttgaacttgt tctttcttat cttgatacat atagaaataa    120
cgtcattttt attttagttg ctgaaaggtg cgttgaagtg ttggtatgta tgtgttttaa    180
agtattgaaa acccttaaaa ttggttgcac agaaaaaccc catctgttaa agttataagt    240
gactaaacaa ataactaaat agatgggggt ttcttttaat attatgtgtc ctaatagtag    300
catttattca gatgaaaaat caagggtttt agtggacaag acaaaaaagtg gaaaagtgag   360
accatgtgct taggaagacg agttattaat agctgaataa gaacggtgct ctccaaatat    420
tcttatttag aaaagcaaat ctaaaattat ctgaaaaggg aatgagaata gtgaatggac    480
caataataat gactagagaa gaaagaatga agattgttca tgaaattaag gaacgaatat    540
```

-continued tggataaata tggggatgat gttaaggcta ttggtgttta tggctctctt ggtcgtcaga 600
ctgatgggcc ctattcggat attgagatga tgtgtgtcat gtcaacagag gaagcagagt 660
tcagccatga atggacaacc ggtgagtgga aggtggaagt gaattttgat agcgaagaga 720
ttctactaga ttatgcatct caggtggaat cagattggcc gcttacacat ggtcaatttt 780
tctctatttt gccgatttat gattcaggtg gatacttaga gaaagtgtat caaactgcta 840
aatcggtaga agcccaaaag ttccacgatg cgatttgtgc ccttatcgta gaagagctgt 900
ttgaatatgc aggcaaatgg cgtaatattc gtgtgcaagg accgacaaca tttctaccat 960
ccttgactgt acaggtagca atggcaggtg ccatgttgat tggtctgcat catcgcatct 1020
gttatacgac gagcgcttcg gtcttaactg aagcagttaa gcaatcagat cttccttcag 1080
gttatgacca tctgtgccag ttcgtaatgt ctggtcaact ttccgactct gagaaacttc 1140
tggaatcgct agagaatttc tggaatggga ttcaggagtg gacagaacga cacggatata 1200
tagtggatgt gtcaaaacgc ataccatttt gaacgatgac ctctaataat tgttaatcat 1260
gttggttacg tatttattaa cttctcctag tattagtaat tatcatggct gtcatggcgc 1320
attaacggaa taaagggtgt gcttaaatcg ggccattttg cgtaataaga aaaaggatta 1380
attatgagcg aattgaatta ataataaggt aatagattta cattagaaaa 1430

<210> SEQ ID NO 50
<211> LENGTH: 1158
<212> TYPE: DNA
<213> ORGANISM: B. subtilis Spectinomycin cassette 1158 bp

<400> SEQUENCE: 50
catatgcaag ggtttattgt ttttctaaaat ctgattacca attagaatga atatttccca 60
aatattaaat aataaaacaa aaaaattgaa aaaagtgttt ccaccatttt ttcaattttt 120
ttataatttt tttaatctgt tatttaaata gtttatagtt aaatttacat tttcattagt 180
ccattcaata ttctctccaa gataactacg aactgctaac aaaattctct ccctatgttc 240
taatggagaa gattcagcca ctgcatttcc cgcaatatct tttggtatga ttttacccgt 300
gtccatagtt aaaatcatac ggcataaagt taatatagag ttggtttcat catcctgata 360
attatctatt aattcctctg acgaatccat aatggctctt ctcacatcag aaaatggaat 420
atcaggtagt aattcctcta agtcataatt tccgtatatt cttttatttt ttcgttttgc 480
ttggtaaagc attatggtta aatctgaatt taattccttc tgaggaatgt atccttgttc 540
ataaagctct tgtaaccatt ctccataaat aaattcttgt ttgggaggat gattccacgg 600
taccatttct tgctgaataa taattgttaa ttcaatatat cgtaagttgc ttttatctcc 660
tatttttttt gaaataggtc taattttttg tataagtatt tctttacttt gatctgtcaa 720
tggttcagat acgacgacta aaaagtcaag atcactattt ggttttagtc cactctcaac 780
tcctgatcca aacatgtaag taccaataag gttatttttt aaatgtttcc gaagtatttt 840
tttcacttta ttaatttgtt cgtatgtatt caaatatatc ctcctcacta ttttgattag 900
tacctatttt atatccatag ttgttaatta aataaactta atttagttta tttatagatt 960
tcattggctt ctaaattttt tatctagata ataattattt tagttaattt tattctagat 1020
tatatatgat atgatctttc atttccataa aactaaagta agtgtaaacc tattcattgt 1080
tttaaaaata tctcttgcca gtcacgttac gttattagtt atagttatta taacatgtat 1140
tcacgaacga aaatcgat 1158

<210> SEQ ID NO 51
<211> LENGTH: 410
<212> TYPE: PRT
<213> ORGANISM: Escherichia coli NadR

<400> SEQUENCE: 51

```
Met Ser Ser Phe Asp Tyr Leu Lys Thr Ala Ile Lys Gln Gln Gly Cys
1               5                   10                  15

Thr Leu Gln Gln Val Ala Asp Ala Ser Gly Met Thr Lys Gly Tyr Leu
            20                  25                  30

Ser Gln Leu Leu Asn Ala Lys Ile Lys Ser Pro Ser Ala Gln Lys Leu
        35                  40                  45

Glu Ala Leu His Arg Phe Leu Gly Leu Glu Phe Pro Arg Gln Lys Lys
    50                  55                  60

Thr Ile Gly Val Val Phe Gly Lys Phe Tyr Pro Leu His Thr Gly His
65                  70                  75                  80

Ile Tyr Leu Ile Gln Arg Ala Cys Ser Gln Val Asp Glu Leu His Ile
                85                  90                  95

Ile Met Gly Phe Asp Asp Thr Arg Asp Arg Ala Leu Phe Glu Asp Ser
            100                 105                 110

Ala Met Ser Gln Gln Pro Thr Val Pro Asp Arg Leu Arg Trp Leu Leu
        115                 120                 125

Gln Thr Phe Lys Tyr Gln Lys Asn Ile Arg Ile His Ala Phe Asn Glu
    130                 135                 140

Glu Gly Met Glu Pro Tyr Pro His Gly Trp Asp Val Trp Ser Asn Gly
145                 150                 155                 160

Ile Lys Lys Phe Met Ala Glu Lys Gly Ile Gln Pro Asp Leu Ile Tyr
                165                 170                 175

Thr Ser Glu Glu Ala Asp Ala Pro Gln Tyr Met Glu His Leu Gly Ile
            180                 185                 190

Glu Thr Val Leu Val Asp Pro Lys Arg Thr Phe Met Ser Ile Ser Gly
        195                 200                 205

Ala Gln Ile Arg Glu Asn Pro Phe Arg Tyr Trp Glu Tyr Ile Pro Thr
    210                 215                 220

Glu Val Lys Pro Phe Phe Val Arg Thr Val Ala Ile Leu Gly Gly Glu
225                 230                 235                 240

Ser Ser Gly Lys Ser Thr Leu Val Asn Lys Leu Ala Asn Ile Phe Asn
                245                 250                 255

Thr Thr Ser Ala Trp Glu Tyr Gly Arg Asp Tyr Val Phe Ser His Leu
            260                 265                 270

Gly Gly Asp Glu Ile Ala Leu Gln Tyr Ser Asp Tyr Asp Lys Ile Ala
        275                 280                 285

Leu Gly His Ala Gln Tyr Ile Asp Phe Ala Val Lys Tyr Ala Asn Lys
    290                 295                 300

Val Ala Phe Ile Asp Thr Asp Phe Val Thr Thr Gln Ala Phe Cys Lys
305                 310                 315                 320

Lys Tyr Glu Gly Arg Glu His Pro Phe Val Gln Ala Leu Ile Asp Glu
                325                 330                 335

Tyr Arg Phe Asp Leu Val Ile Leu Leu Glu Asn Asn Thr Pro Trp Val
            340                 345                 350

Ala Asp Gly Leu Arg Ser Leu Gly Ser Ser Val Asp Arg Lys Glu Phe
        355                 360                 365

Gln Asn Leu Leu Val Glu Met Leu Glu Glu Asn Asn Ile Glu Phe Val
    370                 375                 380
```

```
Arg Val Glu Glu Glu Asp Tyr Asp Ser Arg Phe Leu Arg Cys Val Glu
385                 390                 395                 400

Leu Val Arg Glu Met Met Gly Glu Gln Arg
                405                 410


<210> SEQ ID NO 52
<211> LENGTH: 180
<212> TYPE: PRT
<213> ORGANISM: Bacillus subtilis YxrA (repressor protein

<400> SEQUENCE: 52

Met Thr Glu Glu Leu Lys Leu Met Gly Ala Asn Arg Arg Asp Gln Leu
1               5                   10                  15

Leu Leu Trp Leu Lys Glu Ser Lys Ser Pro Leu Thr Gly Gly Glu Leu
            20                  25                  30

Ala Lys Lys Ala Asn Val Ser Arg Gln Val Ile Val Gln Asp Ile Ser
        35                  40                  45

Leu Leu Lys Ala Lys Asn Val Pro Ile Ile Ala Thr Ser Gln Gly Tyr
    50                  55                  60

Val Tyr Met Asp Ala Ala Ala Gln Gln His Gln Gln Ala Glu Arg Ile
65                  70                  75                  80

Ile Ala Cys Leu His Gly Pro Glu Arg Thr Glu Glu Glu Leu Gln Leu
                85                  90                  95

Ile Val Asp Glu Gly Val Thr Val Lys Asp Val Lys Ile Glu His Pro
            100                 105                 110

Val Tyr Gly Asp Leu Thr Ala Ala Ile Gln Val Gly Thr Arg Lys Glu
        115                 120                 125

Val Ser His Phe Ile Lys Lys Ile Asn Ser Thr Asn Ala Ala Tyr Leu
    130                 135                 140

Ser Gln Leu Thr Asp Gly Val His Leu His Thr Leu Thr Ala Pro Asp
145                 150                 155                 160

Glu His Arg Ile Asp Gln Ala Cys Gln Ala Leu Glu Glu Ala Gly Ile
                165                 170                 175

Leu Ile Lys Asp
            180


<210> SEQ ID NO 53
<211> LENGTH: 214
<212> TYPE: PRT
<213> ORGANISM: Corynebacterium glutamicum CgR_1153 (repressor protein)

<400> SEQUENCE: 53

Met Pro Ala Ser Pro Glu Ile Gln Met Ala Val Ser Thr Ile Ile Phe
1               5                   10                  15

Ala Leu Arg Pro Gly Pro Gln Asp Leu Pro Ser Leu Trp Ala Pro Phe
            20                  25                  30

Val Pro Arg Thr Arg Glu Pro His Leu Asn Lys Trp Ala Leu Pro Gly
        35                  40                  45

Gly Trp Leu Pro Pro His Glu Glu Leu Glu Asp Ala Ala Ala Arg Thr
    50                  55                  60

Leu Ala Glu Thr Thr Gly Leu His Pro Ser Tyr Leu Glu Gln Leu Tyr
65                  70                  75                  80

Thr Phe Gly Lys Val Asp Arg Ser Pro Thr Gly Arg Val Ile Ser Val
                85                  90                  95

Val Tyr Trp Ala Leu Val Arg Ala Asp Glu Ala Leu Lys Ala Ile Pro
            100                 105                 110
```

Gly Glu Asn Val Gln Trp Phe Pro Ala Asp His Leu Pro Glu Leu Ala
        115                 120                 125

Phe Asp His Asn Asp Ile Val Lys Tyr Ala Leu Glu Arg Leu Arg Thr
    130                 135                 140

Lys Val Glu Tyr Ser Glu Ile Ala His Ser Phe Leu Gly Glu Thr Phe
145                 150                 155                 160

Thr Ile Ala Gln Leu Arg Ser Val His Glu Ala Val Leu Gly His Lys
                165                 170                 175

Leu Asp Ala Ala Asn Phe Arg Arg Ser Val Ala Thr Ser Pro Asp Leu
            180                 185                 190

Ile Asp Thr Gly Glu Val Leu Ala Gly Thr Pro His Arg Pro Pro Lys
        195                 200                 205

Leu Phe Arg Phe Gln Arg
    210

<210> SEQ ID NO 54
<211> LENGTH: 191
<212> TYPE: PRT
<213> ORGANISM: Acinetobacter baylyi PnuC (NR transporter protein)

<400> SEQUENCE: 54

Met Ser Pro Leu Glu Ile Phe Ala Val Ile Ile Ser Val Ile Gly Val
1               5                   10                  15

Ala Leu Thr Ile Lys Arg Asn Met Trp Cys Trp Gly Phe Asn Phe Leu
            20                  25                  30

Ala Phe Ile Leu Tyr Gly Tyr Leu Phe Phe Ser Phe Lys Leu Tyr Gly
        35                  40                  45

Glu Thr Ile Leu Gln Gly Phe Phe Ile Ile Ile Asn Phe Tyr Gly Phe
    50                  55                  60

Tyr Tyr Trp Leu Lys Gly Lys Gln Thr Glu His Glu Ile Arg Ile Val
65                  70                  75                  80

Ala Ile Pro Ala Lys Thr Val Ile Ile Gln Met Leu Leu Ala Ala Leu
                85                  90                  95

Gly Gly Leu Ile Phe Gly Leu Ser Leu Lys His Phe Thr Asp Ala Ala
            100                 105                 110

Val Pro Met Leu Asp Ser Gln Leu Ala Ala Phe Ser Leu Leu Ala Thr
        115                 120                 125

Tyr Trp Thr Ser Arg Lys His Ile Ala Thr Trp Val Leu Trp Val Phe
    130                 135                 140

Val Asp Ile Val Tyr Val Gly Met Phe Ile Tyr Lys Asp Leu Tyr Leu
145                 150                 155                 160

Thr Ala Gly Leu Tyr Ala Ala Phe Val Val Met Ala Ala Phe Gly Trp
                165                 170                 175

Trp Gln Trp Glu Gln Val Lys Arg Lys Gln Arg Ser Gly Leu Ile
            180                 185                 190

<210> SEQ ID NO 55
<211> LENGTH: 230
<212> TYPE: PRT
<213> ORGANISM: Corynebacterium glutamicum NR transporter protein

<400> SEQUENCE: 55

Met Asn Pro Ile Thr Glu Leu Leu Asp Ala Thr Leu Trp Ile Gly Gly
1               5                   10                  15

Val Pro Ile Leu Trp Arg Glu Ile Ile Gly Asn Val Phe Gly Leu Phe
            20                  25                  30

```
Ser Ala Trp Ala Gly Met Arg Arg Ile Val Trp Ala Trp Pro Ile Gly
        35                  40                  45

Ile Ile Gly Asn Ala Leu Leu Phe Thr Val Phe Met Gly Gly Leu Phe
    50                  55                  60

His Thr Pro Gln Asn Leu Asp Leu Tyr Gly Gln Ala Gly Arg Gln Ile
65                  70                  75                  80

Met Phe Ile Ile Val Ser Gly Tyr Gly Trp Tyr Gln Trp Ser Ala Ala
                85                  90                  95

Lys Arg Arg Ala Leu Thr Pro Glu Asn Ala Val Ala Val Val Pro Arg
            100                 105                 110

Trp Ala Ser Thr Lys Glu Arg Ala Gly Ile Val Ile Ala Ala Val Val
        115                 120                 125

Gly Thr Leu Ser Phe Ala Trp Ile Phe Gln Ala Leu Gly Ser Trp Gly
    130                 135                 140

Pro Trp Ala Asp Ala Trp Ile Phe Val Gly Ser Ile Leu Ala Thr Tyr
145                 150                 155                 160

Gly Met Ala Arg Gly Trp Thr Glu Phe Trp Leu Ile Trp Ile Ala Val
                165                 170                 175

Asp Ile Val Gly Val Pro Leu Leu Leu Thr Ala Gly Tyr Tyr Pro Ser
            180                 185                 190

Ala Val Leu Tyr Leu Val Tyr Gly Ala Phe Val Ser Trp Gly Phe Val
        195                 200                 205

Val Trp Leu Arg Val Gln Lys Ala Asp Lys Ala Arg Ala Leu Glu Ala
    210                 215                 220

Gln Glu Ser Val Thr Val
225                 230
```

<210> SEQ ID NO 56
<211> LENGTH: 239
<212> TYPE: PRT
<213> ORGANISM: Escherichia coli PnuC (NR transporter protein)

<400> SEQUENCE: 56

```
Met Asp Phe Phe Ser Val Gln Asn Ile Leu Val His Ile Pro Ile Gly
1               5                   10                  15

Ala Gly Gly Tyr Asp Leu Ser Trp Ile Glu Ala Val Gly Thr Ile Ala
            20                  25                  30

Gly Leu Leu Cys Ile Gly Leu Ala Ser Leu Glu Lys Ile Ser Asn Tyr
        35                  40                  45

Phe Phe Gly Leu Ile Asn Val Thr Leu Phe Gly Ile Ile Phe Phe Gln
    50                  55                  60

Ile Gln Leu Tyr Ala Ser Leu Leu Leu Gln Val Phe Phe Phe Ala Ala
65                  70                  75                  80

Asn Ile Tyr Gly Trp Tyr Ala Trp Ser Arg Gln Thr Ser Gln Asn Glu
                85                  90                  95

Ala Glu Leu Lys Ile Arg Trp Leu Pro Leu Pro Lys Ala Leu Ser Trp
            100                 105                 110

Leu Ala Val Cys Val Val Ser Ile Gly Leu Met Thr Val Phe Ile Asn
        115                 120                 125

Pro Val Phe Ala Phe Leu Thr Arg Val Ala Val Met Ile Met Gln Ala
    130                 135                 140

Leu Gly Leu Gln Val Val Met Pro Glu Leu Gln Pro Asp Ala Phe Pro
145                 150                 155                 160

Phe Trp Asp Ser Cys Met Met Val Leu Ser Ile Val Ala Met Ile Leu
                165                 170                 175
```

```
Met Thr Arg Lys Tyr Val Glu Asn Trp Leu Leu Trp Val Ile Ile Asn
            180                 185                 190

Val Ile Ser Val Val Ile Phe Ala Leu Gln Gly Val Tyr Ala Met Ser
        195                 200                 205

Leu Glu Tyr Ile Ile Leu Thr Phe Ile Ala Leu Asn Gly Ser Arg Met
    210                 215                 220

Trp Ile Asn Ser Ala Arg Glu Arg Gly Ser Arg Ala Leu Ser His
225                 230                 235


<210> SEQ ID NO 57
<211> LENGTH: 550
<212> TYPE: PRT
<213> ORGANISM: Escherichia coli UshA (nucleotide hydrolase)

<400> SEQUENCE: 57

Met Lys Leu Leu Gln Arg Gly Val Ala Leu Ala Leu Leu Thr Thr Phe
1               5                   10                  15

Thr Leu Ala Ser Glu Thr Ala Leu Ala Tyr Glu Gln Asp Lys Thr Tyr
            20                  25                  30

Lys Ile Thr Val Leu His Thr Asn Asp His His Gly His Phe Trp Arg
        35                  40                  45

Asn Glu Tyr Gly Glu Tyr Gly Leu Ala Ala Gln Lys Thr Leu Val Asp
    50                  55                  60

Gly Ile Arg Lys Glu Val Ala Ala Glu Gly Gly Ser Val Leu Leu Leu
65                  70                  75                  80

Ser Gly Gly Asp Ile Asn Thr Gly Val Pro Glu Ser Asp Leu Gln Asp
                85                  90                  95

Ala Glu Pro Asp Phe Arg Gly Met Asn Leu Val Gly Tyr Asp Ala Met
            100                 105                 110

Ala Ile Gly Asn His Glu Phe Asp Asn Pro Leu Thr Val Leu Arg Gln
        115                 120                 125

Gln Glu Lys Trp Ala Lys Phe Pro Leu Leu Ser Ala Asn Ile Tyr Gln
    130                 135                 140

Lys Ser Thr Gly Glu Arg Leu Phe Lys Pro Trp Ala Leu Phe Lys Arg
145                 150                 155                 160

Gln Asp Leu Lys Ile Ala Val Ile Gly Leu Thr Thr Asp Asp Thr Ala
                165                 170                 175

Lys Ile Gly Asn Pro Glu Tyr Phe Thr Asp Ile Glu Phe Arg Lys Pro
            180                 185                 190

Ala Asp Glu Ala Lys Leu Val Ile Gln Glu Leu Gln Gln Thr Glu Lys
        195                 200                 205

Pro Asp Ile Ile Ile Ala Ala Thr His Met Gly His Tyr Asp Asn Gly
    210                 215                 220

Glu His Gly Ser Asn Ala Pro Gly Asp Val Glu Met Ala Arg Ala Leu
225                 230                 235                 240

Pro Ala Gly Ser Leu Ala Met Ile Val Gly Gly His Ser Gln Asp Pro
                245                 250                 255

Val Cys Met Ala Ala Glu Asn Lys Lys Gln Val Asp Tyr Val Pro Gly
            260                 265                 270

Thr Pro Cys Lys Pro Asp Gln Gln Asn Gly Ile Trp Ile Val Gln Ala
        275                 280                 285

His Glu Trp Gly Lys Tyr Val Gly Arg Ala Asp Phe Glu Phe Arg Asn
    290                 295                 300

Gly Glu Met Lys Met Val Asn Tyr Gln Leu Ile Pro Val Asn Leu Lys
```

305 310 315 320

Lys Lys Val Thr Trp Glu Asp Gly Lys Ser Glu Arg Val Leu Tyr Thr
325 330 335

Pro Glu Ile Ala Glu Asn Gln Gln Met Ile Ser Leu Leu Ser Pro Phe
340 345 350

Gln Asn Lys Gly Lys Ala Gln Leu Glu Val Lys Ile Gly Glu Thr Asn
355 360 365

Gly Arg Leu Glu Gly Asp Arg Asp Lys Val Arg Phe Val Gln Thr Asn
370 375 380

Met Gly Arg Leu Ile Leu Ala Ala Gln Met Asp Arg Thr Gly Ala Asp
385 390 395 400

Phe Ala Val Met Ser Gly Gly Gly Ile Arg Asp Ser Ile Glu Ala Gly
405 410 415

Asp Ile Ser Tyr Lys Asn Val Leu Lys Val Gln Pro Phe Gly Asn Val
420 425 430

Val Val Tyr Ala Asp Met Thr Gly Lys Glu Val Ile Asp Tyr Leu Thr
435 440 445

Ala Val Ala Gln Met Lys Pro Asp Ser Gly Ala Tyr Pro Gln Phe Ala
450 455 460

Asn Val Ser Phe Val Ala Lys Asp Gly Lys Leu Asn Asp Leu Lys Ile
465 470 475 480

Lys Gly Glu Pro Val Asp Pro Ala Lys Thr Tyr Arg Met Ala Thr Leu
485 490 495

Asn Phe Asn Ala Thr Gly Gly Asp Gly Tyr Pro Arg Leu Asp Asn Lys
500 505 510

Pro Gly Tyr Val Asn Thr Gly Phe Ile Asp Ala Glu Val Leu Lys Ala
515 520 525

Tyr Ile Gln Lys Ser Ser Pro Leu Asp Val Ser Val Tyr Glu Pro Lys
530 535 540

Gly Glu Val Ser Trp Gln
545 550

<210> SEQ ID NO 58
<211> LENGTH: 1462
<212> TYPE: PRT
<213> ORGANISM: Bacillus subtilis YfkN (nucleotide hydrolase)

<400> SEQUENCE: 58

Met Arg Ile Gln Lys Arg Arg Thr His Val Glu Asn Ile Leu Arg Ile
1 5 10 15

Leu Leu Pro Pro Ile Met Ile Leu Ser Leu Ile Leu Pro Thr Pro Pro
20 25 30

Ile His Ala Glu Glu Ser Ala Ala Pro Gln Val His Leu Ser Ile Leu
35 40 45

Ala Thr Thr Asp Ile His Ala Asn Met Met Asp Tyr Asp Tyr Tyr Ser
50 55 60

Asp Lys Glu Thr Ala Asp Phe Gly Leu Ala Arg Thr Ala Gln Leu Ile
65 70 75 80

Gln Lys His Arg Glu Gln Asn Pro Asn Thr Leu Leu Val Asp Asn Gly
85 90 95

Asp Leu Ile Gln Gly Asn Pro Leu Gly Glu Tyr Ala Val Lys Tyr Gln
100 105 110

Lys Asp Asp Ile Ile Ser Gly Thr Lys Thr His Pro Ile Ile Ser Val
115 120 125

-continued

```
Met Asn Ala Leu Lys Tyr Asp Ala Gly Thr Leu Gly Asn His Glu Phe
    130                 135                 140

Asn Tyr Gly Leu Asp Phe Leu Asp Gly Thr Ile Lys Gly Ala Asp Phe
145                 150                 155                 160

Pro Ile Val Asn Ala Asn Val Lys Thr Thr Ser Gly Glu Asn Arg Tyr
                165                 170                 175

Thr Pro Tyr Val Ile Asn Glu Lys Thr Leu Ile Asp Glu Asn Gly Asn
            180                 185                 190

Glu Gln Lys Val Lys Val Gly Tyr Ile Gly Phe Val Pro Pro Gln Ile
        195                 200                 205

Met Thr Trp Asp Lys Lys Asn Leu Glu Gly Gln Val Gln Val Gln Asp
    210                 215                 220

Ile Val Glu Ser Ala Asn Glu Thr Ile Pro Lys Met Lys Ala Glu Gly
225                 230                 235                 240

Ala Asp Val Ile Ile Ala Leu Ala His Thr Gly Ile Glu Lys Gln Ala
                245                 250                 255

Gln Ser Ser Gly Ala Glu Asn Ala Val Phe Asp Leu Ala Thr Lys Thr
            260                 265                 270

Lys Gly Ile Asp Ala Ile Ile Ser Gly His Gln His Gly Leu Phe Pro
        275                 280                 285

Ser Ala Glu Tyr Ala Gly Val Ala Gln Phe Asn Val Glu Lys Gly Thr
    290                 295                 300

Ile Asn Gly Ile Pro Val Val Met Pro Ser Ser Trp Gly Lys Tyr Leu
305                 310                 315                 320

Gly Val Ile Asp Leu Lys Leu Glu Lys Ala Asp Gly Ser Trp Lys Val
                325                 330                 335

Ala Asp Ser Lys Gly Ser Ile Glu Ser Ile Ala Gly Asn Val Thr Ser
            340                 345                 350

Arg Asn Glu Thr Val Thr Asn Thr Ile Gln Gln Thr His Gln Asn Thr
        355                 360                 365

Leu Glu Tyr Val Arg Lys Pro Val Gly Lys Thr Glu Ala Asp Ile Asn
    370                 375                 380

Ser Phe Phe Ala Gln Val Lys Asp Asp Pro Ser Ile Gln Ile Val Thr
385                 390                 395                 400

Asp Ala Gln Lys Trp Tyr Ala Glu Lys Glu Met Lys Asp Thr Glu Tyr
                405                 410                 415

Lys Asn Leu Pro Ile Leu Ser Ala Gly Ala Pro Phe Lys Ala Gly Gly
            420                 425                 430

Arg Asn Gly Ala Asn Tyr Tyr Thr Asn Ile Pro Ala Gly Asp Leu Ala
        435                 440                 445

Ile Lys Asn Val Gly Asp Leu Tyr Leu Tyr Asp Asn Thr Val Gln Ile
    450                 455                 460

Val Lys Leu Thr Gly Ser Glu Val Lys Asp Trp Leu Glu Met Ser Ala
465                 470                 475                 480

Gly Gln Phe Asn Gln Ile Asp Pro Ala Lys Gly Gly Asp Gln Ala Leu
                485                 490                 495

Leu Asn Glu Asn Phe Arg Ser Tyr Asn Phe Asp Val Ile Asp Gly Val
            500                 505                 510

Thr Tyr Gln Val Asp Val Thr Lys Pro Ala Lys Tyr Asn Glu Asn Gly
        515                 520                 525

Lys Val Ile Asn Ala Asp Ser Ser Arg Ile Ile Asn Leu Ser Tyr Glu
    530                 535                 540

Gly Lys Pro Ile Ser Pro Ser Gln Glu Phe Leu Val Val Thr Asn Asn
```

-continued

```
545                 550                 555                 560

Tyr Arg Ala Ser Gly Gly Gly Gly Phe Pro His Leu Thr Ser Asp Lys
                565                 570                 575

Ile Val His Gly Ser Ala Val Glu Asn Arg Gln Val Leu Met Asp Tyr
            580                 585                 590

Ile Ile Glu Gln Lys Thr Val Asn Pro Lys Ala Asp Asn Asn Trp Ser
        595                 600                 605

Ile Ala Pro Val Ser Gly Thr Asn Leu Thr Phe Glu Ser Ser Leu Leu
    610                 615                 620

Ala Lys Pro Phe Ala Asp Lys Ala Asp Asp Val Ala Tyr Val Gly Lys
625                 630                 635                 640

Ser Ala Asn Glu Gly Tyr Gly Val Tyr Lys Leu Gln Phe Asp Asp Asp
                645                 650                 655

Ser Asn Pro Asp Pro Pro Lys Asp Gly Leu Trp Asp Leu Thr Val Met
            660                 665                 670

His Thr Asn Asp Thr His Ala His Leu Asp Asp Ala Ala Arg Arg Met
        675                 680                 685

Thr Lys Ile Asn Glu Val Arg Ser Glu Thr Asn His Asn Ile Leu Leu
    690                 695                 700

Asp Ala Gly Asp Val Phe Ser Gly Asp Leu Tyr Phe Thr Lys Trp Asn
705                 710                 715                 720

Gly Leu Ala Asp Leu Lys Met Met Asn Met Met Gly Tyr Asp Ala Met
                725                 730                 735

Thr Phe Gly Asn His Glu Phe Asp Lys Gly Pro Thr Val Leu Ser Asp
            740                 745                 750

Phe Leu Ser Gly Asn Ser Ala Thr Val Asp Pro Ala Asn Arg Tyr His
        755                 760                 765

Phe Glu Ala Pro Glu Phe Pro Ile Val Ser Ala Asn Val Asp Val Ser
    770                 775                 780

Asn Glu Pro Lys Leu Lys Ser Phe Val Lys Lys Pro Gln Thr Phe Thr
785                 790                 795                 800

Ala Gly Glu Lys Lys Glu Ala Gly Ile His Pro Tyr Ile Leu Leu Asp
                805                 810                 815

Val Asp Gly Glu Lys Val Ala Val Phe Gly Leu Thr Thr Glu Asp Thr
            820                 825                 830

Ala Thr Thr Ser Ser Pro Gly Lys Ser Ile Val Phe Asn Asp Ala Phe
        835                 840                 845

Glu Thr Ala Gln Asn Thr Val Lys Ala Ile Gln Glu Glu Glu Lys Val
    850                 855                 860

Asn Lys Ile Ile Ala Leu Thr His Ile Gly His Asn Arg Asp Leu Glu
865                 870                 875                 880

Leu Ala Lys Lys Val Lys Gly Ile Asp Leu Ile Ile Gly Gly His Thr
                885                 890                 895

His Thr Leu Val Asp Lys Met Glu Val Val Asn Asn Glu Glu Pro Thr
            900                 905                 910

Ile Val Ala Gln Ala Lys Glu Tyr Gly Gln Phe Leu Gly Arg Val Asp
        915                 920                 925

Val Ala Phe Asp Glu Lys Gly Val Val Gln Thr Asp Lys Ser Asn Leu
    930                 935                 940

Ser Val Leu Pro Ile Asp Glu His Thr Glu Glu Asn Pro Glu Ala Lys
945                 950                 955                 960

Gln Glu Leu Asp Gln Phe Lys Asn Glu Leu Glu Asp Val Lys Asn Glu
                965                 970                 975
```

```
Lys Val Gly Tyr Thr Asp Val Ala Leu Asp Gly Gln Arg Glu His Val
            980                 985                 990

Arg Thr Lys Glu Thr Asn Leu Gly  Asn Phe Ile Ala Asp  Gly Met Leu
        995                 1000                1005

Ala Lys  Ala Lys Glu Ala Ala  Gly Ala Arg Ile Ala  Ile Thr Asn
    1010                 1015                 1020

Gly Gly  Gly Ile Arg Ala Gly  Ile Asp Lys Gly Asp  Ile Thr Leu
    1025                 1030                 1035

Gly Glu  Val Leu Asn Val Met  Pro Phe Gly Asn Thr  Leu Tyr Val
    1040                 1045                 1050

Ala Asp  Leu Thr Gly Lys Gln  Ile Lys Glu Ala Leu  Glu Gln Gly
    1055                 1060                 1065

Leu Ser  Asn Val Glu Asn Gly  Gly Gly Ala Phe Pro  Gln Val Ala
    1070                 1075                 1080

Gly Ile  Glu Tyr Thr Phe Thr  Leu Asn Asn Lys Pro  Gly His Arg
    1085                 1090                 1095

Val Leu  Glu Val Lys Ile Glu  Ser Pro Asn Gly Asp  Lys Val Ala
    1100                 1105                 1110

Ile Asn  Thr Asp Asp Thr Tyr  Arg Val Ala Thr Asn  Asn Phe Val
    1115                 1120                 1125

Gly Ala  Gly Gly Asp Gly Tyr  Ser Val Phe Thr Glu  Ala Ser His
    1130                 1135                 1140

Gly Glu  Asp Leu Gly Tyr Val  Asp Tyr Glu Ile Phe  Thr Glu Gln
    1145                 1150                 1155

Leu Lys  Lys Leu Gly Asn Lys  Val Ser Pro Lys Val  Glu Gly Arg
    1160                 1165                 1170

Ile Lys  Glu Val Phe Leu Pro  Thr Lys Gln Lys Asp  Gly Ser Trp
    1175                 1180                 1185

Thr Leu  Asp Glu Asp Lys Phe  Ala Ile Tyr Ala Lys  Asn Ala Asn
    1190                 1195                 1200

Thr Pro  Phe Val Tyr Tyr Gly  Ile His Glu Gly Ser  Gln Glu Lys
    1205                 1210                 1215

Pro Ile  Asn Leu Lys Val Lys  Lys Asp Gln Val Lys  Leu Leu Lys
    1220                 1225                 1230

Glu Arg  Glu Ser Asp Pro Ser  Leu Thr Met Phe Asn  Tyr Trp Tyr
    1235                 1240                 1245

Ser Met  Lys Met Pro Met Ala  Asn Leu Lys Thr Ala  Asp Thr Ala
    1250                 1255                 1260

Ile Gly  Ile Lys Ser Thr Gly  Glu Leu Asp Val Ser  Leu Ser Asp
    1265                 1270                 1275

Val Tyr  Asp Phe Thr Val Lys  Gln Lys Gly Lys Glu  Ile Lys Ser
    1280                 1285                 1290

Phe Lys  Glu Pro Val Gln Leu  Ser Leu Arg Met Phe  Asp Ile Glu
    1295                 1300                 1305

Glu Ala  His Asn Pro Ala Ile  Tyr His Val Asp Arg  Lys Lys Lys
    1310                 1315                 1320

Ala Phe  Thr Lys Thr Gly His  Gly Ser Val Asp Asp  Asp Met Val
    1325                 1330                 1335

Thr Gly  Tyr Thr Asn His Phe  Ser Glu Tyr Thr Ile  Leu Asn Ser
    1340                 1345                 1350

Gly Ser  Asn Asn Lys Pro Pro  Ala Phe Pro Ser Asp  Gln Pro Thr
    1355                 1360                 1365
```

Gly Gly Asp Asp Gly Asn His Gly Gly Gly Ser Asp Lys Pro Gly
1370 1375 1380

Gly Lys Gln Pro Thr Asp Gly Asn Gly Gly Asn Asp Thr Pro Pro
1385 1390 1395

Gly Thr Gln Pro Thr Asn Gly Ser Gly Gly Asn Gly Ser Gly Gly
1400 1405 1410

Ser Gly Thr Asp Gly Pro Ala Gly Gly Leu Leu Pro Asp Thr Ala
1415 1420 1425

Thr Ser Met Tyr Ser Ile Leu Leu Ala Gly Phe Leu Ile Ser Ala
1430 1435 1440

Leu Gly Thr Ala Met Tyr Leu His Gln Arg Arg Lys Gln Asn Arg
1445 1450 1455

Ala Asn Gln Ala
1460

<210> SEQ ID NO 59
<211> LENGTH: 693
<212> TYPE: PRT
<213> ORGANISM: Corynebacterium glutamicum Cg0397 (nucleotide hydrolase)

<400> SEQUENCE: 59

Met Lys Arg Leu Ser Arg Ala Ala Leu Ala Val Val Ala Thr Thr Ala
1 5 10 15

Val Ser Phe Ser Ala Leu Ala Val Pro Ala Phe Ala Asp Glu Ala Ser
20 25 30

Asn Val Glu Leu Asn Ile Leu Gly Val Thr Asp Phe His Gly His Ile
35 40 45

Glu Gln Lys Ala Val Lys Asp Asp Lys Gly Val Ile Thr Gly Tyr Ser
50 55 60

Glu Met Gly Ala Ser Gly Val Ala Cys Tyr Val Asp Ala Glu Arg Ala
65 70 75 80

Asp Asn Pro Asn Thr Arg Phe Ile Thr Val Gly Asp Asn Ile Gly Gly
85 90 95

Ser Pro Phe Val Ser Ser Ile Leu Lys Asp Glu Pro Thr Leu Gln Ala
100 105 110

Leu Ser Ala Ile Gly Val Asp Ala Ser Ala Leu Gly Asn His Glu Phe
115 120 125

Asp Gln Gly Tyr Ser Asp Leu Val Asn Arg Val Ser Leu Asp Gly Ser
130 135 140

Gly Ser Ala Lys Phe Pro Tyr Leu Gly Ala Asn Val Glu Gly Gly Thr
145 150 155 160

Pro Ala Pro Ala Lys Ser Glu Ile Ile Glu Met Asp Gly Val Lys Ile
165 170 175

Ala Tyr Val Gly Ala Val Thr Glu Glu Thr Ala Thr Leu Val Ser Pro
180 185 190

Ala Gly Ile Glu Gly Ile Thr Phe Thr Gly Asp Ile Asp Ala Ile Asn
195 200 205

Ala Glu Ala Asp Arg Val Ile Glu Ala Gly Glu Ala Asp Val Val Ile
210 215 220

Ala Leu Ile His Ala Glu Ala Ala Pro Thr Asp Leu Phe Ser Asn Asn
225 230 235 240

Val Asp Val Val Phe Ser Gly His Thr His Phe Asp Tyr Val Ala Glu
245 250 255

Gly Glu Ala Arg Gly Asp Lys Gln Pro Leu Val Val Ile Gln Gly His
260 265 270

-continued

```
Glu Tyr Gly Lys Val Ile Ser Val Glu Ile Ser Tyr Asp Arg Glu Ala
        275                 280                 285

Gly Lys Ile Thr Asn Ile Glu Ala Lys Asn Val Ser Ala Thr Asp Val
    290                 295                 300

Val Glu Asn Cys Glu Thr Pro Asn Thr Ala Val Asp Ala Ile Val Ala
305                 310                 315                 320

Ala Ala Val Glu Ala Ala Glu Glu Ala Gly Asn Glu Val Val Ala Thr
                325                 330                 335

Ile Asp Asn Gly Phe Tyr Arg Gly Ala Asp Glu Glu Gly Thr Thr Gly
            340                 345                 350

Ser Asn Arg Gly Val Glu Ser Ser Leu Ser Asn Leu Ile Ala Glu Ala
        355                 360                 365

Gly Leu Trp Ala Val Asn Asp Ala Thr Ile Leu Asn Ala Asp Ile Gly
    370                 375                 380

Ile Met Asn Ala Gly Gly Val Arg Ala Asp Leu Glu Ala Gly Glu Val
385                 390                 395                 400

Thr Phe Ala Asp Ala Tyr Ala Thr Gln Asn Phe Ser Asn Thr Tyr Gly
                405                 410                 415

Val Arg Glu Val Ser Gly Ala Gln Phe Lys Glu Ala Leu Glu Gln Gln
            420                 425                 430

Trp Lys Glu Thr Gly Asp Arg Pro Arg Leu Ala Leu Gly Leu Ser Ser
        435                 440                 445

Asn Val Gln Tyr Ser Tyr Asp Glu Thr Arg Glu Tyr Gly Asp Arg Ile
    450                 455                 460

Thr His Ile Thr Phe Asn Gly Glu Pro Met Asp Met Lys Glu Thr Tyr
465                 470                 475                 480

Arg Val Thr Gly Ser Ser Phe Leu Leu Ala Gly Gly Asp Ser Phe Thr
                485                 490                 495

Ala Phe Ala Glu Gly Gly Pro Ile Ala Glu Thr Gly Met Val Asp Ile
            500                 505                 510

Asp Leu Phe Asn Asn Tyr Ile Ala Ala His Pro Asp Ala Pro Ile Arg
        515                 520                 525

Ala Asn Gln Ser Ser Val Gly Ile Ala Leu Ser Gly Pro Ala Val Ala
    530                 535                 540

Glu Asp Gly Thr Leu Val Pro Gly Glu Glu Leu Thr Val Asp Leu Ser
545                 550                 555                 560

Ser Leu Ser Tyr Thr Gly Pro Glu Ala Lys Pro Thr Thr Val Glu Val
                565                 570                 575

Thr Val Gly Thr Glu Lys Lys Thr Ala Asp Val Asp Asn Thr Ile Val
            580                 585                 590

Pro Gln Phe Asp Ser Thr Gly Lys Ala Thr Val Thr Leu Thr Val Pro
        595                 600                 605

Glu Gly Ala Thr Ser Val Lys Ile Ala Thr Asp Asn Gly Thr Thr Phe
    610                 615                 620

Glu Leu Pro Val Thr Val Asn Gly Glu Gly Asn Asn Asp Asp Asp Asp
625                 630                 635                 640

Asp Lys Glu Gln Gln Ser Ser Gly Ser Ser Asp Ala Gly Ser Leu Val
                645                 650                 655

Ala Val Leu Gly Val Leu Gly Ala Leu Gly Gly Leu Val Ala Phe Phe
            660                 665                 670

Leu Asn Ser Ala Gln Gly Ala Pro Phe Leu Ala Gln Leu Gln Ala Met
        675                 680                 685
```

Phe Ala Gln Phe Met
690

<210> SEQ ID NO 60
<211> LENGTH: 165
<212> TYPE: PRT
<213> ORGANISM: Escherichia coli PncC (nicotinamide mononucleotide amidohydrolase)

<400> SEQUENCE: 60

Met Thr Asp Ser Glu Leu Met Gln Leu Ser Glu Gln Val Gly Gln Ala
1 5 10 15

Leu Lys Ala Arg Gly Ala Thr Val Thr Thr Ala Glu Ser Cys Thr Gly
20 25 30

Gly Trp Val Ala Lys Val Ile Thr Asp Ile Ala Gly Ser Ser Ala Trp
35 40 45

Phe Glu Arg Gly Phe Val Thr Tyr Ser Asn Glu Ala Lys Ala Gln Met
50 55 60

Ile Gly Val Arg Glu Glu Thr Leu Ala Gln His Gly Ala Val Ser Glu
65 70 75 80

Pro Val Val Val Glu Met Ala Ile Gly Ala Leu Lys Ala Ala Arg Ala
85 90 95

Asp Tyr Ala Val Ser Ile Ser Gly Ile Ala Gly Pro Asp Gly Gly Ser
100 105 110

Glu Glu Lys Pro Val Gly Thr Val Trp Phe Ala Phe Ala Thr Ala Arg
115 120 125

Gly Glu Gly Ile Thr Arg Arg Glu Cys Phe Ser Gly Asp Arg Asp Ala
130 135 140

Val Arg Arg Gln Ala Thr Ala Tyr Ala Leu Gln Thr Leu Trp Gln Gln
145 150 155 160

Phe Leu Gln Asn Thr
165

<210> SEQ ID NO 61
<211> LENGTH: 415
<212> TYPE: PRT
<213> ORGANISM: Bacillus subtilis CinA (nicotinamide mononucleotide amidohydrolase)

<400> SEQUENCE: 61

Met Glu Phe Pro Lys Lys Ala Glu Ile Ile Ala Val Gly Ser Glu Leu
1 5 10 15

Leu Leu Gly Gln Ile Ala Asn Thr Asn Ala Gln Phe Ile Ser Lys Gln
20 25 30

Leu Ala Glu Ile Gly Val His Val Phe Tyr His Thr Ala Val Gly Asp
35 40 45

Asn Pro Glu Arg Leu Lys Gln Val Ile Arg Ile Ala Glu Glu Arg Ser
50 55 60

Asp Phe Ile Ile Phe Gly Gly Leu Gly Pro Thr Lys Asp Asp Leu Thr
65 70 75 80

Lys Glu Thr Ile Ala Asn Thr Leu Gly Arg Pro Leu Val Leu Asn Asp
85 90 95

Glu Ala Phe Gln Ser Ile Glu Asp Tyr Pro Lys Arg Thr Lys Arg Thr
100 105 110

Met Ser Pro Asn Asn Arg Lys Gln Ala Leu Val Ile Glu Gly Ser Asp
115 120 125

Val Leu Ala Asn His Phe Gly Met Ala Pro Gly Met Leu Thr Glu His

```
    130                 135                 140

Glu Ser Arg Tyr Tyr Met Leu Leu Pro Gly Pro Pro Ser Glu Leu Arg
145                 150                 155                 160

Pro Met Phe Glu Asn Glu Ala Lys Pro Leu Leu Leu Lys Lys Met Gly
                165                 170                 175

Ser Asn Glu Lys Ile Val Ser Thr Val Leu Arg Phe Phe Gly Ile Gly
            180                 185                 190

Glu Ser Gln Leu Glu Pro Asp Leu Glu Asp Ile Ile Asp Ala Gln Thr
        195                 200                 205

Asn Pro Thr Ile Ala Pro Leu Ala Ala Asp Gly Glu Val Thr Leu Arg
    210                 215                 220

Leu Thr Ala Lys His Ala Asp Glu Lys Glu Thr Glu Arg Leu Leu Lys
225                 230                 235                 240

Glu Thr Glu Ala Val Ile Leu Glu Arg Val Gly Glu Phe Phe Tyr Gly
                245                 250                 255

Tyr Asp Asp Thr Ser Leu Val Lys Glu Leu Ser Ile Ala Cys Lys Glu
            260                 265                 270

Lys Gly Ile Thr Ile Ser Ala Ala Glu Ser Phe Thr Gly Gly Leu Phe
        275                 280                 285

Ser Glu Trp Leu Thr Asp His Ser Gly Ala Ser Lys Leu Phe Ala Gly
    290                 295                 300

Gly Val Val Cys Tyr Thr Asn Asp Val Lys Gln Asn Val Leu Gly Val
305                 310                 315                 320

Lys Lys Glu Thr Leu Asp Arg Phe Gly Ala Val Ser Lys Glu Cys Ala
                325                 330                 335

Ser Glu Leu Ala Lys Gly Val Gln Lys Leu Thr Gly Ser Asp Ile Gly
            340                 345                 350

Ile Ser Phe Thr Gly Val Ala Gly Pro Asp Ala Gln Glu Gly His Glu
        355                 360                 365

Pro Gly His Val Phe Ile Gly Ile Ser Ala Asn Gly Lys Glu Glu Val
    370                 375                 380

His Glu Phe His Phe Ala Gly Ser Arg Thr Gly Ile Arg Lys Arg Gly
385                 390                 395                 400

Ala Lys Tyr Gly Cys His Leu Ile Leu Lys Leu Leu Glu Gln Lys
                405                 410                 415


<210> SEQ ID NO 62
<211> LENGTH: 172
<212> TYPE: PRT
<213> ORGANISM: Corynebacterium glutamicum  Cg2153 (nicotinamide
      mononucleotide amidohydrolase)

<400> SEQUENCE: 62

Met Ser Glu Asn Leu Ala Gly Arg Val Val Glu Leu Leu Lys Ser Arg
1               5                   10                  15

Gly Glu Thr Leu Ala Phe Cys Glu Ser Leu Thr Ala Gly Leu Ala Ser
            20                  25                  30

Ala Thr Ile Ala Glu Ile Pro Gly Ala Ser Val Val Leu Lys Gly Gly
        35                  40                  45

Leu Val Thr Tyr Ala Thr Glu Leu Lys Val Ala Leu Ala Gly Val Pro
    50                  55                  60

Gln Glu Leu Ile Asp Ala His Gly Val Val Ser Pro Gln Cys Ala Arg
65                  70                  75                  80

Ala Met Ala Thr Gly Ala Ala His Arg Cys Gln Ala Asp Trp Ala Val
                85                  90                  95
```

Ser Leu Thr Gly Val Ala Gly Pro Ser Lys Gln Asp Gly His Pro Val
100 105 110

Gly Glu Val Trp Ile Gly Val Ala Gly Pro Ala His Phe Gly Ala Ser
115 120 125

Gly Thr Ile Asp Ala Tyr Arg Ala Phe Glu Ser Glu Gln Gln Val Ile
130 135 140

Leu Ala Glu Leu Gly Arg His His Ile Arg Glu Ser Ala Val Gln Gln
145 150 155 160

Ser Phe Arg Leu Leu Ile Asp His Ile Glu Ser Gln
165 170

<210> SEQ ID NO 63
<211> LENGTH: 213
<212> TYPE: PRT
<213> ORGANISM: Escherichia coli NadD (nicotinic acid mononucleotide adenyltransferase)

<400> SEQUENCE: 63

Met Lys Ser Leu Gln Ala Leu Phe Gly Gly Thr Phe Asp Pro Val His
1 5 10 15

Tyr Gly His Leu Lys Pro Val Glu Thr Leu Ala Asn Leu Ile Gly Leu
20 25 30

Thr Arg Val Thr Ile Ile Pro Asn Asn Val Pro Pro His Arg Pro Gln
35 40 45

Pro Glu Ala Asn Ser Val Gln Arg Lys His Met Leu Glu Leu Ala Ile
50 55 60

Ala Asp Lys Pro Leu Phe Thr Leu Asp Glu Arg Glu Leu Lys Arg Asn
65 70 75 80

Ala Pro Ser Tyr Thr Ala Gln Thr Leu Lys Glu Trp Arg Gln Glu Gln
85 90 95

Gly Pro Asp Val Pro Leu Ala Phe Ile Ile Gly Gln Asp Ser Leu Leu
100 105 110

Thr Phe Pro Thr Trp Tyr Glu Tyr Glu Thr Ile Leu Asp Asn Ala His
115 120 125

Leu Ile Val Cys Arg Arg Pro Gly Tyr Pro Leu Glu Met Ala Gln Pro
130 135 140

Gln Tyr Gln Gln Trp Leu Glu Asp His Leu Thr His Asn Pro Glu Asp
145 150 155 160

Leu His Leu Gln Pro Ala Gly Lys Ile Tyr Leu Ala Glu Thr Pro Trp
165 170 175

Phe Asn Ile Ser Ala Thr Ile Ile Arg Glu Arg Leu Gln Asn Gly Glu
180 185 190

Ser Cys Glu Asp Leu Leu Pro Glu Pro Val Leu Thr Tyr Ile Asn Gln
195 200 205

Gln Gly Leu Tyr Arg
210

<210> SEQ ID NO 64
<211> LENGTH: 189
<212> TYPE: PRT
<213> ORGANISM: Bacillus subtilis NadD (nicotinic acid mononucleotide adenyltransferase)

<400> SEQUENCE: 64

Met Lys Lys Ile Gly Ile Phe Gly Gly Thr Phe Asp Pro Pro His Asn
1 5 10 15

-continued

```
Gly His Leu Leu Met Ala Asn Glu Val Leu Tyr Gln Ala Gly Leu Asp
            20                  25                  30

Glu Ile Trp Phe Met Pro Asn Gln Ile Pro Pro His Lys Gln Asn Glu
        35                  40                  45

Asp Tyr Thr Asp Ser Phe His Arg Val Glu Met Leu Lys Leu Ala Ile
    50                  55                  60

Gln Ser Asn Pro Ser Phe Lys Leu Glu Leu Val Glu Met Glu Arg Glu
65                  70                  75                  80

Gly Pro Ser Tyr Thr Phe Asp Thr Val Ser Leu Leu Lys Gln Arg Tyr
                85                  90                  95

Pro Asn Asp Gln Leu Phe Phe Ile Ile Gly Ala Asp Met Ile Glu Tyr
            100                 105                 110

Leu Pro Lys Trp Tyr Lys Leu Asp Glu Leu Leu Asn Leu Ile Gln Phe
        115                 120                 125

Ile Gly Val Lys Arg Pro Gly Phe His Val Glu Thr Pro Tyr Pro Leu
    130                 135                 140

Leu Phe Ala Asp Val Pro Glu Phe Glu Val Ser Ser Thr Met Ile Arg
145                 150                 155                 160

Glu Arg Phe Lys Ser Lys Lys Pro Thr Asp Tyr Leu Ile Pro Asp Lys
                165                 170                 175

Val Lys Lys Tyr Val Glu Glu Asn Gly Leu Tyr Glu Ser
            180                 185


<210> SEQ ID NO 65
<211> LENGTH: 226
<212> TYPE: PRT
<213> ORGANISM: Corynebacterium glutamicum Cg2584 (nicotinic acid
      mononucleotide adenyltransferase)

<400> SEQUENCE: 65

Met Arg Thr Leu Tyr Cys Pro Leu Met Thr Thr Thr Val Lys Arg Arg
1               5                   10                  15

Ala Arg Ile Gly Ile Met Gly Gly Thr Phe Asp Pro Ile His Asn Gly
            20                  25                  30

His Leu Val Ala Gly Ser Glu Val Ala Asp Arg Phe Asp Leu Asp Leu
        35                  40                  45

Val Val Tyr Val Pro Thr Gly Gln Pro Trp Gln Lys Ala Asn Lys Lys
    50                  55                  60

Val Ser Pro Ala Glu Asp Arg Tyr Leu Met Thr Val Ile Ala Thr Ala
65                  70                  75                  80

Ser Asn Pro Arg Phe Met Val Ser Arg Val Asp Ile Asp Arg Gly Gly
                85                  90                  95

Asp Thr Tyr Thr Ile Asp Thr Leu Gln Asp Leu Ser Lys Gln Tyr Pro
            100                 105                 110

Asp Ala Gln Leu Tyr Phe Ile Thr Gly Ala Asp Ala Leu Ala Gln Ile
        115                 120                 125

Val Thr Trp Arg Asp Trp Glu Lys Thr Phe Glu Leu Ala His Phe Val
    130                 135                 140

Gly Val Thr Arg Pro Gly Tyr Glu Leu Asp Gly Asn Ile Ile Pro Glu
145                 150                 155                 160

Met His Gln Asp Arg Val Ser Leu Val Asp Ile Pro Ala Met Ala Ile
                165                 170                 175

Ser Ser Thr Asp Cys Arg Glu Arg Ser Ser Glu Glu Arg Pro Val Trp
            180                 185                 190

Tyr Leu Val Pro Asp Gly Val Val Gln Tyr Ile Ala Lys Arg Gln Leu
```

```
        195                 200                 205

Tyr Arg Pro Glu Gly Ser Asp Lys Asp Met Asp Pro Lys Gly Gln Asn
    210                 215                 220

Gln Ala
225


<210> SEQ ID NO 66
<211> LENGTH: 249
<212> TYPE: PRT
<213> ORGANISM: Acinetobacter NudC enzyme, (NAD+ diphosphatase)

<400> SEQUENCE: 66

Met Ser Glu Leu Ser Leu Ala Tyr Ile Phe His Asn Gln Gln Leu Leu
1               5                   10                  15

Val Asn Glu Lys Leu Glu Leu Pro Lys Val Glu Thr Leu Ala Ser Asp
            20                  25                  30

Leu Gln Phe Gly Ser Gly Asp Asn Val Ile Ala Arg Asp Leu Gly Ala
        35                  40                  45

Asp Glu Thr Ile Pro Glu Gly Trp His Leu Val Ser Ile Arg Gln Leu
    50                  55                  60

Ile Ser Ser Trp Ser Thr Glu Glu Phe Met Arg Ala Ser Arg Ala Val
65                  70                  75                  80

Gln Leu Leu Glu Trp Arg Arg Asn His Lys Phe Cys Ser His Cys Gly
                85                  90                  95

His Glu Thr Glu Ile His Pro Thr Glu Tyr Ala Met Val Cys Pro Ala
            100                 105                 110

Cys Gln Tyr Arg Gln Tyr Pro Arg Val Gln Pro Cys Val Ile Thr Val
        115                 120                 125

Ile Thr Arg Gly Asp Asn Glu Ile Leu Leu Ala Lys Asn Ala Asn Asn
    130                 135                 140

Lys Ser Asn Met Tyr Gly Leu Ile Ala Gly Phe Val Glu Val Ala Glu
145                 150                 155                 160

Thr Leu Glu Glu Ala Val Gln Arg Glu Thr Leu Glu Glu Val Gly Leu
                165                 170                 175

Lys Leu Lys Asn Ile Arg Tyr Leu Ala Ser Gln Pro Trp Pro Phe Pro
            180                 185                 190

Ser Asn Leu Met Leu Ala Phe His Ala Glu Tyr Glu Ser Gly Asp Ile
        195                 200                 205

Lys Leu Gln Glu Glu Glu Ile Ser Asp Ala Gln Phe Phe Lys Phe Asp
    210                 215                 220

Gln Leu Pro Glu Ile Pro Phe Lys Gly Ser Ile Ala His Ala Met Ile
225                 230                 235                 240

Met His Val Ile Gln Lys Gln Pro Ile
                245


<210> SEQ ID NO 67
<211> LENGTH: 257
<212> TYPE: PRT
<213> ORGANISM: Escherichia coli NudC enzyme, (NAD+ diphosphatase)

<400> SEQUENCE: 67

Met Asp Arg Ile Ile Glu Lys Leu Asp His Gly Trp Trp Val Val Ser
1               5                   10                  15

His Glu Gln Lys Leu Trp Leu Pro Lys Gly Glu Leu Pro Tyr Gly Glu
            20                  25                  30

Ala Ala Asn Phe Asp Leu Val Gly Gln Arg Ala Leu Gln Ile Gly Glu
```

```
        35                  40                  45

Trp Gln Gly Glu Pro Val Trp Leu Val Gln Gln Gln Arg Arg His Asp
    50                  55                  60

Met Gly Ser Val Arg Gln Val Ile Asp Leu Asp Val Gly Leu Phe Gln
65                  70                  75                  80

Leu Ala Gly Arg Gly Val Gln Leu Ala Glu Phe Tyr Arg Ser His Lys
                85                  90                  95

Tyr Cys Gly Tyr Cys Gly His Glu Met Tyr Pro Ser Lys Thr Glu Trp
            100                 105                 110

Ala Met Leu Cys Ser His Cys Arg Glu Arg Tyr Tyr Pro Gln Ile Ala
        115                 120                 125

Pro Cys Ile Ile Val Ala Ile Arg Arg Asp Asp Ser Ile Leu Leu Ala
    130                 135                 140

Gln His Thr Arg His Arg Asn Gly Val His Thr Val Leu Ala Gly Phe
145                 150                 155                 160

Val Glu Val Gly Glu Thr Leu Glu Gln Ala Val Ala Arg Glu Val Met
                165                 170                 175

Glu Glu Ser Gly Ile Lys Val Lys Asn Leu Arg Tyr Val Thr Ser Gln
            180                 185                 190

Pro Trp Pro Phe Pro Gln Ser Leu Met Thr Ala Phe Met Ala Glu Tyr
        195                 200                 205

Asp Ser Gly Asp Ile Val Ile Asp Pro Lys Glu Leu Leu Glu Ala Asn
    210                 215                 220

Trp Tyr Arg Tyr Asp Asp Leu Pro Leu Leu Pro Pro Pro Gly Thr Val
225                 230                 235                 240

Ala Arg Arg Leu Ile Glu Asp Thr Val Ala Met Cys Arg Ala Glu Tyr
                245                 250                 255

Glu


<210> SEQ ID NO 68
<211> LENGTH: 238
<212> TYPE: PRT
<213> ORGANISM: Corynebacterium glutamicum NudC (a.k.a. Cg0888) enzyme,
      (NAD+ diphosphatase)

<400> SEQUENCE: 68

Met Arg Ile Leu Pro Ile Gly Pro His Asp Glu Ile Ala Val Asn Gly
1               5                   10                  15

Ser Ile Val Leu Leu Ser Glu His Asp Gly Asp Ile Val Ser Val Gly
            20                  25                  30

Pro Asp Leu Gly Thr Val Arg Val Thr Leu Glu Glu Ile Glu Ser Leu
        35                  40                  45

Gly Thr Pro Thr Ala Pro Arg Asp Leu Gly Ser Arg Glu Val Asp Ala
    50                  55                  60

Cys Val Ser Leu Leu Arg Asn Arg Glu Leu Val Arg Phe Asp Pro His
65                  70                  75                  80

Asp Gly Ser Glu Leu Thr Tyr Arg Glu His Ser Val Ala Tyr Gly Ala
                85                  90                  95

Ser Gly Lys Pro Leu Phe Pro Arg Leu Asp Pro Ala Val Ile Gly Ile
            100                 105                 110

Val Glu Leu Arg Gly Glu Asp Arg Leu Leu Leu Gly Met Asn Ala Gln
        115                 120                 125

Lys Arg Gln Arg Tyr Ser Leu Ile Ala Gly Tyr Val Ser His Gly Glu
    130                 135                 140
```

Ser Leu Glu Asp Ala Phe Thr Arg Glu Val Phe Glu Glu Ala Ala Arg
145 150 155 160

Arg Val Ser Glu Ile Ser Tyr Val Ser Ser Gln Pro Trp Pro Ile Ser
165 170 175

Gly Ser Leu Met Leu Gly Met Lys Gly Phe Thr Glu Asp Glu Leu Pro
180 185 190

Gln Gly Glu Thr Asp Gly Glu Leu Ala Glu Thr Ile Trp Ala Ser Pro
195 200 205

Leu Asp Ile Ile Asp Arg Lys Ile Pro Ile Ala Pro Pro Gly Ser Ile
210 215 220

Ala Tyr Asp Met Ile Asn Ala Trp Ala Arg Asp Lys Gln Asn
225 230 235

<210> SEQ ID NO 69
<211> LENGTH: 194
<212> TYPE: PRT
<213> ORGANISM: Burkholderiaceae NudC enzyme, (NAD+ diphosphatase)

<400> SEQUENCE: 69

Met Gln Tyr Arg Phe Cys Pro Gln Cys Gly Ala Pro Leu Glu Val Leu
1 5 10 15

Pro Leu Ser Gly Arg Glu Arg His Ala Cys Val Gln Gln Glu Cys Gly
20 25 30

Phe Val His Trp Asn Asn Pro Leu Pro Val Leu Ala Ala Val Val Glu
35 40 45

Tyr Gln Asp Lys Leu Leu Leu Ala Arg Asn Ala Ala Trp Pro Glu Thr
50 55 60

Met Phe Ala Leu Val Thr Gly Phe Leu Glu Arg Asp Glu Pro Pro Glu
65 70 75 80

Leu Gly Val Ala Arg Glu Leu Lys Glu Glu Thr Asn Leu Asp Thr Glu
85 90 95

Ser Val Ser Leu Ile Gly Val Tyr Glu Phe Met Arg Lys Asn Glu Leu
100 105 110

Ile Ile Ala Tyr His Val Lys Ala Thr Gly Thr Val Ala Leu Ser Glu
115 120 125

Glu Leu Ala Asp Tyr Lys Leu Val Ala Pro Glu Asp Val Arg Val Trp
130 135 140

Ser Ala Gly Thr Gly Phe Ala Val Ala Asp Trp Leu Ala Ala Arg Gly
145 150 155 160

Tyr Pro Val Arg Phe Phe Asp Arg Gln Thr Gly Ala Asp Ile Pro Asp
165 170 175

Pro Arg Arg Pro His Asp Phe Ser Leu Val Gly Gly Ser Leu Gln Tyr
180 185 190

Arg Trp

<210> SEQ ID NO 70
<211> LENGTH: 603
<212> TYPE: PRT
<213> ORGANISM: Haemophilus influenzae NadN (NAD+ diphosphatase)

<400> SEQUENCE: 70

Met Leu Leu Ser Lys Lys Ser Ala Thr Phe Ala Leu Ser Ala Phe Ala
1 5 10 15

Met Leu Phe Thr Ser Ala Ala Leu Ala Lys Glu Ala Pro Gln Ala His
20 25 30

Lys Ala Val Glu Leu Ser Ile Leu His Ile Asn Asp His His Ser Tyr

-continued

```
        35                  40                  45

Leu Glu Pro His Glu Thr Arg Ile Asn Leu Asn Gly Gln Gln Thr Lys
    50                  55                  60

Val Asp Ile Gly Gly Phe Ser Ala Val Asn Ala Lys Leu Asn Glu Leu
65                  70                  75                  80

Arg Lys Lys Tyr Lys Asn Pro Leu Val Leu His Ala Gly Asp Ala Ile
                85                  90                  95

Thr Gly Thr Leu Tyr Phe Thr Leu Phe Gly Gly Ser Ala Asp Ala Ala
            100                 105                 110

Val Met Asn Ala Gly Asn Phe His Tyr Phe Thr Leu Gly Asn His Glu
        115                 120                 125

Phe Asp Ala Gly Asn Glu Gly Leu Leu Lys Leu Leu Glu Pro Leu Lys
    130                 135                 140

Ile Pro Val Leu Ser Ala Asn Val Ile Pro Asp Lys Ser Ser Ile Leu
145                 150                 155                 160

Tyr Asn Lys Trp Lys Pro Tyr Asp Ile Phe Thr Val Asp Gly Glu Lys
                165                 170                 175

Ile Ala Ile Ile Gly Leu Asp Thr Val Asn Lys Thr Val Asn Ser Ser
            180                 185                 190

Ser Pro Gly Lys Asp Val Lys Phe Tyr Asp Glu Ile Ala Thr Ala Gln
        195                 200                 205

Ile Met Ala Asn Ala Leu Lys Gln Gln Gly Ile Asn Lys Ile Ile Leu
    210                 215                 220

Leu Ser His Ala Gly Ser Glu Lys Asn Ile Glu Ile Ala Gln Lys Val
225                 230                 235                 240

Asn Asp Ile Asp Val Ile Val Thr Gly Asp Ser His Tyr Leu Tyr Gly
                245                 250                 255

Asn Asp Glu Leu Arg Gly Leu Lys Leu Pro Val Ile Tyr Glu Tyr Pro
            260                 265                 270

Leu Glu Phe Lys Asn Pro Asn Gly Glu Pro Val Phe Val Met Glu Gly
        275                 280                 285

Trp Ala Tyr Ser Ala Val Val Gly Asp Leu Gly Val Lys Phe Ser Pro
    290                 295                 300

Gln Gly Ile Ala Ser Ile Thr Arg Lys Ile Pro His Val Leu Met Ser
305                 310                 315                 320

Ser His Lys Leu Gln Val Lys Asn Ser Glu Gly Lys Trp Ala Glu Leu
                325                 330                 335

Ala Gly Asp Glu Arg Lys Lys Ala Leu Asp Thr Leu Lys Ser Met Lys
            340                 345                 350

Ser Ile Ser Leu Asp Asp His Asp Ala Lys Thr Asp Lys Leu Ile Ala
        355                 360                 365

Lys Tyr Lys Ser Glu Lys Asp His Leu Ala Gln Glu Ile Val Gly Val
    370                 375                 380

Ile Thr Gly Ser Ala Met Pro Gly Gly Ser Ala Asn Arg Ile Pro Asn
385                 390                 395                 400

Lys Ala Gly Ser Asn Pro Glu Gly Ser Ile Ala Thr Arg Phe Ile Ala
                405                 410                 415

Glu Thr Met Tyr Asn Glu Leu Lys Thr Val Asp Leu Thr Ile Gln Asn
            420                 425                 430

Ala Gly Gly Val Arg Ala Asp Ile Leu Pro Gly Asn Val Thr Phe Asn
        435                 440                 445

Asp Ala Tyr Thr Phe Leu Pro Phe Gly Asn Thr Leu Tyr Thr Tyr Lys
    450                 455                 460
```

-continued

Met Glu Gly Ser Leu Val Lys Gln Val Leu Glu Asp Ala Met Gln Phe
465 470 475 480

Ala Leu Val Asp Gly Ser Thr Gly Ala Phe Pro Tyr Gly Ala Gly Ile
485 490 495

Arg Tyr Glu Ala Asn Glu Thr Pro Asn Ala Glu Gly Lys Arg Leu Val
500 505 510

Ser Val Glu Val Leu Asn Lys Gln Thr Gln Gln Trp Glu Pro Ile Asp
515 520 525

Asp Asn Lys Arg Tyr Leu Val Gly Thr Asn Ala Tyr Val Ala Gly Gly
530 535 540

Lys Asp Gly Tyr Lys Thr Phe Gly Lys Leu Phe Asn Asp Pro Lys Tyr
545 550 555 560

Glu Gly Val Asp Thr Tyr Leu Pro Asp Ala Glu Ser Phe Ile Lys Phe
565 570 575

Met Lys Lys His Pro His Phe Glu Ala Tyr Thr Ser Ser Asn Val Lys
580 585 590

Phe Asn Ala Ser Thr Asp Ala Leu Pro Lys Lys
595 600

<210> SEQ ID NO 71
<211> LENGTH: 397
<212> TYPE: PRT
<213> ORGANISM: Bs168|nupG_purine_nucleoside_transport_protein

<400> SEQUENCE: 71

Met Tyr Phe Leu Leu Asn Leu Val Gly Leu Ile Val Ile Met Ala Val
1 5 10 15

Val Phe Leu Cys Ser Pro Gln Lys Lys Lys Ile Lys Trp Arg Pro Ile
20 25 30

Ile Thr Leu Ile Val Leu Glu Leu Leu Ile Thr Trp Phe Met Leu Gly
35 40 45

Thr Lys Val Gly Ser Trp Ala Ile Gly Lys Ile Gly Asp Phe Phe Thr
50 55 60

Trp Leu Ile Ala Cys Ala Ser Asp Gly Ile Ala Phe Ala Phe Pro Ser
65 70 75 80

Val Met Ala Asn Glu Thr Val Asp Phe Phe Phe Ser Ala Leu Leu Pro
85 90 95

Ile Ile Phe Ile Val Thr Phe Phe Asp Ile Leu Thr Tyr Phe Gly Ile
100 105 110

Leu Pro Trp Leu Ile Asp Lys Ile Gly Trp Val Ile Ser Lys Ala Ser
115 120 125

Arg Leu Pro Lys Leu Glu Ser Phe Phe Ser Ile Gln Met Met Phe Leu
130 135 140

Gly Asn Thr Glu Ala Leu Ala Val Ile Arg Gln Gln Leu Thr Val Leu
145 150 155 160

Ser Asn Asn Arg Leu Leu Thr Phe Gly Leu Met Ser Met Ser Ser Ile
165 170 175

Ser Gly Ser Ile Ile Gly Ser Tyr Leu Ser Met Val Pro Ala Thr Tyr
180 185 190

Val Phe Thr Ala Ile Pro Leu Asn Cys Leu Asn Ala Leu Ile Ile Ala
195 200 205

Asn Leu Leu Asn Pro Val His Val Pro Glu Asp Glu Asp Ile Ile Tyr
210 215 220

Thr Pro Pro Lys Glu Glu Lys Lys Asp Phe Phe Ser Thr Ile Ser Asn

-continued

```
225                 230                 235                 240

Ser Met Leu Val Gly Met Asn Met Val Ile Val Ile Leu Ala Met Val
                245                 250                 255

Ile Gly Tyr Val Ala Leu Thr Ser Ala Val Asn Gly Ile Leu Gly Val
            260                 265                 270

Phe Val His Gly Leu Thr Ile Gln Thr Ile Phe Ala Tyr Leu Phe Ser
        275                 280                 285

Pro Phe Ala Phe Leu Leu Gly Leu Pro Val His Asp Ala Met Tyr Val
    290                 295                 300

Ala Gln Leu Met Gly Met Lys Leu Ala Thr Asn Glu Phe Val Ala Met
305                 310                 315                 320

Leu Asp Leu Lys Asn Asn Leu Lys Ser Leu Pro Pro His Thr Val Ala
                325                 330                 335

Val Ala Thr Thr Phe Leu Thr Ser Phe Ala Asn Phe Ser Thr Val Gly
            340                 345                 350

Met Ile Tyr Gly Thr Tyr Asn Ser Ile Leu Asp Gly Glu Lys Ser Thr
        355                 360                 365

Val Ile Gly Arg Asn Val Trp Lys Leu Leu Val Ser Gly Ile Ala Val
    370                 375                 380

Ser Leu Leu Ser Ala Ala Ile Val Gly Leu Phe Val Trp
385                 390                 395


<210> SEQ ID NO 72
<211> LENGTH: 233
<212> TYPE: PRT
<213> ORGANISM: Bs168|deoD_-_purine_nucleoside_phosphorylase

<400> SEQUENCE: 72

Met Ser Val His Ile Gly Ala Glu Lys Gly Gln Ile Ala Asp Thr Val
1               5                   10                  15

Leu Leu Pro Gly Asp Pro Leu Arg Ala Lys Phe Ile Ala Glu Thr Tyr
            20                  25                  30

Leu Glu Asn Val Glu Cys Tyr Asn Glu Val Arg Gly Met Tyr Gly Phe
        35                  40                  45

Thr Gly Thr Tyr Lys Gly Lys Lys Ile Ser Val Gln Gly Thr Gly Met
    50                  55                  60

Gly Val Pro Ser Ile Ser Ile Tyr Val Asn Glu Leu Ile Gln Ser Tyr
65                  70                  75                  80

Asp Val Gln Asn Leu Ile Arg Val Gly Ser Cys Gly Ala Ile Arg Lys
                85                  90                  95

Asp Val Lys Val Arg Asp Val Ile Leu Ala Met Thr Ser Ser Thr Asp
            100                 105                 110

Ser Gln Met Asn Arg Val Ala Phe Gly Ser Val Asp Phe Ala Pro Cys
        115                 120                 125

Ala Asp Phe Glu Leu Leu Lys Asn Ala Tyr Asp Ala Ala Lys Asp Lys
    130                 135                 140

Gly Val Pro Val Thr Val Gly Ser Val Phe Thr Ala Asp Gln Phe Tyr
145                 150                 155                 160

Asn Asp Asp Ser Gln Ile Glu Lys Leu Ala Lys Tyr Gly Val Leu Gly
                165                 170                 175

Val Glu Met Glu Thr Thr Ala Leu Tyr Thr Leu Ala Ala Lys His Gly
            180                 185                 190

Arg Lys Ala Leu Ser Ile Leu Thr Val Ser Asp His Val Leu Thr Gly
        195                 200                 205
```

Glu Glu Thr Thr Ala Glu Glu Arg Gln Thr Thr Phe His Asp Met Ile
210 215 220

Glu Val Ala Leu His Ser Val Ser Gln
225 230

<210> SEQ ID NO 73
<211> LENGTH: 433
<212> TYPE: PRT
<213> ORGANISM: Bs168|pdp_-_pyrimidine-nucleoside_phosphorylase

<400> SEQUENCE: 73

Met Arg Met Val Asp Ile Ile Ile Lys Lys Gln Asn Gly Lys Glu Leu
1 5 10 15

Thr Thr Glu Glu Ile Gln Phe Phe Val Asn Gly Tyr Thr Asp Gly Ser
20 25 30

Ile Pro Asp Tyr Gln Ala Ser Ala Leu Ala Met Ala Ile Phe Phe Gln
35 40 45

Asp Met Ser Asp Arg Glu Arg Ala Asp Leu Thr Met Ala Met Val Asn
50 55 60

Ser Gly Glu Thr Ile Asp Leu Ser Ala Ile Glu Gly Ile Lys Val Asp
65 70 75 80

Lys His Ser Thr Gly Gly Val Gly Asp Thr Thr Thr Leu Val Leu Ala
85 90 95

Pro Leu Val Ala Ala Leu Asp Val Pro Val Ala Lys Met Ser Gly Arg
100 105 110

Gly Leu Gly His Thr Gly Gly Thr Ile Asp Lys Leu Glu Ala Ile Met
115 120 125

Gly Phe His Val Glu Leu Thr Lys Asp Glu Phe Ile Lys Leu Val Asn
130 135 140

Arg Asp Lys Val Ala Val Ile Gly Gln Ser Gly Asn Leu Thr Pro Ala
145 150 155 160

Asp Lys Lys Leu Tyr Ala Leu Arg Asp Val Thr Gly Thr Val Asn Ser
165 170 175

Ile Pro Leu Ile Ala Ser Ser Ile Met Ser Lys Lys Ile Ala Ala Gly
180 185 190

Ala Asp Ala Ile Val Leu Asp Val Lys Thr Gly Ala Gly Ala Phe Met
195 200 205

Lys Thr Glu Glu Asp Ala Ala Glu Leu Ala Lys Ala Met Val Arg Ile
210 215 220

Gly Asn Asn Val Gly Arg Gln Thr Met Ala Val Ile Ser Asp Met Ser
225 230 235 240

Gln Pro Leu Gly Phe Ala Ile Gly Asn Ala Leu Glu Val Lys Glu Ala
245 250 255

Ile Asp Thr Leu Lys Gly Glu Gly Pro Glu Asp Leu His Glu Leu Val
260 265 270

Leu Thr Leu Gly Ser Gln Met Val Val Leu Ala Lys Lys Ala Asp Thr
275 280 285

Leu Asp Glu Ala Arg Ala Lys Leu Glu Glu Val Met Lys Asn Gly Lys
290 295 300

Ala Leu Glu Lys Phe Lys Asp Phe Leu Lys Asn Gln Gly Gly Asp Ser
305 310 315 320

Ser Ile Val Asp Asp Pro Ser Lys Leu Pro Gln Ala Ala Tyr Gln Ile
325 330 335

Asp Val Pro Ala Lys Glu Ala Gly Val Val Ser Glu Ile Val Ala Asp
340 345 350

```
Glu Ile Gly Val Ala Ala Met Leu Leu Gly Ala Gly Arg Ala Thr Lys
        355                 360                 365

Glu Asp Glu Ile Asp Leu Ala Val Gly Ile Met Leu Arg Lys Lys Val
    370                 375                 380

Gly Asp Lys Val Glu Lys Gly Glu Pro Leu Val Thr Leu Tyr Ala Asn
385                 390                 395                 400

Arg Glu Asn Val Asp Glu Val Ile Ala Lys Val Tyr Asp Asn Ile Arg
                405                 410                 415

Ile Ala Ala Glu Ala Lys Ala Pro Lys Leu Ile His Thr Leu Ile Thr
            420                 425                 430

Glu
```

<210> SEQ ID NO 74
<211> LENGTH: 271
<212> TYPE: PRT
<213> ORGANISM: Bs168|pupG_-_purine_nucleoside_phosphorylase

<400> SEQUENCE: 74

```
Met Lys Asp Arg Ile Glu Arg Ala Ala Ala Phe Ile Lys Gln Asn Leu
1               5                   10                  15

Pro Glu Ser Pro Lys Ile Gly Leu Ile Leu Gly Ser Gly Leu Gly Ile
            20                  25                  30

Leu Ala Asp Glu Ile Glu Asn Pro Val Lys Leu Lys Tyr Glu Asp Ile
        35                  40                  45

Pro Glu Phe Pro Val Ser Thr Val Glu Gly His Ala Gly Gln Leu Val
    50                  55                  60

Leu Gly Thr Leu Glu Gly Val Ser Val Ile Ala Met Gln Gly Arg Phe
65                  70                  75                  80

His Phe Tyr Glu Gly Tyr Ser Met Glu Lys Val Thr Phe Pro Val Arg
                85                  90                  95

Val Met Lys Ala Leu Gly Val Glu Ala Leu Ile Val Thr Asn Ala Ala
            100                 105                 110

Gly Gly Val Asn Thr Glu Phe Arg Ala Gly Asp Leu Met Ile Ile Thr
        115                 120                 125

Asp His Ile Asn Phe Met Gly Thr Asn Pro Leu Ile Gly Pro Asn Glu
    130                 135                 140

Ala Asp Phe Gly Ala Arg Phe Pro Asp Met Ser Ser Ala Tyr Asp Lys
145                 150                 155                 160

Asp Leu Ser Ser Leu Ala Glu Lys Ile Ala Lys Asp Leu Asn Ile Pro
                165                 170                 175

Ile Gln Lys Gly Val Tyr Thr Ala Val Thr Gly Pro Ser Tyr Glu Thr
            180                 185                 190

Pro Ala Glu Val Arg Phe Leu Arg Thr Met Gly Ser Asp Ala Val Gly
        195                 200                 205

Met Ser Thr Val Pro Glu Val Ile Val Ala Asn His Ala Gly Met Arg
    210                 215                 220

Val Leu Gly Ile Ser Cys Ile Ser Asn Ala Ala Ala Gly Ile Leu Asp
225                 230                 235                 240

Gln Pro Leu Ser His Asp Glu Val Met Glu Val Thr Glu Lys Val Lys
                245                 250                 255

Ala Gly Phe Leu Lys Leu Val Lys Ala Ile Val Ala Gln Tyr Glu
            260                 265                 270
```

<210> SEQ ID NO 75

-continued

<211> LENGTH: 239
<212> TYPE: PRT
<213> ORGANISM: gnl|ECOLI|DEOD-MONOMER purine nucleoside phosphorylase

<400> SEQUENCE: 75

```
Met Ala Thr Pro His Ile Asn Ala Glu Met Gly Asp Phe Ala Asp Val
1               5                   10                  15

Val Leu Met Pro Gly Asp Pro Leu Arg Ala Lys Tyr Ile Ala Glu Thr
            20                  25                  30

Phe Leu Glu Asp Ala Arg Glu Val Asn Asn Val Arg Gly Met Leu Gly
        35                  40                  45

Phe Thr Gly Thr Tyr Lys Gly Arg Lys Ile Ser Val Met Gly His Gly
    50                  55                  60

Met Gly Ile Pro Ser Cys Ser Ile Tyr Thr Lys Glu Leu Ile Thr Asp
65                  70                  75                  80

Phe Gly Val Lys Lys Ile Ile Arg Val Gly Ser Cys Gly Ala Val Leu
                85                  90                  95

Pro His Val Lys Leu Arg Asp Val Val Ile Gly Met Gly Ala Cys Thr
            100                 105                 110

Asp Ser Lys Val Asn Arg Ile Arg Phe Lys Asp His Asp Phe Ala Ala
        115                 120                 125

Ile Ala Asp Phe Asp Met Val Arg Asn Ala Val Asp Ala Ala Lys Ala
    130                 135                 140

Leu Gly Ile Asp Ala Arg Val Gly Asn Leu Phe Ser Ala Asp Leu Phe
145                 150                 155                 160

Tyr Ser Pro Asp Gly Glu Met Phe Asp Val Met Glu Lys Tyr Gly Ile
                165                 170                 175

Leu Gly Val Glu Met Glu Ala Ala Gly Ile Tyr Gly Val Ala Ala Glu
            180                 185                 190

Phe Gly Ala Lys Ala Leu Thr Ile Cys Thr Val Ser Asp His Ile Arg
        195                 200                 205

Thr His Glu Gln Thr Thr Ala Ala Glu Arg Gln Thr Thr Phe Asn Asp
    210                 215                 220

Met Ile Lys Ile Ala Leu Glu Ser Val Leu Leu Gly Asp Lys Glu
225                 230                 235
```

<210> SEQ ID NO 76
<211> LENGTH: 211
<212> TYPE: PRT
<213> ORGANISM: gnl|CORYNE|G18NG-MONOMER nucleoside phosphorylase

<400> SEQUENCE: 76

```
Met Lys Leu Phe Gln Ser Cys Phe Leu Leu Asn Asn Ser Ala Cys Asn
1               5                   10                  15

Leu Leu Val Val Leu Cys Leu Val Thr Met Thr Glu Thr Leu Phe Val
            20                  25                  30

Ser Ala Thr Thr Glu Glu Ala Val Tyr Leu Pro Asp Gly Ile Asp Leu
        35                  40                  45

Leu Val Thr Gly Ile Gly Thr Thr Ala Ala Thr Met Ile Leu Thr Lys
    50                  55                  60

Glu Leu Ala Thr Arg Glu Val Leu Pro Ala Arg Ile Val Asn Ile Gly
65                  70                  75                  80

Thr Ala Gly Ala Leu Val Asp Gly Leu Ala Gly Val Tyr Glu Ile Glu
                85                  90                  95

Tyr Val Leu Gln His Asp Phe Ser Ser Glu Leu Ile Ala Glu Met Thr
            100                 105                 110
```

```
Gly Lys Pro Cys Ser Asn Gly Ser Thr Leu Ala Thr Ser Gly His Phe
        115                 120                 125

Pro Val Ala Ser Leu Ala Thr Gly Asn Ser Phe Ile Ala Asp Ser Glu
    130                 135                 140

Thr Arg Asn His Leu Ala Thr Arg Ala Ser Leu Cys Asp Met Glu Gly
145                 150                 155                 160

Ala Ala Leu Val Gly Val Ala Lys His Phe Gly Val Pro Ile Thr Leu
                165                 170                 175

Leu Lys Gln Val Ser Asp Ser Ala Asp Glu Glu Ala Ser Gly Ser Trp
            180                 185                 190

Phe Asp Ala Val Asp Ala Gly Ala Arg Gln Leu Ala Glu Ala Val Lys
        195                 200                 205

Glu Phe Lys
    210


<210> SEQ ID NO 77
<211> LENGTH: 346
<212> TYPE: PRT
<213> ORGANISM: Escherichia coli NadA (quinolate synthase)

<400> SEQUENCE: 77

Met Ser Val Met Phe Asp Pro Asp Thr Ala Ile Tyr Pro Phe Pro Pro
1               5                   10                  15

Lys Pro Thr Pro Leu Ser Ile Asp Glu Lys Ala Tyr Tyr Arg Glu Lys
            20                  25                  30

Ile Lys Arg Leu Leu Lys Glu Arg Asn Ala Val Met Val Ala His Tyr
        35                  40                  45

Tyr Thr Asp Pro Glu Ile Gln Gln Leu Ala Glu Glu Thr Gly Gly Cys
    50                  55                  60

Ile Ser Asp Ser Leu Glu Met Ala Arg Phe Gly Ala Lys His Pro Ala
65                  70                  75                  80

Ser Thr Leu Leu Val Ala Gly Val Arg Phe Met Gly Glu Thr Ala Lys
                85                  90                  95

Ile Leu Ser Pro Glu Lys Thr Ile Leu Met Pro Thr Leu Gln Ala Glu
            100                 105                 110

Cys Ser Leu Asp Leu Gly Cys Pro Val Glu Glu Phe Asn Ala Phe Cys
        115                 120                 125

Asp Ala His Pro Asp Arg Thr Val Val Val Tyr Ala Asn Thr Ser Ala
    130                 135                 140

Ala Val Lys Ala Arg Ala Asp Trp Val Val Thr Ser Ser Ile Ala Val
145                 150                 155                 160

Glu Leu Ile Asp His Leu Asp Ser Leu Gly Glu Lys Ile Ile Trp Ala
                165                 170                 175

Pro Asp Lys His Leu Gly Arg Tyr Val Gln Lys Gln Thr Gly Gly Asp
            180                 185                 190

Ile Leu Cys Trp Gln Gly Ala Cys Ile Val His Asp Glu Phe Lys Thr
        195                 200                 205

Gln Leu Thr Arg Leu Gln Glu Glu Tyr Pro Asp Ala Ala Ile Leu Val
    210                 215                 220

His Pro Glu Ser Pro Gln Ala Ile Val Asp Met Ala Asp Ala Val Gly
225                 230                 235                 240

Ser Thr Ser Gln Leu Ile Ala Ala Ala Lys Thr Leu Pro His Gln Arg
                245                 250                 255

Leu Ile Val Ala Thr Asp Arg Gly Ile Phe Tyr Lys Met Gln Gln Ala
```

-continued

```
            260                 265                 270

Val Pro Asp Lys Glu Leu Leu Glu Ala Pro Thr Ala Gly Glu Gly Ala
        275                 280                 285

Thr Cys Arg Ser Cys Ala His Cys Pro Trp Met Ala Met Asn Gly Leu
    290                 295                 300

Gln Ala Ile Ala Glu Ala Leu Glu Gln Glu Gly Ser Asn His Glu Val
305                 310                 315                 320

His Val Asp Glu Arg Leu Arg Glu Arg Ala Leu Val Pro Leu Asn Arg
                325                 330                 335

Met Leu Asp Phe Ala Ala Thr Leu Arg Gly
            340                 345


<210> SEQ ID NO 78
<211> LENGTH: 368
<212> TYPE: PRT
<213> ORGANISM: Bacillus subtilis NadA (quinolate synthase)

<400> SEQUENCE: 78

Met Ser Ile Leu Asp Val Ile Lys Gln Ser Asn Asp Met Met Pro Glu
1               5                   10                  15

Ser Tyr Lys Glu Leu Ser Arg Lys Asp Met Glu Thr Arg Val Ala Ala
            20                  25                  30

Ile Lys Lys Lys Phe Gly Ser Arg Leu Phe Ile Pro Gly His His Tyr
        35                  40                  45

Gln Lys Asp Glu Val Ile Gln Phe Ala Asp Gln Thr Gly Asp Ser Leu
    50                  55                  60

Gln Leu Ala Gln Val Ala Glu Lys Asn Lys Glu Ala Asp Tyr Ile Val
65                  70                  75                  80

Phe Cys Gly Val His Phe Met Ala Glu Thr Ala Asp Met Leu Thr Ser
                85                  90                  95

Glu Gln Gln Thr Val Val Leu Pro Asp Met Arg Ala Gly Cys Ser Met
            100                 105                 110

Ala Asp Met Ala Asp Met Gln Gln Thr Asn Arg Ala Trp Lys Lys Leu
        115                 120                 125

Gln His Ile Phe Gly Asp Thr Ile Ile Pro Leu Thr Tyr Val Asn Ser
    130                 135                 140

Thr Ala Glu Ile Lys Ala Phe Val Gly Lys His Gly Gly Ala Thr Val
145                 150                 155                 160

Thr Ser Ser Asn Ala Lys Lys Val Leu Glu Trp Ala Phe Thr Gln Lys
                165                 170                 175

Lys Arg Ile Leu Phe Leu Pro Asp Gln His Leu Gly Arg Asn Thr Ala
            180                 185                 190

Tyr Asp Leu Gly Ile Ala Leu Glu Asp Met Ala Val Trp Asp Pro Met
        195                 200                 205

Lys Asp Glu Leu Val Ala Glu Ser Gly His Thr Asn Val Lys Val Ile
    210                 215                 220

Leu Trp Lys Gly His Cys Ser Val His Glu Lys Phe Thr Thr Lys Asn
225                 230                 235                 240

Ile His Asp Met Arg Glu Arg Asp Pro Asp Ile Gln Ile Ile Val His
                245                 250                 255

Pro Glu Cys Ser His Glu Val Val Thr Leu Ser Asp Asp Asn Gly Ser
            260                 265                 270

Thr Lys Tyr Ile Ile Asp Thr Ile Asn Gln Ala Pro Ala Gly Ser Lys
        275                 280                 285
```

-continued

Trp Ala Ile Gly Thr Glu Met Asn Leu Val Gln Arg Ile Ile His Glu
290 295 300

His Pro Asp Lys Gln Ile Glu Ser Leu Asn Pro Asp Met Cys Pro Cys
305 310 315 320

Leu Thr Met Asn Arg Ile Asp Leu Pro His Leu Leu Trp Ser Leu Glu
325 330 335

Gln Ile Glu Lys Gly Glu Pro Ser Gly Val Ile Lys Val Pro Lys Ala
340 345 350

Ile Gln Glu Asp Ala Leu Leu Ala Leu Asn Arg Met Leu Ser Ile Thr
355 360 365

<210> SEQ ID NO 79
<211> LENGTH: 428
<212> TYPE: PRT
<213> ORGANISM: Corynebacterium glutamicum NadA (quinolate synthase)

<400> SEQUENCE: 79

Met Thr Thr Ser Ile Thr Pro Ser Val Asn Leu Ala Leu Lys Asn Ala
1 5 10 15

Asn Ser Cys Asn Ser Glu Leu Lys Asp Gly Pro Trp Phe Leu Asp Gln
20 25 30

Pro Gly Met Pro Asp Val Tyr Gly Pro Gly Ala Ser Gln Asn Asp Pro
35 40 45

Ile Pro Ala His Ala Pro Arg Gln Gln Val Leu Pro Glu Glu Tyr Gln
50 55 60

Arg Ala Ser Asp Asp Glu Leu His Arg Arg Ile Arg Glu Ala Lys Asp
65 70 75 80

Thr Leu Gly Asp Lys Val Val Ile Leu Gly His Phe Tyr Gln Arg Asp
85 90 95

Glu Val Ile Gln His Ala Asp Phe Val Gly Asp Ser Phe Gln Leu Ala
100 105 110

Arg Ala Ala Lys Thr Arg Pro Glu Ala Glu Ala Ile Val Phe Cys Gly
115 120 125

Val His Phe Met Ala Glu Thr Ala Asp Leu Leu Ser Thr Asp Glu Gln
130 135 140

Ser Val Ile Leu Pro Asn Leu Ala Ala Gly Cys Ser Met Ala Asp Met
145 150 155 160

Ala Asp Leu Asp Ser Val Glu Asp Cys Trp Glu Gln Leu Thr Ser Ile
165 170 175

Tyr Gly Asp Asp Thr Leu Ile Pro Val Thr Tyr Met Asn Ser Ser Ala
180 185 190

Ala Leu Lys Gly Phe Val Gly Glu His Gly Gly Ile Val Cys Thr Ser
195 200 205

Ser Asn Ala Arg Ser Val Leu Glu Trp Ala Phe Glu Arg Gly Gln Arg
210 215 220

Val Leu Phe Phe Pro Asp Gln His Leu Gly Arg Asn Thr Ala Lys Ala
225 230 235 240

Met Gly Ile Gly Ile Asp Gln Met Pro Leu Trp Asn Pro Asn Lys Pro
245 250 255

Leu Gly Gly Asn Thr Val Ser Glu Leu Glu Asn Ala Lys Val Leu Leu
260 265 270

Trp His Gly Phe Cys Ser Val His Lys Arg Phe Thr Val Glu Gln Ile
275 280 285

Asn Lys Ala Arg Ala Glu Tyr Pro Asp Val His Val Ile Val His Pro
290 295 300

Glu Ser Pro Met Pro Val Val Asp Ala Ala Asp Ser Ser Gly Ser Thr
305 310 315 320

Asp Phe Ile Val Lys Ala Ile Gln Ala Ala Pro Ala Gly Ser Thr Phe
325 330 335

Ala Ile Gly Thr Glu Ile Asn Leu Val Gln Arg Leu Ala Ala Gln Tyr
340 345 350

Pro Gln His Thr Ile Phe Cys Leu Asp Pro Val Ile Cys Pro Cys Ser
355 360 365

Thr Met Tyr Arg Ile His Pro Gly Tyr Leu Ala Trp Ala Leu Glu Glu
370 375 380

Leu Val Ala Gly Asn Val Ile Asn Gln Ile Ser Val Ser Glu Ser Val
385 390 395 400

Ala Ala Pro Ala Arg Val Ala Leu Glu Arg Met Leu Ser Val Val Pro
405 410 415

Ala Ala Pro Val Thr Pro Ser Ser Ser Lys Asp Ala
420 425

<210> SEQ ID NO 80
<211> LENGTH: 540
<212> TYPE: PRT
<213> ORGANISM: Escherichia coli NadB (L-aspartate oxidase)

<400> SEQUENCE: 80

Met Asn Thr Leu Pro Glu His Ser Cys Asp Val Leu Ile Ile Gly Ser
1 5 10 15

Gly Ala Ala Gly Leu Ser Leu Ala Leu Arg Leu Ala Asp Gln His Gln
20 25 30

Val Ile Val Leu Ser Lys Gly Pro Val Thr Glu Gly Ser Thr Phe Tyr
35 40 45

Ala Gln Gly Gly Ile Ala Ala Val Phe Asp Glu Thr Asp Ser Ile Asp
50 55 60

Ser His Val Glu Asp Thr Leu Ile Ala Gly Ala Gly Ile Cys Asp Arg
65 70 75 80

His Ala Val Glu Phe Val Ala Ser Asn Ala Arg Ser Cys Val Gln Trp
85 90 95

Leu Ile Asp Gln Gly Val Leu Phe Asp Thr His Ile Gln Pro Asn Gly
100 105 110

Glu Glu Ser Tyr His Leu Thr Arg Glu Gly Gly His Ser His Arg Arg
115 120 125

Ile Leu His Ala Ala Asp Ala Thr Gly Arg Glu Val Glu Thr Thr Leu
130 135 140

Val Ser Lys Ala Leu Asn His Pro Asn Ile Arg Val Leu Glu Arg Ser
145 150 155 160

Asn Ala Val Asp Leu Ile Val Ser Asp Lys Ile Gly Leu Pro Gly Thr
165 170 175

Arg Arg Val Val Gly Ala Trp Val Trp Asn Arg Asn Lys Glu Thr Val
180 185 190

Glu Thr Cys His Ala Lys Ala Val Val Leu Ala Thr Gly Gly Ala Ser
195 200 205

Lys Val Tyr Gln Tyr Thr Thr Asn Pro Asp Ile Ser Ser Gly Asp Gly
210 215 220

Ile Ala Met Ala Trp Arg Ala Gly Cys Arg Val Ala Asn Leu Glu Phe
225 230 235 240

Asn Gln Phe His Pro Thr Ala Leu Tyr His Pro Gln Ala Arg Asn Phe

-continued

```
                245                 250                 255

Leu Leu Thr Glu Ala Leu Arg Gly Glu Gly Ala Tyr Leu Lys Arg Pro
            260                 265                 270

Asp Gly Thr Arg Phe Met Pro Asp Phe Asp Glu Arg Gly Glu Leu Ala
        275                 280                 285

Pro Arg Asp Ile Val Ala Arg Ala Ile Asp His Glu Met Lys Arg Leu
    290                 295                 300

Gly Ala Asp Cys Met Phe Leu Asp Ile Ser His Lys Pro Ala Asp Phe
305                 310                 315                 320

Ile Arg Gln His Phe Pro Met Ile Tyr Glu Lys Leu Leu Gly Leu Gly
                325                 330                 335

Ile Asp Leu Thr Gln Glu Pro Val Pro Ile Val Pro Ala Ala His Tyr
            340                 345                 350

Thr Cys Gly Gly Val Met Val Asp Asp His Gly Arg Thr Asp Val Glu
        355                 360                 365

Gly Leu Tyr Ala Ile Gly Glu Val Ser Tyr Thr Gly Leu His Gly Ala
    370                 375                 380

Asn Arg Met Ala Ser Asn Ser Leu Leu Glu Cys Leu Val Tyr Gly Trp
385                 390                 395                 400

Ser Ala Ala Glu Asp Ile Thr Arg Arg Met Pro Tyr Ala His Asp Ile
                405                 410                 415

Ser Thr Leu Pro Pro Trp Asp Glu Ser Arg Val Glu Asn Pro Asp Glu
            420                 425                 430

Arg Val Val Ile Gln His Asn Trp His Glu Leu Arg Leu Phe Met Trp
        435                 440                 445

Asp Tyr Val Gly Ile Val Arg Thr Thr Lys Arg Leu Glu Arg Ala Leu
    450                 455                 460

Arg Arg Ile Thr Met Leu Gln Gln Glu Ile Asp Glu Tyr Tyr Ala His
465                 470                 475                 480

Phe Arg Val Ser Asn Asn Leu Leu Glu Leu Arg Asn Leu Val Gln Val
                485                 490                 495

Ala Glu Leu Ile Val Arg Cys Ala Met Met Arg Lys Glu Ser Arg Gly
            500                 505                 510

Leu His Phe Thr Leu Asp Tyr Pro Glu Leu Leu Thr His Ser Gly Pro
        515                 520                 525

Ser Ile Leu Ser Pro Gly Asn His Tyr Ile Asn Arg
    530                 535                 540


<210> SEQ ID NO 81
<211> LENGTH: 531
<212> TYPE: PRT
<213> ORGANISM: Bacillus subtilis NadB (L-aspartate oxidase)

<400> SEQUENCE: 81

Met Ser Lys Lys Thr Ile Ala Val Ile Gly Ser Gly Ala Ala Ala Leu
1               5                   10                  15

Ser Leu Ala Ala Ala Phe Pro Pro Ser Tyr Glu Val Thr Val Ile Thr
            20                  25                  30

Lys Lys Ser Val Lys Asn Ser Asn Ser Val Tyr Ala Gln Gly Gly Ile
        35                  40                  45

Ala Ala Ala Tyr Ala Lys Asp Asp Ser Ile Glu Ala His Leu Glu Asp
    50                  55                  60

Thr Leu Tyr Ala Gly Cys Gly His Asn Asn Leu Ala Ile Val Ala Asp
65                  70                  75                  80
```

-continued

```
Val Leu His Asp Gly Lys Met Met Val Gln Ser Leu Leu Glu Arg Gly
                85                  90                  95

Phe Pro Phe Asp Arg Asn Glu Arg Gly Gly Val Cys Leu Gly Arg Glu
            100                 105                 110

Gly Ala His Ser Tyr Asn Arg Ile Phe His Ala Gly Gly Asp Ala Thr
        115                 120                 125

Gly Arg Leu Leu Ile Asp Tyr Leu Leu Lys Arg Ile Asn Ser Lys Ile
    130                 135                 140

Lys Leu Ile Glu Asn Glu Thr Ala Ala Asp Leu Leu Ile Glu Asp Gly
145                 150                 155                 160

Arg Cys Ile Gly Val Met Thr Lys Asp Ser Lys Gly Arg Leu Lys Val
                165                 170                 175

Arg His Ala Asp Glu Val Val Leu Ala Ala Gly Gly Cys Gly Asn Leu
            180                 185                 190

Phe Leu His His Thr Asn Asp Leu Thr Val Thr Gly Asp Gly Leu Ser
        195                 200                 205

Leu Ala Tyr Arg Ala Gly Ala Glu Leu Thr Asp Leu Glu Phe Thr Gln
    210                 215                 220

Phe His Pro Thr Leu Leu Val Lys Asn Gly Val Ser Tyr Gly Leu Val
225                 230                 235                 240

Ser Glu Ala Val Arg Gly Glu Gly Gly Cys Leu Val Asp Glu Asn Gly
                245                 250                 255

Arg Arg Ile Met Ala Glu Arg His Pro Leu Gly Asp Leu Ala Pro Arg
            260                 265                 270

Asp Ile Val Ser Arg Val Ile His Glu Glu Met Ala Lys Gly Asn Arg
        275                 280                 285

Val Tyr Ile Asp Phe Ser Ala Ile Ser Asp Phe Glu Thr Arg Phe Pro
    290                 295                 300

Thr Ile Thr Ala Ile Cys Glu Lys Ala Gly Ile Asp Ile His Ser Gly
305                 310                 315                 320

Lys Ile Pro Val Ala Pro Gly Met His Phe Leu Met Gly Gly Val Ser
                325                 330                 335

Val Asn Arg Trp Gly Glu Thr Thr Val Pro Gly Leu Tyr Ala Ile Gly
            340                 345                 350

Glu Thr Ala Cys Ser Gly Leu His Gly Ala Asn Arg Leu Ala Ser Asn
        355                 360                 365

Ser Leu Leu Glu Ala Leu Val Phe Gly Lys Arg Ala Ala Glu His Ile
    370                 375                 380

Ile Gln Lys Pro Val Tyr Asn Arg Gln Tyr Gln Ser Gly Leu Glu Thr
385                 390                 395                 400

Ser Val Phe Tyr Glu Val Pro Asp Ile Glu Gly His Glu Leu Gln Ser
                405                 410                 415

Lys Met Thr Ser His Met Ser Ile Leu Arg Glu Gln Ser Ser Leu Ile
            420                 425                 430

Glu Leu Ser Ile Trp Leu His Thr Leu Pro Phe Gln Glu Val Asn Val
        435                 440                 445

Lys Asp Ile Thr Ile Arg Gln Met Glu Leu Ser His Leu Trp Gln Thr
    450                 455                 460

Ala Lys Leu Met Thr Phe Ser Ala Leu Leu Arg Glu Glu Ser Arg Gly
465                 470                 475                 480

Ala His Phe Arg Thr Asp Phe Pro His Ala Glu Val Ser Trp Gln Gly
                485                 490                 495

Arg Gln Ile Val His Thr Lys Lys Gly Thr Lys Ile Arg Lys Asn Glu
```

```
            500                 505                 510

Gly Ile Trp Asn Asn Glu Ser Phe Thr Ala Glu Lys Ile Thr Glu Ser
        515                 520                 525

Leu Phe Ser
    530
```

<210> SEQ ID NO 82
<211> LENGTH: 297
<212> TYPE: PRT
<213> ORGANISM: Escherichia coli NadC (quinolate phosphoribosyl transferase)

<400> SEQUENCE: 82

```
Met Pro Pro Arg Arg Tyr Asn Pro Asp Thr Arg Arg Asp Glu Leu Leu
1               5                   10                  15

Glu Arg Ile Asn Leu Asp Ile Pro Gly Ala Val Ala Gln Ala Leu Arg
            20                  25                  30

Glu Asp Leu Gly Gly Thr Val Asp Ala Asn Asn Asp Ile Thr Ala Lys
        35                  40                  45

Leu Leu Pro Glu Asn Ser Arg Ser His Ala Thr Val Ile Thr Arg Glu
    50                  55                  60

Asn Gly Val Phe Cys Gly Lys Arg Trp Val Glu Glu Val Phe Ile Gln
65                  70                  75                  80

Leu Ala Gly Asp Asp Val Thr Ile Ile Trp His Val Asp Asp Gly Asp
                85                  90                  95

Val Ile Asn Ala Asn Gln Ser Leu Phe Glu Leu Glu Gly Pro Ser Arg
            100                 105                 110

Val Leu Leu Thr Gly Glu Arg Thr Ala Leu Asn Phe Val Gln Thr Leu
        115                 120                 125

Ser Gly Val Ala Ser Lys Val Arg His Tyr Val Glu Leu Leu Glu Gly
    130                 135                 140

Thr Asn Thr Gln Leu Leu Asp Thr Arg Lys Thr Leu Pro Gly Leu Arg
145                 150                 155                 160

Ser Ala Leu Lys Tyr Ala Val Leu Cys Gly Gly Gly Ala Asn His Arg
                165                 170                 175

Leu Gly Leu Ser Asp Ala Phe Leu Ile Lys Glu Asn His Ile Ile Ala
            180                 185                 190

Ser Gly Ser Val Arg Gln Ala Val Glu Lys Ala Ser Trp Leu His Pro
        195                 200                 205

Asp Ala Pro Val Glu Val Glu Val Glu Asn Leu Glu Glu Leu Asp Glu
    210                 215                 220

Ala Leu Lys Ala Gly Ala Asp Ile Ile Met Leu Asp Asn Phe Glu Thr
225                 230                 235                 240

Glu Gln Met Arg Glu Ala Val Lys Arg Thr Asn Gly Lys Ala Leu Leu
                245                 250                 255

Glu Val Ser Gly Asn Val Thr Asp Lys Thr Leu Arg Glu Phe Ala Glu
            260                 265                 270

Thr Gly Val Asp Phe Ile Ser Val Gly Ala Leu Thr Lys His Val Gln
        275                 280                 285

Ala Leu Asp Leu Ser Met Arg Phe Arg
    290                 295
```

<210> SEQ ID NO 83
<211> LENGTH: 289
<212> TYPE: PRT
<213> ORGANISM: Bacillus subtilis NadC (quinolate phosphoribosyl transferase)

<400> SEQUENCE: 83

Met Asn His Leu Gln Leu Lys Lys Leu Leu Asn His Phe Phe Leu Glu
1 5 10 15

Asp Ile Gly Thr Gly Asp Leu Thr Ser Gln Ser Ile Phe Gly Glu Gln
20 25 30

Ser Cys Glu Ala Glu Ile Val Ala Lys Ser Glu Gly Ile Phe Ala Gly
35 40 45

Ala Ala Ile Ile Lys Glu Gly Phe Ser Leu Leu Asp Glu Asn Val Gln
50 55 60

Ser Ile Leu His Lys Lys Asp Gly Asp Met Leu His Lys Gly Glu Val
65 70 75 80

Ile Ala Glu Leu His Gly Pro Ala Ala Ala Leu Leu Ser Gly Glu Arg
85 90 95

Val Val Leu Asn Leu Ile Gln Arg Leu Ser Gly Ile Ala Thr Met Thr
100 105 110

Arg Glu Ala Val Arg Cys Leu Asp Asp Glu Gln Ile Lys Ile Cys Asp
115 120 125

Thr Arg Lys Thr Thr Pro Gly Leu Arg Met Leu Glu Lys Tyr Ala Val
130 135 140

Arg Ala Gly Gly Gly Tyr Asn His Arg Phe Gly Leu Tyr Asp Gly Ile
145 150 155 160

Met Ile Lys Asp Asn His Ile Ala Ala Cys Gly Ser Ile Leu Glu Ala
165 170 175

Cys Lys Lys Ala Arg Gln Ala Ala Gly His Met Val Asn Ile Glu Val
180 185 190

Glu Ile Glu Thr Glu Glu Gln Leu Arg Glu Ala Ile Ala Ala Gly Ala
195 200 205

Asp Val Ile Met Phe Asp Asn Cys Pro Pro Asp Thr Val Arg His Phe
210 215 220

Ala Lys Leu Thr Pro Ala Asn Ile Lys Thr Glu Ala Ser Gly Gly Ile
225 230 235 240

Thr Leu Glu Ser Leu Pro Ala Phe Lys Gly Thr Gly Val Asn Tyr Ile
245 250 255

Ser Leu Gly Phe Leu Thr His Ser Val Lys Ser Leu Asp Ile Ser Met
260 265 270

Asp Val Thr Leu Ser Asn Glu Ser Val Glu Glu Cys Cys Tyr Val Asn
275 280 285

Ser

<210> SEQ ID NO 84
<211> LENGTH: 279
<212> TYPE: PRT
<213> ORGANISM: Corynebacterium glutamicum NadC (quinolate
phosphoribosyl transferase)

<400> SEQUENCE: 84

Met Thr Thr His Ile Asp Arg Ile Val Gly Ala Ala Leu Ser Glu Asp
1 5 10 15

Ala Pro Trp Gly Asp Ile Thr Ser Asp Thr Phe Ile Pro Gly Ser Ala
20 25 30

Gln Leu Ser Ala Lys Val Val Ala Arg Glu Pro Gly Val Phe Ser Gly
35 40 45

Gln Ala Leu Phe Asp Ala Ser Phe Arg Leu Val Asp Pro Arg Ile Asn

```
    50                  55                  60

Ala Ser Leu Lys Val Ala Asp Gly Asp Ser Phe Glu Thr Gly Asp Ile
65                  70                  75                  80

Leu Gly Thr Ile Thr Gly Ser Ala Arg Ser Ile Leu Arg Ser Glu Arg
                85                  90                  95

Ile Ala Leu Asn Phe Ile Gln Arg Thr Ser Gly Ile Ala Thr Leu Thr
            100                 105                 110

Ser Cys Tyr Val Ala Glu Val Lys Gly Thr Lys Ala Arg Ile Val Asp
        115                 120                 125

Thr Arg Lys Thr Thr Pro Gly Leu Arg Ile Ile Glu Arg Gln Ala Val
    130                 135                 140

Arg Asp Gly Gly Gly Phe Asn His Arg Ala Thr Leu Ser Asp Ala Val
145                 150                 155                 160

Met Val Lys Asp Asn His Leu Ala Ala Ile Ala Ser Gln Gly Leu Ser
                165                 170                 175

Ile Thr Glu Ala Leu Ser Asn Met Lys Ala Lys Leu Pro His Thr Thr
            180                 185                 190

His Val Glu Val Glu Val Asp His Ile Glu Gln Ile Glu Pro Val Leu
        195                 200                 205

Ala Ala Gly Val Asp Thr Ile Met Leu Asp Asn Phe Thr Ile Asp Gln
    210                 215                 220

Leu Ile Glu Gly Val Asp Leu Ile Gly Gly Arg Ala Leu Val Glu Ala
225                 230                 235                 240

Ser Gly Gly Val Asn Leu Asn Thr Ala Gly Lys Ile Ala Ser Thr Gly
                245                 250                 255

Val Asp Val Ile Ser Val Gly Ala Leu Thr His Ser Val His Ala Leu
            260                 265                 270

Asp Leu Gly Leu Asp Ile Phe
        275


<210> SEQ ID NO 85
<211> LENGTH: 20
<212> TYPE: DNA
<213> ORGANISM: Primer 10444

<400> SEQUENCE: 85

cggtaagtcc cgtctagcct                                                  20


<210> SEQ ID NO 86
<211> LENGTH: 25
<212> TYPE: DNA
<213> ORGANISM: Primer 10447

<400> SEQUENCE: 86

atgtttgcaa aacgattcaa aacct                                            25


<210> SEQ ID NO 87
<211> LENGTH: 37
<212> TYPE: DNA
<213> ORGANISM: Primer 11222

<400> SEQUENCE: 87

ttacaccgaa tttctaataa taaccgggca ggccatg                               37


<210> SEQ ID NO 88
<211> LENGTH: 37
<212> TYPE: DNA
<213> ORGANISM: Primer 11223
```

<400> SEQUENCE: 88
ggcctgcccg gttattatta gaaattcggt gtaagag 37

<210> SEQ ID NO 89
<211> LENGTH: 40
<212> TYPE: DNA
<213> ORGANISM: Primer 11226

<400> SEQUENCE: 89
cttttacacc gaatttttaa taataaccgg gcaggccatg 40

<210> SEQ ID NO 90
<211> LENGTH: 37
<212> TYPE: DNA
<213> ORGANISM: Primer 11227

<400> SEQUENCE: 90
ggcctgcccg gttattatta aaaattcggt gtaaaag 37

<210> SEQ ID NO 91
<211> LENGTH: 40
<212> TYPE: DNA
<213> ORGANISM: Primer 11230

<400> SEQUENCE: 91
cggatgaagc ggaatgttaa taataaccgg gcaggccatg 40

<210> SEQ ID NO 92
<211> LENGTH: 37
<212> TYPE: DNA
<213> ORGANISM: Primer 11231

<400> SEQUENCE: 92
ggcctgcccg gttattatta acattccgct tcatccg 37

<210> SEQ ID NO 93
<211> LENGTH: 38
<212> TYPE: DNA
<213> ORGANISM: Primer 11232

<400> SEQUENCE: 93
gaaaggtggt gaactactat gaaaacagca gcatacgc 38

<210> SEQ ID NO 94
<211> LENGTH: 40
<212> TYPE: DNA
<213> ORGANISM: Primer 11233

<400> SEQUENCE: 94
gcgtatgctg ctgttttcat agtagttcac cacctttctc 40

<210> SEQ ID NO 95
<211> LENGTH: 40
<212> TYPE: DNA
<213> ORGANISM: Primer 11234

<400> SEQUENCE: 95
cacttacacc gaacttctaa taataaccgg gcaggccatg 40

<210> SEQ ID NO 96
<211> LENGTH: 37
<212> TYPE: DNA

<213> ORGANISM: Primer 11235

<400> SEQUENCE: 96
ggcctgcccg gttattatta gaagttcggt gtaagtg 37

<210> SEQ ID NO 97
<211> LENGTH: 33
<212> TYPE: DNA
<213> ORGANISM: Primer 11341

<400> SEQUENCE: 97
aagggaggtt tcatatgaaa attgttaaag att 33

<210> SEQ ID NO 98
<211> LENGTH: 37
<212> TYPE: DNA
<213> ORGANISM: Primer 11342

<400> SEQUENCE: 98
tttaacaatt ttcatatgaa acctccctta attctcg 37

<210> SEQ ID NO 99
<211> LENGTH: 35
<212> TYPE: DNA
<213> ORGANISM: Primer 11351

<400> SEQUENCE: 99
gtgaactact atgaaaattg taaaaaactt tattg 35

<210> SEQ ID NO 100
<211> LENGTH: 35
<212> TYPE: DNA
<213> ORGANISM: Primer 11352

<400> SEQUENCE: 100
ttacaatttt catagtagtt caccaccttt ctcta 35

<210> SEQ ID NO 101
<211> LENGTH: 35
<212> TYPE: DNA
<213> ORGANISM: Primer 11353

<400> SEQUENCE: 101
aagggaggtt tcatatgaaa atcgttaaag acttc 35

<210> SEQ ID NO 102
<211> LENGTH: 35
<212> TYPE: DNA
<213> ORGANISM: Primer 11354

<400> SEQUENCE: 102
taacgatttt catatgaaac ctcccttaat tctcg 35

<210> SEQ ID NO 103
<211> LENGTH: 36
<212> TYPE: DNA
<213> ORGANISM: Primer 11159

<400> SEQUENCE: 103
gctacttact ctcgagttac tttttccaga aatcat 36

<210> SEQ ID NO 104
<211> LENGTH: 33

-continued

```
<212> TYPE: DNA
<213> ORGANISM: Primer 11160

<400> SEQUENCE: 104

gctaacttag catatgatga cattgcaaca aca                                33
```

MICROBIAL PRODUCTION OF NICOTAMIDE RIBOSIDE

CROSS-REFERENCE TO RELATED APPLICATIONS

This application is the U.S. national phase of International Application No. PCT/US2016/061905 filed Nov. 14, 2016 which designated the U.S. and claims the benefit of the filing date of U.S. Provisional Patent Application No. 62/254,736 filed Nov. 13, 2015, the entire contents of each of which are hereby incorporated herein by reference in their entireties.

FIELD OF THE INVENTION

Embodiments of the present disclosure relate to novel methods for the production of nicotinamide riboside and expression vectors and host cells useful in such methods.

BACKGROUND OF THE INVENTION

Nicotinamide riboside (NR) is a pyridine-nucleoside form of vitamin B3 that functions as a precursor to nicotinamide adenine dinucleotide or NAD+. It is believed that high dose nicotinic acid can help to elevate high-density lipoprotein cholesterol, lowers low-density lipoprotein cholesterol and lower free fatty acids, although its mechanism has not been completely understood. Nicotinamide riboside has been synthesized chemically in the past. The biological pathways leading to the synthesis of nicotinamide riboside are known but producing nicotinamide riboside biologically remains a challenge. Thus, it is desirable to identify new methods for producing nicotinamide riboside more efficiently.

The biosynthesis of NAD+ in bacteria was first elucidated in the 1990s, and was shown to depend on two key enzymatic activities which are not found in eukaryotes: an FAD dependent L-aspartate oxidase (NadB, EC 1.4.3.16); and a quinolate synthase (NadA, EC 2.5.1.72) (Flachmann, 1988, *European Journal of Biochemistry,* 175(2), 221-228). NadB catalyzes the oxidation of L-aspartate to iminosuccinate, utilizing molecular oxygen as an electron acceptor and producing hydrogen peroxide, with the involvement of a loosely bound flavin adenine dinucleotide (FAD) cofactor (Seifert, 1990, *Biological chemistry Hoppe-Seyler,* 371(1), 239-248). The enzyme in *Esherichia coli* is known to be inhibited by the downstream product NAD+ (Nasu S, 1982, *J Biol Chem,* 257(2), 626-32), but feedback resistant mutants have been generated (Hughes, 1983, *J Bacteriol,* 154(3), 1126-36). NadA, which contains an iron-sulfur cluster, subsequently carries out the condensation and cyclization of iminosuccinate with dihydroxyacetone phosphate yielding quinolate (Flachmann, 1988). The combined activity of these two enzymes will produce one mole of quinolate from one mole of aspartate and one mole of dihydroxyacetone phosphate.

Three further enzymatic activities are common to the two canonical de novo pathways of NAD+ synthesis: quinolate phosphoribosyltransferase (NadC, EC 2.4.2.19); nicotinic acid mononucleotide adenyltransferase (NadD, EC 2.7.7.18); and NAD+ synthetase (NadE, EC 6.3.1.5). NadC transfers the phosphoribosyl moiety from phophoribosylpyrophosphate to the quinolate nitrogen and catalyzes the subsequent decarboxylation of the intermediate to produce nicotinic acid mononucleotide (NaMN), pyrophosphate, and carbon dioxide (Begley, 2001, *Vitamins & Hormones,* 61, 103-119). NadD uses adenine triphosphate (ATP) to adenylate NaMN, producing nicotinic acid dinucleotide (NaAD) and pyrophosphate (Begley, 2001). NadD is also capable of adenylating nicotinamide dinucleotide (NMN), but has lower affinity (higher $K_m$) and lower turnover ($V_{max}$) than when using NaMN as substrate. For example, the enzyme from *Bacillus subtilis* has a $V_{max}/K_m$ for NaMN which is 104 times higher than its $V_{max}/K_m$ for NMN (Olland, 2002, *J Biol Chem,* 277(5), 3698-3707). The final step in NAD+ biosynthesis is catalyzed by NadE, which utilizes either ammonia or glutamine as a nitrogen donor to amidate NaAD to NAD+, hydrolyzing one mole of ATP to AMP and pyrophosphate (Begley, 2001). Similar to NadD's substrate flexibility, this enzyme can act on NaMN in place of NaAD to produce NMN, but again, the substrate preference is strong; in *Bacillus anthracis* the difference in $V_{max}/K_m$ is >103 fold (Sorci, 2009, *J Biol Chem,* 277(5), 3698-3707).

In contrast to the canonical pathway described above, the pathway in *Francisella tularensis* proceeds via NMN as an intermediate (Sorci, 2009). Following formation of NaMN, the FtNadE* enzyme catalyzes its amidation using $NH_3$ in a mechanism apparently analogous to the typical NadE enzyme, i.e., with concomitant hydrolysis of one mole of ATP (referred to herein as NadE* activity). The FtNadE* enzyme will also amidate NaAD, but is more specific for NaMN, with a 60 fold difference in the relative values for $V_{max}/K_m$. The final step is catalyzed by a NadM enzyme, which catalyzes the adenylation of NMN.

In addition to the de novo pathways, there exist multiple pathways for the salvage of NMN, NR, nicotinamide (Nam) or nicotinic acid (NA) (Gazzaniga, 2009, *Microbiol Mol Biol Rev,* 73(3), 529-541). NMN is recycled to NaMN by action of a nicotinamide nucleotide amidase (*E. coli* PncC, *B. subtilis* CinA, EC 3.5.1.42); NR is phosphorylated to NMN by a nicotinamide riboside kinase (*E. coli* NadR, EC 2.7.1.22) or degraded to Nam and phosphoribose by a purine nucleoside phosphorylase in a reversible reaction (*E. coli* DeoD, *B. subtilis* DeoD, PupG, Pdp, EC 2.4.2.1); Nam can be phosphoribosylated to NMN by DeoD or deamidated to NA by nicotinamidase (PncA, EC 3.5.1.19); and NA or Nam is converted to NaMN or NMN, respectively by nicotinate phosphoribosyl transferase (*E. coli* PncB, *B. subtilis* YueK EC 6.3.4.21). Extracellular NMN is dephosphorylated to NR by a periplasmic acid phosphatase (*E. coli* UshA, *B. subtilis* YfkN, EC 3.1.3.5) and extracellular NR can be imported by the NR transporter (*E. coli* PnuC, *B. subtilis* NupG). NAD+ itself can be used as a source for pyrimidine nucleotides. NAD+ is cleaved to NMN and adenosine monophosphate by the activity of NAD+ diphosphatase (NudC, EC 3.6.1.22).

Expression of nad genes is typically co-regulated in bacteria by a transcriptional repressor. In *E. coli*, transcription of nadA, nadB, and pncB is repressed by the NadR protein, which also has catalytic activities that contribute to salvage pathways (Raffaelli, 1999, *J Bacteriol,* 181(17), 5509-5511). NadR blocks transcription by binding to a conserved motif in the presence of NAD+. In *Bacillus subtilis*, a different protein named YrxA performs a similar role, by blocking the transcription of two divergently transcribed operons, nadB-nadA-nadC and nifS-yrxA, in the presence of NA (Rossolillo, 2005, *J Bacteriol,* 187(20), 7155-7160).

The inventors have now surprisingly found a novel method for significantly increasing the production rate of nicotinamide ribose and created expression vectors and host cells useful in such methods.

SUMMARY OF THE INVENTION

The present invention is directed to a genetically modified bacterium capable of producing nicotinamide riboside (NR), wherein the bacterium comprises at least one modification selected from a group consisting of: a) adding the activity of a heterologous nicotinic acid amidating protein (NadE*); and b) adding or increasing the activity of a nicotinamide adenine dinucleotide (NAD+) hydrolyzing protein, wherein the bacterium with said at least one modification produces an increased amount of NR than the bacterium without any of said modifications.

In some embodiments, the genetically modified bacterium may further comprise one or more additional modifications selected from the group consisting of: a) blocking or reducing the activity of a protein which functions to repress NAD+ biosynthesis by repressing transcription of nadA, nadB, nadC genes or combinations thereof; b) blocking or reducing the activity of a protein which functions as a nicotinamide riboside transporter protein; c) blocking or reducing the activity of a protein which functions as a nicotinic acid mononucleotide adenyltransferase; d) blocking or reducing the activity of a protein which functions as a nicotinamide mononucleotide amidohydrolase; e) blocking or reducing the activity of a protein which functions as a purine nucleoside phosphorylase; f) adding or increasing the activity of a protein which functions as a nicotinamide mononucleotide hydrolase; and g) adding or increasing the transcription of a gene which encodes L-aspartate oxidase, quinolate synthase, quinolate phoshoribosyltransferase, or combinations thereof.

The present invention is also directed to a method for producing NR, comprising: culturing a bacterium cell under conditions effective to produce NR and recovering NR from the medium and thereby producing NR, wherein the host microorganism comprises at least one modification selected from the group consisting of: a) adding the activity of a heterologous heterologous nicotinic acid amidating protein (NadE*); b) adding or increasing the activity of a nicotinamide adenine dinucleotide (NAD+) hydrolyzing protein; c) blocking or reducing the activity of a protein which functions as a negative regulator transcription of nadA, nadB, nadC or combinations thereof; d) blocking or reducing the activity of a protein which functions as a nicotinamide riboside transporter protein; e) blocking or reducing the activity of a protein which functions as a nicotinic acid mononucleotide adenyltransferase; f) blocking or reducing the activity of a protein which functions as a nicotinamide mononucleotide amidohydrolase; g) blocking or reducing the activity of a protein which functions as a purine nucleoside phosphorylase; h) adding or increasing the activity of a protein which functions as a nicotinamide mononucleotide hydrolase; and i) adding or increasing the transcription of a gene which encodes L-aspartate oxidase, quinolate synthase, quinolate phoshoribosyltransferase, or combinations thereof.

The present invention is directed to another method for producing NR, comprising: culturing a bacterium cell under conditions effective to produce NR and recovering NR from the medium and thereby producing NR, wherein the host microorganism comprises at least one modification selected from the group consisting of: a) adding the activity of a heterologous nicotinic acid amidating protein NadE*; and b) adding or increasing the activity of a nicotinamide adenine dinucleotide (NAD+) hydrolyzing protein. In this method, the bacterium cell may further comprise at least one modification selected from the group consisting of: a) blocking or reducing the activity of a protein which functions to repress NAD+ biosynthesis by repressing transcription of nadA, nadB, nadC genes or combinations thereof; b) blocking or reducing the activity of a protein which functions as a nicotinamide riboside transporter protein; c) blocking or reducing the activity of a protein which functions as a nicotinic acid mononucleotide adenyltransferase; d) blocking or reducing the activity of a protein which functions as a nicotinamide mononucleotide amidohydrolase; e) blocking or reducing the activity of a protein which functions as a purine nucleoside phosphorylase; f) adding or increasing the activity of a protein which functions as a nicotinamide mononucleotide hydrolase; and g) adding or increasing the transcription of a gene which encodes L-aspartate oxidase, quinolate synthase, quinolate phoshoribosyltransferase, or combinations thereof.

In some embodiments, the NadE* protein is a polypeptide comprising an amino acid sequence at least 50%, at least 60%, at least 70%, at least 80%, at least 90%, at least 95%, at least 97%, or at least 99% identical to any of SEQ ID NOs: 1 and 3 to 18, wherein said polypeptide has a nicotinic acid amidating activity for converting nicotinic acid mononucleotide to nicotinamide mononucleotide.

In some embodiments, the above NadE* protein further has one or more of the following conserved amino acids when compared with the reference amino acid sequence of SEQ ID NO:1: a) tyrosine at position 287, b) glutamine at position 133, and c) arginine at position 236, based on the ClustalW method of alignment when compared to SEQ ID NOS: 1 and 3 to 18 using the default parameters of GAP PENALTY=10, GAP LENGTH PENALTY=0.1, and Gonnet 250 series of protein weight matrix.

In some embodiments, the nicotinamide adenine dinucleotide (NAD+) hydrolyzing protein is a polypeptide comprising an amino acid sequence at least 50%, at least 60%, at least 70%, at least 80%, at least 90%, at least 95%, at least 97%, or at least 99% identical to any one of SEQ ID NOs: 66 to 70 wherein said polypeptide has an NAD+ hydrolyzing activity for converting NAD+ to nicotinamide mononucleotide and adenine.

In some embodiments, the negative regulator of NAD+ biosynthesis is a polypeptide comprising an amino acid sequence of either SEQ ID NO: 51, 52, or 53, or a variant of said polypeptide, wherein said polypeptide has an activity for repressing NAD+ biosynthesis.

In some embodiments, the nicotinamide riboside transporter is a polypeptide comprising an amino acid sequence any one of SEQ ID NOs: 54, 55, 56, or 71 wherein said polypeptide has a nicotinamide riboside transport activity for importing nicotinamide riboside.

In some embodiments, the nucleoside hydrolase is a polypeptide comprising an amino acid sequence any one of SEQ ID NOs: 57, 58, or 59, or a variant of said polypeptide, wherein said polypeptide has a nucleoside hydrolase activity for converting nicotinamide mononucleotide to nicotinamide riboside.

In some embodiments, the nicotinic acid mononucleotide adenyltransferase protein is a polypeptide comprising an amino acid sequence of either SEQ ID NOs: 63, 64, or 65, or a variant of said polypeptide, wherein said polypeptide has a nicotinic acid mononucleotide adenyltransferase activity for converting nicotinic acid mononucleotide to nicotinic acid adenine dinucleotide.

In some embodiments, the nicotinamide mononucleotide amidohydrolase protein is a polypeptide comprising an amino acid sequence of any one of SEQ ID NOs: 60, 61, or 62, or a variant of said polypeptide, wherein said polypeptide has a nicotinamide mononucleotide amidohydrolase activity for converting nicotinamide mononucleotide to nicotinic acid mononucleotide.

In some embodiments, the purine nucleoside phosphorylase; protein is a polypeptide comprising an amino acid sequence of any one of SEQ ID NOs: 72 to 76 wherein said polypeptide has a purine nucleoside phosphorylase activity for converting nicotinamide riboside and phosphate to nicotinamide and ribose-1-phosphate. In some embodiments, the quinolate synthase is a polypeptide comprising an amino acid sequence of any one of SEQ ID NO: 77, 78, or 79, or a variant of said polypeptide, wherein said polypeptide has an activity of converting iminosuccinic acid and dihydroxyacetone phosphate to quinolate and phosphate.

In some embodiments, the L-aspartate oxidase is a polypeptide comprising an amino acid sequence of any one of SEQ ID NO: 80 or 81 or a variant of said polypeptide, wherein said polypeptide has an activity of converting aspartic acid to iminosuccinic acid in an FAD dependent reaction.

In some embodiments, the quinolate phosphoribosyltransferase is a polypeptide comprising an amino acid sequence of any one of SEQ ID NO: 82, 83, or 84 or a variant of said polypeptide, wherein said polypeptide has an activity of converting quinolate and phosphoribosylpyrophosphate to nicotinamide mononucleotide and carbon dioxide.

The present invention is also directed to a genetically modified bacterium characterized by that as a result of the genetic modification, the bacterium produces NR and can accumulate the produced NR to at least 100 mg/L in the fermentation broth in which the bacterium is grown.

In some embodiments, in the genetically modified bacterium, the genetic modification is selected from a group consisting of: a) adding the activity of a heterologous nicotinic acid amidating protein (NadE*); and b) adding or increasing the activity of a nicotinamide adenine dinucleotide (NAD+) hydrolyzing protein. In some embodiment, the genetic modification further comprises one or more additional modifications selected from the group consisting of: a) blocking or reducing the activity of a protein which functions to repress NAD+ biosynthesis by repressing transcription of nadA, nadB, nadC genes or combinations thereof; b) blocking or reducing the activity of a protein which functions as a nicotinamide riboside transporter protein; c) blocking or reducing the activity of a protein which functions as a nicotinic acid mononucleotide adenyltransferase; d) blocking or reducing the activity of a protein which functions as a nicotinamide mononucleotide amidohydrolase; e) blocking or reducing the activity of a protein with function as a purine nucleoside phosphorylase; f) adding or increasing the activity of a protein which functions as a nicotinamide mononucleotide hydrolase; and g) adding or increasing the activity of a protein which functions as a L-aspartate oxidase, a quinolate synthase, a quinolate phoshoribosyltransferase, or combinations thereof.

In some embodiment, in the above bacterium of genetically modified bacterium, the NadE* protein is a polypeptide comprising an amino acid sequence at least 50%, at least 60%, at least 70%, at least 80%, at least 90%, at least 95%, at least 97%, or at least 99% identical to any one of SEQ ID NOs: 1 and 3 to 18, wherein said polypeptide has a nicotinic acid amidating activity for converting nicotinic acid mononucleotide to nicotinamide mononucleotide. In one embodiment, the NadE* protein has one or more of the following conserved amino acids when compared with the reference amino acid sequence of SEQ ID NO:1: a) tyrosine at position 27, b) glutamine at position 1343, and c) arginine at position 2376, based on the ClustalW method of alignment when compared to SEQ ID NOS: 1 and 3 to 18 using the default parameters of GAP PENALTY=10, GAP LENGTH PENALTY=0.1, and Gonnet 250 series of protein weight matrix.

In one embodiment, the nicotinamide adenine dinucleotide (NAD+) hydrolyzing protein is a polypeptide comprising an amino acid sequence at least 50%, at least 60%, at least 70%, at least 80%, at least 90%, at least 95%, at least 97%, or at least 99% identical to any one of SEQ ID NOs: 66 to 70, wherein said polypeptide has an NAD+ hydrolyzing activity for converting NAD+ to nicotinamide mononucleotide and adenine.

In some embodiments, the genetically modified bacterium may be an *E. coli, B. subtilis*, a *C. glutamicum*, an *A. baylyi* or a *R. eutropha.*

The present invention is also directed to nicotinamide riboside compounds obtained from any of the above mentioned genetically modified bacterium.

The present invention is also directed to a composition comprising the nicotinamide riboside compounds obtained from the above-mentioned genetically modified bacterium.

The present invention is also directed to a food product or feed comprising the nicotinamide riboside compounds obtained from the above-mentioned genetically modified bacterium.

Overview of the Sequence Listing

The nucleic acid sequences listed in the accompanying sequence listing are shown using standard letter abbreviation for nucleotide bases. Only one strand of each nucleic acid sequence is shown, but the complementary strand is understood to be included by any reference to the displayed strand. In the accompanying sequence listing:

SEQ ID NO: 1 is the amino acid sequence encoding the *Francisella tularensis* NadE* enzyme (FtNadE*), which is a nicotinic acid amidating protein.

SEQ ID NO: 2 is the nucleotide sequence encoding the *Francisella tularensis* NadE* enzyme (FtNadE*) open reading frame.

SEQ ID NO: 3 is the amino acid sequence encoding the *Francisella* sp. FSC1006 NadE* enzyme (FspFNadE*), which is a nicotinic acid amidating protein SEQ ID NO: 4 is the amino acid sequence encoding the *Francisella* guangzhouensis NadE* enzyme (FgNadE*), which is a nicotinic acid amidating protein SEQ ID NO: 5 is the amino acid sequence encoding the *Francisella* sp. TX077308 NadE* enzyme (FspTNadE*), which is a nicotinic acid amidating protein SEQ ID NO: 6 is the amino acid sequence encoding the *Francisella philomiragia* subsp. *philomiragia* ATCC 25017 NadE* enzyme (FphNadE*), which is a nicotinic acid amidating protein SEQ ID NO: 7 is the amino acid sequence encoding the *Francisella philomiragia* strain O #319-036 [FSC 153] NadE* enzyme, which is a predicted nicotinic acid amidating protein SEQ ID NO: 8 is the amino acid sequence encoding the *Francisella noatunensis* supbsp. *orientalis* str. Toba 04 NadE* enzyme, which is a predicted nicotinic acid amidating protein SEQ ID NO: 9 is the amino acid sequence encoding the *Francisella philomiragia* strain GA01-2794 NadE* enzyme, which is a predicted nicotinic acid amidating protein SEQ ID NO: 10 is the amino acid sequence encoding the *Francisella persica* ATCC VR-331 NadE* enzyme (FpeNadE*), which is a nicotinic acid amidating protein SEQ ID NO: 11 is the amino acid sequence encoding the *Francisella* cf. *novicida* 3523 NadE* enzyme (FnNadE*), which is a nicotinic acid amidating protein SEQ ID NO: 12 is the amino acid sequence encoding the *Francisella tularensis* subsp. *novicida* D9876 NadE* enzyme, which is a predicted nicotinic acid amidating protein SEQ ID NO: 13 is the amino acid sequence encoding the *Francisella tularensis* subsp. *novicida* F6168 NadE* enzyme, which is a predicted nicotinic acid amidating protein SEQ ID NO: 14 is the amino acid sequence encoding the *Francisella tularensis* subsp. *tularensis* strain NIH B-38 NadE* enzyme, which is a predicted nicotinic acid amidating protein SEQ ID NO: 15 is the amino acid sequence encoding the *Francisella tularensis* subsp. holarctica F92 NadE* enzyme, which is a predicted nicotinic acid amidating protein SEQ ID NO: 16 is the amino acid sequence encoding the *Dichelobacter nodosus* VCS1703A NadE* enzyme (DnNadE*), which is a nicotinic acid amidating protein.

SEQ ID NO: 17 is the amino acid sequence encoding the *Mannheimia succinoproducens* MBEL55E NadE* enzyme (MnNadE*), which is a nicotinic acid amidating protein.

SEQ ID NO: 18 is the amino acid sequence encoding the *Actinobacillus succinogenes* NadE* enzyme (AsNadE*), which is a nicotinic acid amidating protein.

SEQ ID NO: 19 is the nucleotide sequence encoding the *Mannheimia succinoproducens* MBEL55E NadE* enzyme (MnNadE*) open reading frame.

SEQ ID NO: 20 is the nucleotide sequence encoding the *Dichelobacter nodosus* VCS1703A NadE* enzyme (DnNadE*) open reading frame.

SEQ ID NO: 21 is the nucleotide sequence encoding the *Actinobacillus succinogenes* NadE* enzyme (AsNadE*) open reading frame.

SEQ ID NO: 22 is the nucleotide sequence encoding the *Francisella philomiragia* subsp. *philomiragia* ATCC 25017 NadE* enzyme (FphNadE*) open reading frame.

SEQ ID NO: 23 is the nucleotide sequence encoding the *Francisella* cf. *novicida* 3523 NadE* enzyme (FnNadE*) open reading frame.

SEQ ID NO: 24 is the nucleotide sequence encoding the *Francisella* sp. TX077308 NadE* enzyme (FspTNadE*) open reading frame SEQ ID NO: 25 is the nucleotide sequence encoding the *Francisella* sp. FSC1006 NadE* enzyme (FspFNadE*) open reading frame SEQ ID NO: 26 is the nucleotide sequence encoding the *Francisella* guangzhouensis NadE* enzyme (FgNadE*) open reading frame SEQ ID NO: 27 is the nucleotide sequence encoding the *Francisella persica* ATCC VR-331 NadE* enzyme (FpeNadE*) open reading frame SEQ ID NO: 28 is the nucleotide sequence encoding the *Mannheimia succinoproducens* MBEL55E NadE* enzyme (MnNadE*) open reading frame optimized for expression in *E. coli.*

SEQ ID NO: 29 is the nucleotide sequence encoding the *Dichelobacter nodosus* VCS1703A NadE* enzyme (DnNadE*) open reading frame optimized for expression in *E. coli.*

SEQ ID NO: 30 is the nucleotide sequence encoding the *Actinobacillus succinogenes* NadE* enzyme (AsNadE*) open reading frame optimized for expression in *E. coli.*

SEQ ID NO: 31 is the nucleotide sequence encoding the *Francisella philomiragia* subsp. *philomiragia* ATCC 25017 NadE* enzyme (FphNadE*) open reading frame optimized for expression in *E. coli.*

SEQ ID NO: 32 is the nucleotide sequence encoding the *Francisella* cf. *novicida* 3523 NadE* enzyme (FnNadE*) open reading frame optimized for expression in *E. coli.*

SEQ ID NO: 33 is the nucleotide sequence encoding the *Francisella* sp. TX077308 NadE* enzyme (FspTNadE*) open reading frame optimized for expression in *E. coli.*

SEQ ID NO: 34 is the nucleotide sequence encoding the *Francisella* sp. FSC1006 NadE* enzyme (FspFNadE*) open reading frame optimized for expression in *E. coli.*

SEQ ID NO: 35 is the nucleotide sequence encoding the *Francisella guangzhouensis* NadE* enzyme (FgNadE*) open reading frame optimized for expression in *E. coli.*

SEQ ID NO: 36 is the nucleotide sequence encoding the *Francisella persica* ATCC VR-331 NadE* enzyme (FpeNadE*) open reading frame optimized for expression in *E. coli.*

SEQ ID NO: 37 is the nucleotide sequence encoding the *Francisella tularensis* NadE* enzyme (FtNadE*) open reading frame optimized for expression in *E. coli.*

SEQ ID NO: 38 is the nucleotide sequence encoding the *Francisella tularensis* NadE* enzyme (FtNadE*) open reading frame optimized for expression in *B. subtilis*

SEQ ID NO: 39 is the nucleotide sequence encoding the *Mannheimia succinoproducens* MBEL55E NadE* enzyme (MnNadE*) open reading frame optimized for expression in *B. subtilis.*

SEQ ID NO: 40 is the nucleotide sequence encoding the *Francisella* cf. *novicida* 3523 NadE* enzyme (FnNadE*) open reading frame optimized for expression in *B. subtilis.*

SEQ ID NO: 41 is the nucleotide sequence encoding the *Francisella* sp. TX077308 NadE* enzyme (FspTNadE*) open reading frame optimized for expression in *B. subtilis.*

SEQ ID NO: 42 is the nucleotide sequence encoding the *Francisella tularensis* NadE* enzyme (FtNadE*) open reading frame optimized for expression in *E. coli* and encoding the mutations Y27T, Q133G, and R236V.

SEQ ID NO: 43 is the nucleotide sequence encoding the *Mannheimia succinoproducens* MBEL55E NadE* enzyme (MnNadE*) open reading frame optimized for expression in *E. coli* and encoding the mutations Y22T, Q128G, and R231V.

SEQ ID NO: 44 is the nucleotide sequence encoding the *Francisella* cf. *novicida* 3523 NadE* enzyme (FnNadE*) open reading frame optimized for expression in *E. coli* and encoding the mutations Y27T, Q133G, and R236V.

SEQ ID NO: 45 is the nucleotide sequence encoding the *Francisella* sp. TX077308 NadE* enzyme (FspTNadE*) open reading frame optimized for expression in *E. coli* and encoding the mutations Y27T, Q133G, and R236V.

SEQ ID NO: 46 is the nucleotide sequence encoding the *E. coli* NadE enzyme (EcNadE) encoding a nicotinamide adenine dinucleotide amidating activity.

SEQ ID NO: 47 is the nucleotide sequence encoding the *Francisella* cf. *novicida* 3523 NadE* enzyme (FnNadE*) open reading frame optimized for expression in *C. glutamicum.*

SEQ ID NO: 48 is a nucleotide sequence encoding tetracycline resistance.

SEQ ID NO: 49 is a nucleotide sequence encoding neomycin resistance.

SEQ ID NO: 50 is a nucleotide sequence encoding spectinomycin resistance.

SEQ ID NO: 51 is the amino acid sequence encoding the *Escherichia coli* NadR enzyme (NMN synthetase, NR kinase, negative regulator of NAD+ biosynthesis).

SEQ ID NO: 52 is the amino acid sequence encoding the *Bacillus subtilis* NadR (a.k.a. YxrA) enzyme, which is a repressor protein.

SEQ ID NO: 53 is the amino acid sequence encoding the *Corynebacterium glutamicum* NadR (a.k.a. CgR_1153) enzyme, which is a repressor protein.

SEQ ID NO: 54 is the amino acid sequence encoding the *Acinetobacter baylyi* PnuC enzyme, which is a NR transporter protein.

SEQ ID NO: 55 is the amino acid sequence encoding the *Corynebacterium glutamicum* PnuC enzyme, which is a NR transporter protein.

SEQ ID NO: 56 is the amino acid sequence encoding the *Escherichia coli* PnuC enzyme, which is a NR transporter protein.

SEQ ID NO: 57 is the amino acid sequence encoding the *Escherichia coli* UshA enzyme, which is a nicotinamide mononucleotide hydrolase.

SEQ ID NO: 58 is the amino acid sequence encoding the *Bacillus subtilis* UshA (a.k.a. YfkN) enzyme, which is a nicotinamide mononucleotide hydrolase.

SEQ ID NO: 59 is the amino acid sequence encoding the *Corynebacterium glutamicum* UshA (a.k.a. Cg0397) enzyme, which is a nicotinamide mononucleotide hydrolase.

SEQ ID NO: 60 is the amino acid sequence encoding the *Escherichia coli* PncC enzyme, which is a nicotinamide mononucleotide amidohydrolase.

SEQ ID NO: 61 is the amino acid sequence encoding the *Bacillus subtilis* PncC (a.k.a. CinA) enzyme, which is a nicotinamide mononucleotide amidohydrolase.

SEQ ID NO: 62 is the amino acid sequence encoding the *Corynebacterium glutamicum* PncC (a.k.a. Cg2153) enzyme, which is a nicotinamide mononucleotide amidohydrolase.

SEQ ID NO: 63 is the amino acid sequence encoding the *Escherichia coli* NadD enzyme, which is a nicotinic acid mononucleotide adenyltransferase.

SEQ ID NO: 64 is the amino acid sequence encoding the *Bacillus subtilis* NadD enzyme, which is a nicotinic acid mononucleotide adenyltransferase.

SEQ ID NO: 65 is the amino acid sequence encoding the *Corynebacterium glutamicum* NadD (a.k.a. Cg2584) enzyme, which is a nicotinic acid mononucleotide adenyltransferase.

SEQ ID NO: 66 is the amino acid sequence encoding the *Acinetobacter* NudC enzyme, which is a NAD+ diphosphatase.

SEQ ID NO: 67 is the amino acid sequence encoding the *Escherichia coli* NudC enzyme, which is a NAD+ diphosphatase.

SEQ ID NO: 68 is the amino acid sequence encoding the *Corynebacterium glutamicum* NudC (a.k.a. Cg0888) enzyme, which is a NAD+ diphosphatase.

SEQ ID NO: 69 is the amino acid sequence encoding the *Burkholderiaceae* NudC enzyme, which is a NAD+ diphosphatase.

SEQ ID NO: 70 is the amino acid sequence encoding the *Haemophilus influenzae NudC enzyme, which is a NAD+ diphosphatase.*

SEQ ID NO: 71 is the amino acid sequence encoding the *B. subtilis* NupG protein, which is a NR transporter protein.

SEQ ID NO: 72 is the amino acid sequence encoding the *B. subtilis* DeoD enzyme, which is a nucleoside phosphorylase.

SEQ ID NO: 73 is the amino acid sequence encoding the *B. subtilis* Pdp enzyme, which is a nucleoside phosphorylase.

SEQ ID NO: 74 is the amino acid sequence encoding the *B. subtilis* PupG enzyme, which is a nucleoside phosphorylase.

SEQ ID NO: 75 is the amino acid sequence encoding the *E. coli* DeoD enzyme, which is a nucleoside phosphorylase.

SEQ ID NO: 76 is the amino acid sequence encoding the *C. glutamicum* G18NG enzyme, which is a nucleoside phosphorylase.

SEQ ID NO:77 is the amino acid sequence encoding the *Escherichia coli* NadA enzyme, which is a quinolate synthase SEQ ID NO:78 is the amino acid sequence encoding the *Bacillus subtilis* NadA enzyme, which is a quinolate synthase SEQ ID NO:79 is the amino acid sequence encoding the *Corynebacterium glutamicum* NadA enzyme, which is a quinolate synthase SEQ ID NO:80 is the amino acid sequence encoding the *Escherichia coli* NadB enzyme, which is a L-aspartate oxidase SEQ ID NO:81 is the amino acid sequence encoding the *Bacillus subtilis* NadB enzyme, which is a L-aspartate oxidase SEQ ID NO:82 is the amino acid sequence encoding the *Escherichia coli* NadC enzyme, which is a quinolate phosphoribosyl transferase SEQ ID NO:83 is the amino acid sequence encoding the *Bacillus subtilis* NadC enzyme, which is a quinolate phosphoribosyl transferase SEQ ID NO:84 is the amino acid sequence encoding the *Corynebacterium glutamicum* NadC enzyme, which is a quinolate phosphoribosyl transferase SEQ ID NO:85: is Primer 10444

SEQ ID NO:86: is Primer 10447

SEQ ID NO:87: is Primer 11222

SEQ ID NO:88: is Primer 11223

SEQ ID NO:89: is Primer 11226

SEQ ID NO:90: is Primer 11227

SEQ ID NO:91: is Primer 11230

SEQ ID NO:92: is Primer 11231

SEQ ID NO:93: is Primer 11232

SEQ ID NO:94: is Primer 11233

SEQ ID NO:95: is Primer 11234

SEQ ID NO:96: is Primer 11235

SEQ ID NO:97: is Primer 11341

SEQ ID NO:98: is Primer 11342

SEQ ID NO:99: is Primer 11351

SEQ ID NO:100: is Primer 11352

SEQ ID NO:101: is Primer 11353

SEQ ID NO:102: is Primer 11354

SEQ ID NO:103: is Primer 11159

SEQ ID NO:104: is Primer 11160

BRIEF DESCRIPTION OF THE DRAWINGS

Embodiments of the invention will now be shown, by way of example only, with reference to FIGS. 1-4 in which:

FIG. 5 shows ClustalW alignment of NadE* sequences with highlighted Y-Q-R motif.

DETAILED DESCRIPTION OF THE INVENTION

Figure 1:
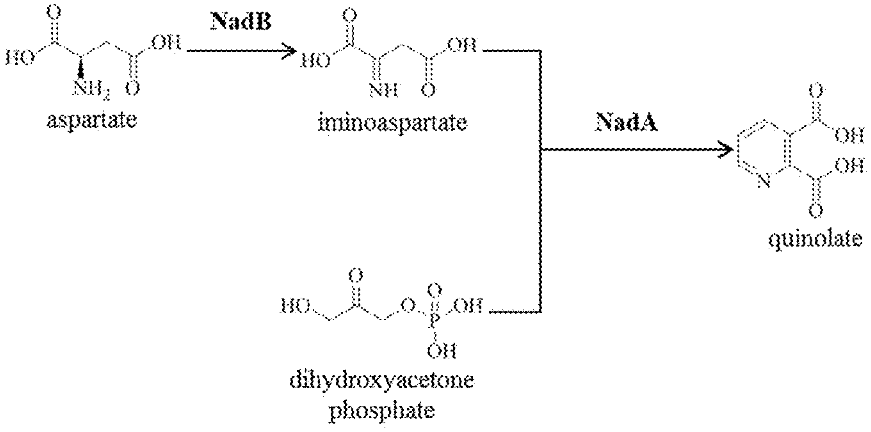
FIG. 1 shows the biochemical pathway for synthesizing quinolate from aspartate and dihydroxyacetone phosphate in the presence of NadA and NadB enzymes.

Unless otherwise defined herein, scientific and technical terms used herein will have the meanings that are commonly understood by one of ordinary skill in the art.

The term "nicotinic acid amidating protein" indicates an enzyme capable of catalyzing the conversion of nicotinic acid mononucleotide (NaMN) to nicotinamide mononucleotide (NMN). The enzyme is referred to herein as "NadE*". Examples of nicotinic acid amidating protein are the polypeptides having amino acid sequences SEQ ID NO: 1 and 3 to 18. SEQ ID NO: 1 is derived from *Francisella tularensis*, and is known as FtNadE*. The FtNadE* protein sequence is provided under GENBANK accession no. YP_170217. SEQ ID NO: 3 is derived from *Francisella* sp. FSC1006 and is known as FspFNadE*; the protein accession number is available under accession no: WP_040008427.1. SEQ ID NO: 4 is derived from *Francisella guangzhouensis* strain 08HL01032 and is known as FgNadE*; the protein accession number is available under accession no: WP_039124332.1. SEQ ID NO: 5 is derived from *Francisella* sp. TX077308 and is known as FspTNadE*; the protein accession number is available under accession no: WP_013922810.1. SEQ ID NO: 6 is derived from *Francisella philomiragia* subsp. *philomiragia* ATCC 25017 and is known as FphNadE*; the protein accession number is available under accession no: WP_004287429.1. SEQ ID NO: 7 is derived from *Francisella philomiragia* strain O #319-036 [FSC 153] and is known as NadE*; the protein accession number is available under accession no: WP_042517896.1. SEQ ID NO: 8 is derived from *Francisella noatunensis* subsp. *orientalis* str. Toba 04 and is known as NadE*; the protein accession number is available under accession no: WP_014714556.1. SEQ ID NO: 9 is derived from *Francisella philomiragia* strain GA01-2794 and is known as NadE*; the protein accession number is available under accession no: WP_044526539.1. SEQ ID NO: 10 is derived from *Francisella persica* ATCC VR-331 and is known as FpeNadE*; the protein accession number is available under accession no: WP_064461307.1. SEQ ID NO: 11 is derived from *Francisella* cf. *novicida* 3523 and is known as FnNadE*; the protein accession number is available under accession no: WP_014548640.1. SEQ ID NO: 12 is derived from *Francisella tularensis* subsp. *novicida* D9876 and is known as NadE*; the protein accession number is available under accession no: WP_003037081.1. SEQ ID NO: 13 is derived from *Francisella tularensis* subsp. *novicida* F6168 and is known as NadE*; the protein accession number is available under accession no: WP_003034444.1. SEQ ID NO: 14 is derived from *Francisella tularensis* subsp. *tularensis* strain NIH B-38 and is known as NadE*; the protein accession number is available under accession no: WP_003025712.1. SEQ ID NO: 15 is derived from *Francisella tularensis* subsp. holarctica F92 and is known as NadE*; the protein accession number is available under accession no: WP_010032811.1. SEQ ID NO: 16 is derived from *Dichelobacter nodosus* VCS1703A and is known as DnNadE*; the protein accession number is available under accession no: WP_011927945.1. SEQ ID NO: 17 is derived from *Mannheimia succiniciproducens* MBEL55E and is known as MsNadE*; the protein accession number is available under accession no: WP_011201048.1. SEQ ID NO: 18 is derived from *Actinobacillus succinogenes* 130Z and is known as AsNadE*; the protein accession number is available under accession no: WP_012072393.1.

The term "nicotinamide adenine dinucleotide hydrolyzing protein" or "NAD+ diphosphatase" indicates an enzyme capable of catalyzing the conversion of nicotinamide adenine dinucleotide (NAD+) to nicotinamide mononucleotide (NMN) and adenine. The enzyme is commonly known as NudC. The nicotinamide adenine dinucleotide hydrolyzing protein used in this invention can be from various organisms, such as *E. coli, C. glutamicum, A. baylyi*, etc. Examples of nicotinamide adenine dinucleotide hydrolyzing proteins include polypeptides having amino acid sequence SEQ ID NOs: 66 to 70. Exemplary genes encoding the NAD+ diphosphatase activity are provided under accession nos. WP_004921449 (*A. baylyi*), CAF19483 (*C. glutamicum*), YP_026280 (*E. coli*), and WP_010813670 (*R. eutropha*).

The term "negative regulator of NAD+ biosynthesis" indicates an enzyme capable of repressing NAD+ biosynthesis activity by repressing transcription of quinolate synthase (NadA), FAD dependent L-aspartate oxidase (NadB), quinolate phosphoribosyltransferase (NadC), or any combination thereof. Exemplary genes encoding negative regulators of NAD+ biosynthesis are provided under accession nos. WP_004398582.1 (*B. subtilis*), WP_000093814.1 (*E. coli*) and WP_011014097.1 (*C. glutamicum*). The term "quinolate synthase" indicates an enzyme capable of converting iminosuccinic acid and dihydroxyacetone phosphate to quinolate and phosphate. The quinolate synthase used in this invention can be from various organisms, such as *E. coli, B. subtilis, C. glutamicum*, etc. Examples of quinolate synthase proteins include polypeptides having amino acid sequence SEQ ID NO: 77, 78, or 79. Genes encoding the quinolate synthesis activity are provided under, for example, accession nos. ACX40525 (*E. coli*), NP 390663 (*B. subtilis*), and CAF19774 (*C. glutamicum*). The quinolate synthase as defined includes functional variants of the above mentioned quinolate synthases.

The term "L-aspartate oxidase" indicates an enzyme capable of converting aspartic acid to iminosuccinic acid in an FAD dependent reaction. The L-aspartate oxidase used in this invention can be from various organisms, such as *E. coli, B. subtilis, C. glutamicum*, etc. Examples of nucleoside hydrolase proteins include polypeptides having amino acid sequence SEQ ID NO: 80 or 81. Genes encoding the L-aspartate oxidase activity are provided under, for example, accession nos. ACX38768 (*E. coli*) and NP_390665 (*B. subtilis*). The L-aspartate oxidase as defined includes functional variants of the above mentioned L-aspartate oxidases.

The term "quinolate phosphoribosyl transferase" indicates an enzyme capable of converting quinolate and phosphoribosylpyrophosphate to nicotinamide mononucleotide and carbon dioxide. The quinolate phosphoribosyl transferase used in this invention can be from various organisms, such as *E. coli, B. subtilis, C. glutamicum*, etc. Examples of nucleoside hydrolase proteins include polypeptides having amino acid sequence SEQ ID NOs: 82, 83, or 84. Genes encoding the quinolate phosphoribosyl transferase activity are provided under, for example, accession nos. ACX41108 (*E. coli*), NP_390664 (*B. subtilis*), and CAF19773 (*C. glutamicum*). The quinolate phosphoribosyl transferase as defined includes functional variants of the above mentioned quinolate phosphoribosyl transferases.

The term "nicotinamide riboside transporter protein" indicates an enzyme capable of catalyzing the transport of nicotinamide riboside for importing nicotinamide riboside from the periplasm to the cytoplasm. The enzyme is commonly known as PnuC. The nicotinamide riboside transporter protein described in this invention is a native polypeptide of the host organism such as *E. coli, B. subtilis, C. glutamicum*, etc. Examples of nicotinamide riboside transporter proteins include polypeptides having amino acid sequences SEQ ID NO: 54, 55, 56, or 71. Genes encoding the NR transport activity are provided under, for example, accession nos. CAG67923 (*A. baylyi*), NP_599316 (*C. glutamicum*), NP_415272 (*E. coli*), and WP_003227216.1 (*B. subtilis*).

The term "nicotinamide mononucleotide hydrolase" indicates an enzyme capable of catalyzing the hydrolysis of nicotinamide mononucleotide to nicotinamide riboside. The enzyme is commonly known as UshA. The nucleoside hydrolase used in this invention can be from various organisms, such as *E. coli, B. subtilis*, C, *glutamicum* etc. Examples of nucleoside hydrolase proteins include polypeptides having amino acid sequence SEQ ID NOs: 57, 58, or 59. Genes encoding the nucleoside hydrolase activity are provided under, for example, accession nos. NP_415013 (*E. coli*), NP_388665 (*B. subtilis*), and CAF18899 (*C. glutamicum*).

The term "nicotinamide mononucleotide amidohydrolase" indicates an enzyme capable of catalyzing the conversion of nicotinamide mononucleotide to nicotinic acid mononucleotide. The enzyme is commonly known as PncC. The nicotinamide mononucleotide amidohydrolase described in this invention is a native polypeptide of the host organism such as *E. coli, B. subtilis, C. glutamicum*, etc. Examples of nicotinamide mononucleotide amidohydrolase proteins include polypeptides having amino acid sequences SEQ ID NOs: 60, 61, or 62. Genes encoding the nicotinamide mononucleotide amidohydrolase activity are provided under, for example, accession nos. NP_417180 (*E. coli*), AAB00568 (*B. subtilis*), and CAF20304 (*C. glutamicum*).

The term "nicotinic acid mononucleotide adenyltransferase" indicates an enzyme capable of catalyzing the conversion of nicotinic acid mononucleotide to nicotinic acid adenine dinucleotide. The enzyme is commonly known as NadD. The nicotinic acid mononucleotide adenyltransferase protein described in this invention is a native polypeptide of the host organism such as *E. coli, B. subtilis, C. glutamicum*, etc. Examples of nicotinic acid mononucleotide adenyltransferase proteins include polypeptides having amino acid sequences SEQ ID NOs: 63, 64, or 65. Genes encoding the nicotinic acid mononucleotide adenyltransferase activity are provided under, for example, accession nos. NP_415172 (*E. coli*), NP_390442 (*B. subtilis*), and CAF21017 (*C. glutamicum*).

The term "purine nucleoside phosphorylase" indicates an enzyme capable of catalyzing the conversion of nicotinamide riboside and phosphate to nicotinamide and ribose-1-phosphate. Common names for the enzyme are DeoD, PupG and Pdp. The purine nucleoside phosphorylase described in this in this invention is a native polypeptide of the host organism such as *E. coli, B. subtilis, C. glutamicum*, etc. Examples of purine nucleoside phosphorylase proteins include polypeptides having amino acid sequences SEQ ID NOs: 72 to 75. Genes encoding the purine nucleoside phosphorylase activity are provided under, for example, accession nos. WP_003231176.1 (*B. subtilis*), WP_003243952.1 (*B. subtilis*), WP_0032300447.1 (*B. subtilis*), WP_000224877.1 (*E. coli*), and BAC00196.1 (*C. glutamicum*).

Sequence Identity: The relatedness between two amino acid sequences or between two nucleotide sequences is described by the parameter "sequence identity".

For purposes of the present disclosure, the degree of sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues}\times 100)/(\text{Length of Alignment}-\text{Total Number of Gaps in Alignment})$$

Nucleic acid construct: The term "nucleic acid construct" means a nucleic acid molecule, either single or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present disclosure.

Control sequences: The term "control sequences" means all components necessary for the expression of a polynucleotide encoding a polypeptide of the present disclosure. Each control sequence may be native or foreign to the polynucleotide encoding the polypeptide or native or foreign to each other. Such control sequences include, but are not limited to, a leader, polyadenylation sequence, peptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Operably linked: The term "operably linked" means a configuration in which a control sequence is placed at an appropriate position relative to the coding sequence of a polynucleotide such that the control sequence directs the expression of the coding sequence.

Expression: The term "expression" includes any step involved in the production of the polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to additional nucleotides that provide for its expression.

Host cell: The term "host cell" means any bacterial cell type that is susceptible to transformation, transfection, transduction, and the like with a nucleic acid construct or expression vector comprising a polynucleotide encoding any one of the polypeptide sequences of the present disclosure. The term "host cell" encompasses any progeny of a parent cell that is not identical to the parent cell due to mutations that occur during replication.

The present invention features bacterial strains with genetically engineered features for the production of nicotinamide riboside.

Figure 2:
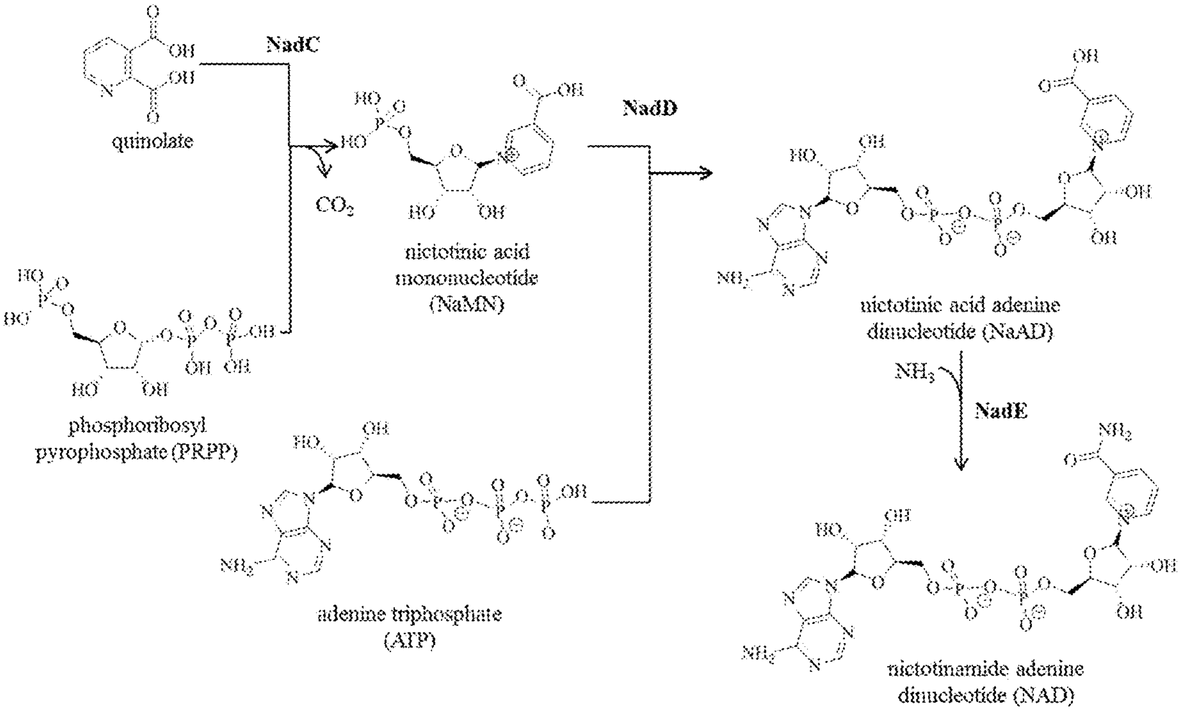
FIG. 2 shows biochemical pathways and enzymes for synthesizing nicotinamide adenine dinucleotide.

The nadE gene product from *E. coli, B. subtilis*, and most characterized bacterial species, as well as all characterized eukaryotic species, utilizes nicotinic acid adenine dinucleotide as substrate for an amidation reaction to produce NAD+. By this native pathway, nicotinamide riboside (NR) is obtained by breakdown of nicotinamide adenine dinucleotide (NAD+), as in previously described work (U.S. Pat. No. 8,114,626 B2). See FIG. 2.

The organism *Francisella tularensis* synthesizes NAD+ via an alternative pathway where NMN is generated from NaMN by the action of *F. tularensis* NMN synthetase (FtNadE*).

Figure 3:
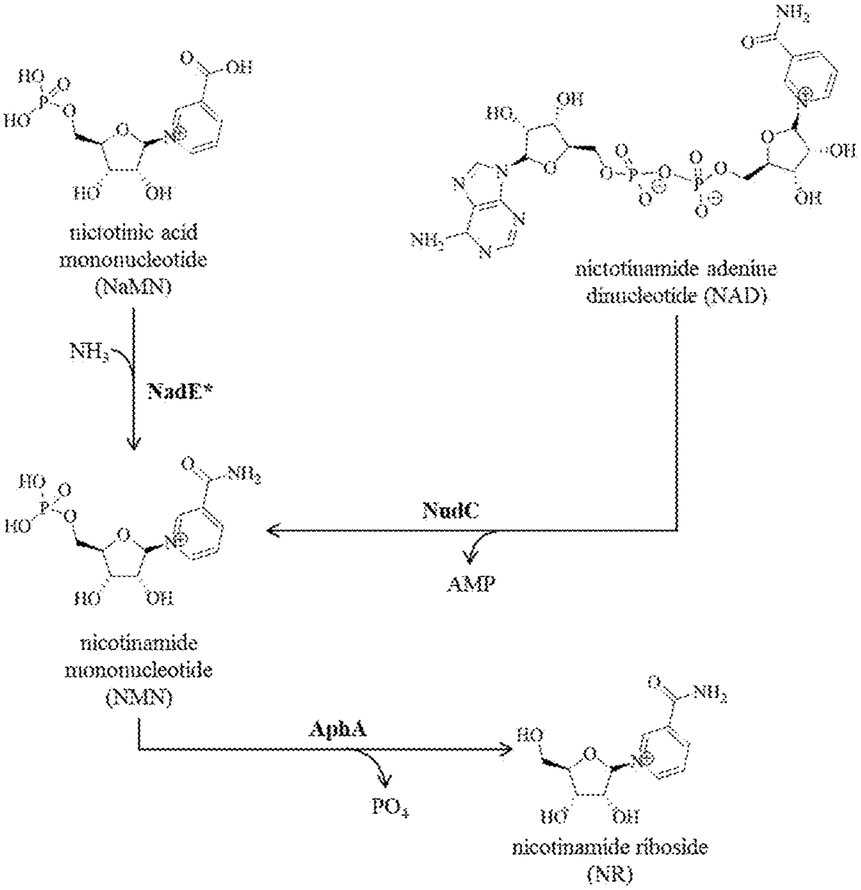
FIG. 3 shows biochemical pathways useful for the production of nicotinamide riboside from NAD+ or intermediates of NAD+ biosynthesis.

Unexpectedly, the inventor of the present invention created an alternative pathway to NR in bacteria which consists of the amidation of nicotinic acid mononucleotide to NMN, followed by dephosphorylation to NR. See FIG. 3. For example, the inventor of the present invention has discovered that expression of the FtNadE* gene or its functional homologs in *E. coli* will result in production of excess NMN. Excess NMN can be exported and converted to NR by native periplasmic acid phosphatase.

The inventor of the present invention has further discovered that FtNadE* is not the only protein that can be used in the above alternative pathway to produce NR. The inventor of the present invention has identified a group of NadE* proteins from diverse strains of gamma-proteobacteria that perform the same function. For example, expression of the NadE* gene or its functional homologs encoding nicotinic acid amidating proteins with SEQ ID Nos: 3-18 will also result in production of NR.

Accordingly, in a first embodiment of the invention, it is desirable to introduce one or more nicotinic acid amidating genes into a host cell. Such genes encode nicotinic acid amidating proteins which catalyzes the conversion of NaMN to NMN. In one embodiment, the nicotinic acid amidating protein is NMN synthetase (NadE*). In a specific embodiment, the nicotinic acid amidating protein is *F. tularensis* NMN synthetase (FtNadE*). The nicotinic acid amidating protein according to embodiments herein may include, for example and without limitation, a polypeptide comprising an amino acid sequence having at least 50%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO:1 or 3 to 18, wherein the above polypeptide has the nicotinic acid amidating activity or the NadE* activity.

Inventor of the present application has identified the conserved polypeptides among SEQ ID NO: 1 and 3 to 18. The result of the sequence alignment is shown in FIG. 5. In addition, the following three amino acids are considered very important in maintaining NadE* protein activity: tyrosine at position 27, glutamine at position 133, and arginine at position 236. The above positions are numbered based on SEQ ID NO: 1. See the ClustalW alignment of SEQ ID Nos: 1 and 3 to 18 in FIG. 5.

Thus, in some embodiments, the NadE* protein may further contain one or more of the following conserved amino acids when compared with the reference amino acid sequence of SEQ ID NO:1: a) tyrosine at position 27, b) glutamine at position 133, and c) arginine at position 236, based on the ClustalW method of alignment when compared to SEQ ID NOs: 1 and 3 to 18 using the default parameters of GAP PENALTY=10, GAP LENGTH PENALTY=0.1, and Gonnet 250 series of protein weight matrix. SEQ ID NO: 1 has tyrosine at position 27, glutamine at position 133, and arginine at position 236.

In *E. coli* and other bacterial species, the nudC gene product catalyzes the hydrolysis of NADH to NMN and adenosine monophosphate (AMP). The nudC gene is expressed at very low levels under most growth conditions. Unexpectedly, the inventor of the present invention created an alternative pathway to drive production of NMN from NADH by adding a heterologous nudC gene in a host cell either with or without native nudC gene or by placing the native nudC gene under the control of a strong constitutive or inducible promoter. See FIG. 3. Expression of nudC under production conditions results in production of excess NMN. Excess NMN can be exported and converted to NR by native periplasmic acid phosphatase.

Accordingly, in a second embodiment of the invention, it is desirable to increase the expression level of the nudC gene and thus to cause the host cell to produce excess NMN. In one embodiment, the invention is directed to a bacterial strain having an increased activity of NAD+ diphosphatase. The NAD+ diphosphatase according to embodiments herein may include, for example and without limitation, a polypeptide comprising an amino acid sequence having at least 50%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identity to any one of SEQ ID NOs: 66 to 70 wherein the above polypeptide has the activity of NAD+ diphosphatase for converting NAD+ to NMN.

It is desirable to modify the host organism for NR production such that a higher concentration of NaMN is available intracellularly. Accordingly, in a further embodiment of the invention, it is desirable to introduce one or more genetic modifications resulting in increased rates of production of nicotinic acid mononucleotide within a host cell. The modification may include deletion or reduction in expression of a gene that represses transcription of all or some of the genes of the de novo NAD+ biosynthetic pathway, nadA, nadB, and/or nadC. The modification may also or alternatively include increasing the expression of the L-aspartate oxidase gene, the quinolate synthase gene, quinolate phosphoribosylpyrophosphate gene, or combinations thereof, encoded, for example, by nadB (*E. coli, B. subtilis*), nadA (*E. coli, B. subtilis, C. glutamicum*), or nadC (*E. coli, B. subtilis, C. glutamicum*). The modification may also or alternatively include modifications to the nadB gene which render the gene resistant to inhibition by the downstream metabolite NAD+.

Figure 4:
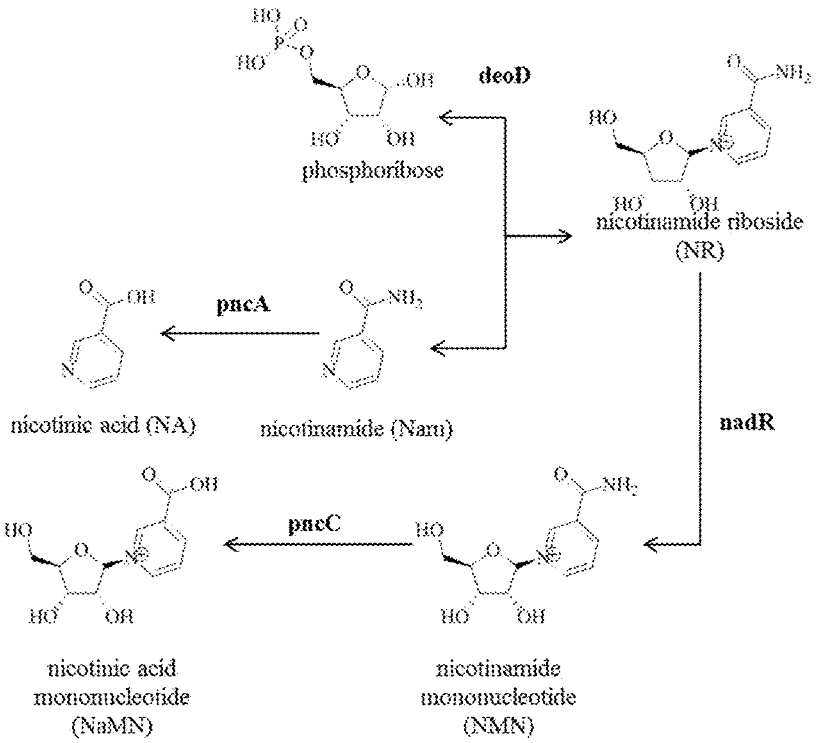
FIG. 4 shows biochemical pathways with undesirable activities for nicotinamide riboside production.

The present invention further embraces a genetically engineered bacterial strain deficient in nicotinamide riboside import and salvage pathways. See FIG. 4. Disruption of the NAD+ salvage pathway in bacteria is expected to result in accumulation of extracellular NR, because such a strain would fail to import nicotinamide riboside into the cytoplasm and would also fail to phosphorylate nicotinamide riboside (NR) into nicotinamide mononucleotide (NMN), or to further degrade NMN into nicotinic acid mononucleotide (NaMN). Three enzyme activities are of particular importance for engineering bacterial NR production. The pncC gene product in *E. coli* and the cinA gene product in *B. subtilis* are salvage enzymes in bacteria which carries out the deamidation of NMN to NaMN, the opposite reaction to that catalyzed by NadE*. Deletion of this gene prevents conversion of NMN to NaMN and increases the intracellular concentration of NMN. The degradation of NR to Nam and ribose phosphate by the nucleoside phosphorylase activity removes product and deletion or decreased expression of the gene encoding this activity, for example deoD in *E. coli* or pdp in *B. subtilis*, will increase rates of product formation. In *E. coli*, and many other bacteria, the pnuC gene product imports NR and deletion will increase extracellular NR; in *B. subtilis* NR import is accomplished by the nupG gene product and deletion will increase extracellular NR.

Accordingly, in a third embodiment of the invention, it is desirable to reduce or block the nicotinamide riboside import and salvage pathways and thus cause the host cell to preserve the nicotinamide riboside that has been produced. In certain embodiments, bacterial strains of this invention possess one or more of the following features: i) a blocked or reduced activity of a nicotinamide uptake transporter, ii) a blocked or reduced protein which functions as a nicotinic acid riboside phosphorylase, and iii) a blocked or reduced activity of nicotinamide mononucleotide amidohydrolase, iv) a blocked or reduced protein which functions as a negative regulator of NAD+ biosynthesis proteins such as L-aspartate oxidase, a quinolate synthase, and quinolate phoshoribosyltransferase, v) a blocked or reduced protein which functions as a purine nucleoside phosphorylase; and vi) a blocked or reduced protein which functions as a nicotinic acid mononucleotide adenyltransferase.

The negative regulator of NAD+ biosynthesis according to embodiments herein may include, for example and without limitation, a polypeptide comprising an amino acid sequence of any one of SEQ ID NOs: 51, 52, or 53, or a variant of said polypeptide, wherein the above polypeptide has the activity of repressing genes required for NAD+ biosynthesis.

In some embodiments, the quinolate synthase is a polypeptide comprising an amino acid sequence of either SEQ ID NO: 77, 78, or 79, or a variant of said polypeptide, wherein said polypeptide has an activity of forming quinolate from iminosuccinic acid and dihydroxyacetone phosphate.

In some embodiments, the L-aspartate oxidase is a polypeptide comprising an amino acid sequence of either SEQ ID NO: 80 or 81, or a variant of said polypeptide, wherein said polypeptide has an activity of forming iminosuccinic acid from aspartic acid.

In some embodiments, the quinolate phosphoribosyltransferase is a polypeptide comprising an amino acid sequence of either SEQ ID NO: 82, 83, or 84, or a variant of said polypeptide, wherein said polypeptide has an activity of forming nicotinic acid mononucleotide from quinolate and phosphoribosylpyrophosphate.

The nicotinamide uptake transporter (PnuC or NupG) according to embodiments herein may include, for example and without limitation, a polypeptide comprising an amino acid sequence of any one of SEQ ID NOs: 54, 55, 56, or 71, or a variant of said polypeptide, wherein the above polypeptide has nicotinamide ribose importing activity.

The nicotinamide mononucleotide amidohydrolase (PncC) according to embodiments herein may include, for example and without limitation, a polypeptide comprising an amino acid sequence of any one of SEQ ID NOs: 15, 16, or 17, or a variant of said polypeptide, wherein the above polypeptide has the activity of nicotinamide mononucleotide amidohydrolase.

The nicotinic acid mononucleotide adenyltransferase (NadD) according to embodiments herein may include, for example and without limitation, a polypeptide comprising an amino acid sequence of either SEQ ID NO: 18 or SEQ ID NO: 19, or a variant of said polypeptide, wherein the above polypeptide has the activity of nicotinic acid mononucleotide adenyltransferase for converting nicotinic acid mononucleotide to nicotinic acid adenine dinucleotide.

The purine nucleoside phosphorylase (DeoD, PupG, Pdp) according to embodiments herein may include, for example and without limitation, a polypeptide comprising an amino acid sequence of any one of SEQ ID NOs 72 to 76, or a variant of said polypeptide, wherein the above polypeptide has the activity of purine nucleoside phosphorylase for converting nicotinamide riboside and phosphate to nicotinamide and ribose-1-phosphate.

In a fourth embodiment of the invention, it is desirable to increase the expression level of the ushA gene and thus to cause the host cell to produce excess extracellular NR from NMN. In one embodiment, the invention is directed to a bacterial strain having an increased activity of the nucleoside hydrolase. The nicotinamide mononucleotide hydrolase (UshA) according to embodiments herein may include, for example and without limitation, a polypeptide comprising any one of SEQ ID NOs: 57, 58, or 59, or a variant of said polypeptide, wherein the above polypeptide has the activity of nucleoside hydrolase for converting nicotinamide mononucleotide to nicotinamide riboside.

It is also desirable to increase the expression level of NAD+ biosynthesis proteins, such as L-aspartate oxidase, a quinolate synthase, and quinolate phoshoribosyltransferase. In one embodiment, the invention is directed to a bacterial strain having an increased activity of one or more of the following proteins: L-aspartate oxidase, a quinolate synthase, and quinolate phoshoribosyltransferase.

In some embodiments, the quinolate synthase is a polypeptide comprising an amino acid sequence of either SEQ ID NO: 77, 78, or 79, or a variant of said polypeptide, wherein said polypeptide has an activity of forming quinolate from iminosuccinic acid and dihydroxyacetone phosphate.

In some embodiments, the L-aspartate oxidase is a polypeptide comprising an amino acid sequence of either SEQ ID NO: 80 or 81, or a variant of said polypeptide, wherein said polypeptide has an activity of forming iminosuccinic acid from aspartic acid.

In some embodiments, the quinolate phosphoribosyltransferase is a polypeptide comprising an amino acid sequence of either SEQ ID NO: 82, 83, or 84, or a variant of said polypeptide, wherein said polypeptide has an activity of forming nicotinic acid mononucleotide from quinolate and phosphoribosylpyrophosphate.

In other embodiments, the bacterial strains described in the above first or second embodiment further comprise one or more modifications described in the above third embodiment or fourth embodiment.

For example, in one embodiment, the present invention is directed to a genetically modified bacterium capable of producing nicotinamide riboside, wherein the bacterium comprises the following modifications: i) an added heterologous nicotinic acid amidating protein NadE* and ii) one or more additional modifications selected from the group consisting of: a) an altered negative regulator of NAD+ biosynthesis with a blocked or reduced activity; b) an altered nicotinamide riboside uptake transporter with a blocked or reduced activity; c) an altered nicotinic acid mononucleotide adenyltransferase with a blocked or reduced activity; d) an altered nicotinamide mononucleotide amidohydrolase with a blocked or reduced activity, e) an altered a purine nucleoside phosphorylase with blocked or reduced activity; f) an altered nicotinamide mononucleotide hydrolase with an added or increased activity; and g) added or increased transcription of a gene which encodes L-aspartate oxidase, quinolate synthase, quinolate phoshoribosyltransferase, or combinations thereof; wherein the bacterium with said at least one modification produces an increased amount of NR than the bacterium without any of said modifications.

In another embodiment, the present invention is directed to a genetically modified bacterium capable of producing nicotinamide riboside, wherein the bacterium comprises the following modifications: i) an altered nicotinamide adenine dinucleotide (NAD+) hydrolyzing protein NudC with an added or increased activity; and ii) one or more additional modifications selected from the group consisting of: a) an altered negative regulator of NAD+ biosynthesis with a blocked or reduced activity; b) an altered nicotinamide riboside uptake transporter with a blocked or reduced activity; c) an altered nicotinic acid mononucleotide adenyltransferase with a blocked or reduced activity; d) an altered nicotinamide mononucleotide amidohydrolase with a blocked or reduced activity, e) an altered a purine nucleoside phosphorylase with blocked or reduced activity; f) an altered nicotinamide mononucleoside hydrolase with an added or increased activity; and g) added or increased transcription of a gene which encodes L-aspartate oxidase, quinolate synthase, quinolate phoshoribosyltransferase, or combinations thereof; wherein the bacterium with said at least one modification produces an increased amount of NR than the bacterium without any of said modifications.

In one embodiment, the nicotinic acid amidating protein NadE* is exogenous to the host bacterium, i.e., not present in the cell prior to modification, having been introduced using recombination methods such as are described herein.

In another embodiment, the other proteins described above are endogenous to the host bacterium, i.e., present in the cell prior to modification, although alternations are made to increase or decrease the expression levels of the proteins. Examples of endogenous proteins for which expression levels are altered in the present invention include, but are not limited to, NAD+ diphosphatase, negative regulator of NAD+ biosynthesis, nicotinamide riboside uptake transporter, nicotinamide mononucleoside hydrolase, nicotinic acid mononucleotide adenyltransferase, and nicotinamide mononucleotide amidohydrolase.

The host bacterial cell may be genetically modified by any manner known to be suitable for this purpose by the person skilled in the art. This includes the introduction of the genes of interest, such as the gene encoding the nicotinic acid amidating protein NadE*, into a plasmid or cosmid or other expression vector which are capable of reproducing within the host cell. Alternatively, the plasmid or cosmid DNA or part of the plasmid or cosmid DNA or a linear DNA sequence may integrate into the host genome, for example by homologous recombination or random integration. To carry out genetic modification, DNA can be introduced or transformed into cells by natural uptake or by well-known processes such as electroporation. Genetic modification can involve expression of a gene under control of an introduced promoter. The introduced DNA may encode a protein which could act as an enzyme or could regulate the expression of further genes.

Genetic modification of a microorganism can be accomplished using classical strain development and/or molecular genetic techniques. Such techniques known in the art and are generally disclosed for microorganisms, for example, in Sambrook et al., 1989, *Molecular Cloning: A Laboratory Manual*, Cold Spring Harbor Labs Press. The reference Sambrook et al., ibid., is incorporated by reference herein in its entirety.

A suitable polynucleotide may be introduced into the cell by random integration, homologous recombination and/or may form part of an expression vector comprising a combination of genes. Such an expression vector forms another aspect of the invention.

Suitable vectors for construction of such an expression vector are well known in the art and may be arranged to comprise the polynucleotide operably linked to one or more expression control sequences, so as to be useful to express the required enzymes in a host cell, for example a bacterium as described above. For example, promoters including, but not limited to, T7 promoter, pLac promoter, nudC promoter, ushA promoter, pVeg promoter can be used in conjunction with endogenous genes and/or heterologous genes for modification of expression patterns of the targeted gene. Similarly, exemplary terminator sequences include, but are not limited to, the use of XPR1, XPR2, CPC1 terminator sequences.

Figure 7:
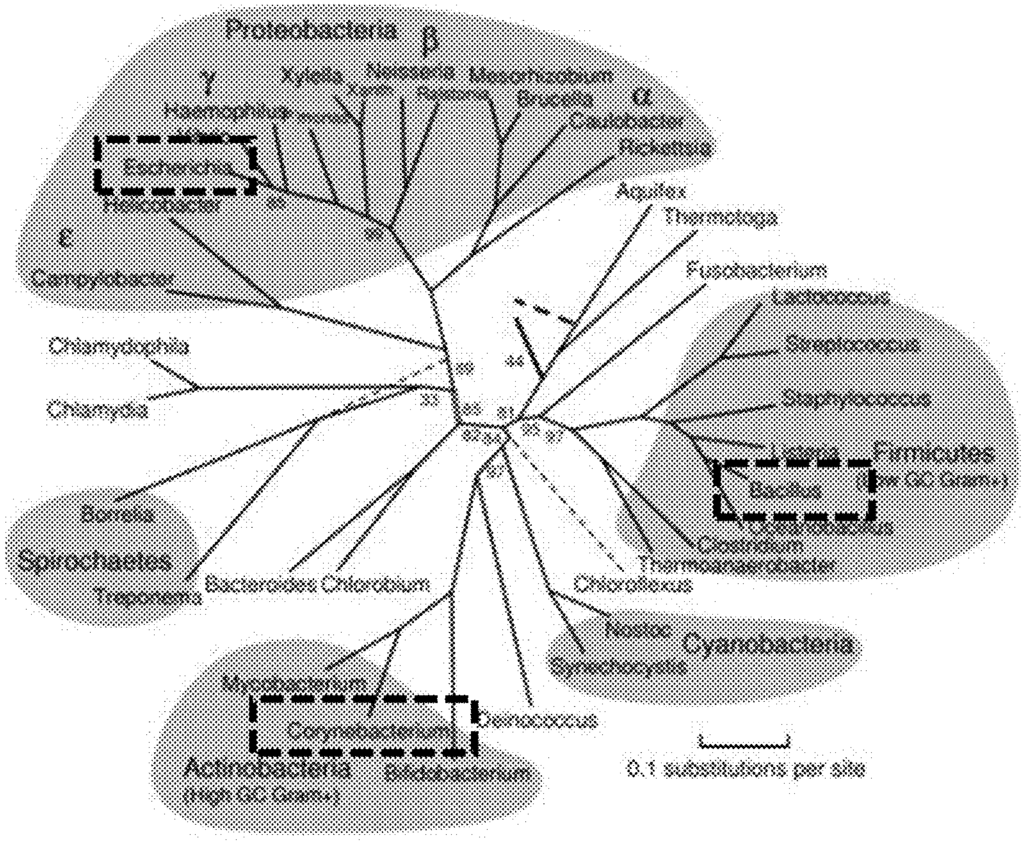
FIG. 7 shows rooted phylogenetic tree of Bacteria (Bern M., and Goldberg, D., BMC Evol. Bio. 2005) showing evolutionary distance between strains used in this study.

In some embodiments, the recombinant or genetically modified bacterial cell, as mentioned throughout this specification, may be any gram-positive bacteria or gram-negative bacteria including but not limited to the genera *Bacillus, Corynebacterium, Escherichia, Acinetobacter, Lactobacillus, Mycobacterium, Pseudomonas*, and *Ralstonia*. In certain embodiments, exemplary species of bacteria include, but are not limited to, *Bacillus subtilis, Corynebacterium glutamicum, Escherichia coli, Acinetobacter baylyi*, and *Ralstonia eutropha*. These embodiments are not limited to particular species but rather encompass all major phyla of bacteria (FIG. 7).

The genetically modified bacteria of the present disclosure also encompass bacteria comprising variants of the polypeptides as defined herein. As used herein, a "variant" means a polypeptide in which the amino acid sequence differs from the base sequence from which it is derived in that a substitution, insertion, and/or deletion of one or more (several) amino acid residues at one or more (several) positions are made. A substitution means a replacement of an amino acid occupying a position with a different amino acid; a deletion means removal of an amino acid occupying a position; and an insertion means adding 1-3 amino acids adjacent to an amino acid occupying a position.

The variants are functional variants in that the variant sequence has similar or identical functional enzyme activity characteristics to the enzyme having the native amino acid sequence specified herein.

For example, a functional variant of SEQ ID NOs: 1 and 3 to 18 has similar or identical nicotinic acid amidating protein FtNadE* activity characteristics as SEQ ID NOs: 1 and 3 to 18, respectively. An example may be that the rate of conversion by a functional variant of SEQ ID NOs: 1 and 3 to 18, of nicotinic acid mononucleotide to nicotinamide mononucleotide, may be the same or similar, although said functional variant may also provide other benefits. For example, at least about 80%, 90%, 95%, 96%, 97%, 98%, 99% or 100% the rate will be achieved when using the enzyme that is a functional variant of SEQ ID NOs: 1 and 3 to 18, respectively.

A functional variant or fragment of any of the above SEQ ID NO amino acid sequences, therefore, is any amino acid sequence which remains within the same enzyme category (i.e., has the same EC number). Methods of determining whether an enzyme falls within a particular category are well known to the skilled person, who can determine the enzyme category without use of inventive skill. Suitable methods may, for example, be obtained from the International Union of Biochemistry and Molecular Biology.

Amino acid substitutions may be regarded as "conservative" where an amino acid is replaced with a different amino acid with broadly similar properties. Non-conservative substitutions are where amino acids are replaced with amino acids of a different type.

By "conservative substitution" is meant the substitution of an amino acid by another amino acid of the same class, in which the classes are defined as follows:

Class Amino Acid Examples

Nonpolar: A, V, L, I, P, M, F, W
Uncharged polar: G, S, T, C, Y, N, Q
Acidic: D, E
Basic: K, R, H.

Nicotinamide ribose compounds produced according to the present disclosure can be utilized in any of a variety of applications, for example, exploiting their biological or therapeutic properties (e.g., controlling low-density lipoprotein cholesterol, increasing high-density lipoprotein cholesterol, etc.). For example, according to the present disclosure, nicotinamide ribose may be used in pharmaceuticals, foodstuffs, and dietary supplements, etc.

The nicotinamide riboside produced by the method disclosed in this invention could have therapeutic value in improving plasma lipid profiles, preventing stroke, providing neuroprotection with chemotherapy treatment, treating fungal infections, preventing or reducing neurodegeneration, or in prolonging health and well-being. Thus, the present invention is further directed to the nicotinamide riboside compounds obtained from the genetically modified bacterial cell described above, for treating a disease or condition associated with the nicotinamide riboside kinase pathway of NAD+ biosynthesis by administering an effective amount of a nicotinamide riboside composition. Diseases or conditions which typically have altered levels of NAD+ or NAD+ precursors or could benefit from increased NAD+ biosynthesis by treatment with nicotinamide riboside include, but are not limited to, lipid disorders (e.g., dyslipidemia, hypercholesterolaemia or hyperlipidemia), stroke, neurodegenerative diseases (e.g., Alzheimer's, Parkinsons and Multiple Sclerosis), neurotoxicity as observed with chemotherapies, *Candida glabrata* infection, and the general health declines associated with aging. Such diseases and conditions can be prevented or treated by diet supplementation or providing a therapeutic treatment regime with a nicotinamide riboside composition.

It will be appreciated that, the nicotinamide riboside compounds isolated from the genetically modified bacteria of this invention can be reformulated into a final product. In some other embodiments of the disclosure, nicotinamide riboside compounds produced by manipulated host cells as described herein are incorporated into a final product (e.g., food or feed supplement, pharmaceutical, etc.) in the context of the host cell. For example, host cells may be lyophilized, freeze dried, frozen or otherwise inactivated, and then whole cells may be incorporated into or used as the final product. The host cell may also be processed prior to incorporation in the product to increase bioavailability (e.g., via lysis).

In some embodiments of the disclosure, the produced nicotinamide riboside compounds are incorporated into a component of food or feed (e.g., a food supplement). Types of food products into which nicotinamide riboside compounds can be incorporated according to the present disclosure are not particularly limited, and include beverages such as milk, water, soft drinks, energy drinks, teas, and juices; confections such as jellies and biscuits; fat-containing foods and beverages such as dairy products; processed food products such as rice, bread, breakfast cereals, or the like. In some embodiments, the produced nicotinamide riboside compounds is incorporated into a dietary supplement, such as, for example, a multivitamin.

The following examples are intended to illustrate the invention without limiting its scope in any way.

EXAMPLES

Example 1

Identification of Sequences Coding for NaMN Amidating Activity (NadE*)

Sorci and co-workers identified the enzyme FtNadE* encoded by the genome of *Francisella tularensis* (SEQ ID NO: 1) and demonstrated its ability to function both in vivo and in vitro as a nicotinamide mononucleotide (NaMN) amidating enzyme (Sorci L. e., 2009). In addition, they proposed that three amino acid residues were responsible for the enzyme's substrate preference for NaMN over NaAD: Y27; Q133; and 8236. In order to identify additional sequences encoding this function, 50 unique nucleotide sequences derived from a BLAST search of the NCBI nr/nt database on 14 Sep. 2016 using default parameters for tBlastn with the amino acid sequence for FtNadE (SEQ ID NO: 2) were translated and aligned using the Geneious alignment algorithm (Biomatters, LLLC.). 16 of these sequences had a conserved tyrosine, glutamine and arginine which aligned with Y27, Q133 and R236, respectively (i.e. contained a "Y-Q-R motif") and were predicted to encode NaMN amidating enzymes (SEQ ID NOs: 3 to 18 and FIG. 5).

Example 2

Genetic Constructs for Expression of NaMN Amidating Activity (NadE*) in *E. coli*

10 sequences encoding predicted nadE* open reading frames (SEQ ID NOs: 2 and 19 to 27) were selected based on maximizing phylogenetic distance (FIG. 6) among the set of 16 predicted nadE* genes and were codon optimized for expression in *E. coli* using the Geneious codon optimization algorithm with the *E. coli* K-12 codon usage table and threshold to be rare set at 0.4. The optimized sequences (SEQ ID NOs 28 to 37) were synthesized de novo by GenScript, Inc., and cloned into XhoI/NdeI digested pET24a (+) (Novagen, Inc.), also by GenScript, yielding the plasmids in Table 1. Plasmids were transformed into BL21 (DE3), allowing for IPTG induction of the nadE* genes in order to induce NR synthesis and yielding the strains ME407, ME644, ME645, ME646, ME647, ME648, ME649, ME650, ME651, ME652 (Table 2).

TABLE 1 plasmids used in this study

| plasmid | Description |
|---|---|
| pET24Ft | SEQ ID No. 37 (FtNadE*) cloned in pET24a(+) |
| pET24Dn | SEQ ID No. 29 (DnNadE*) cloned in pET24a(+) |
| pET24As | SEQ ID No. 30 (AsNadE*) cloned in pET24a(+) |
| pET24Fph | SEQ ID No. 31 (FphNadE*) cloned in pET24a(+) |
| pET24Fn | SEQ ID No. 32 (FnNadE*) cloned in pET24a(+) |
| pET24FspT | SEQ ID No. 33 (FspTNadE*) cloned in pET24a(+) |

TABLE 1-continued

| plasmids used in this study | |
|---|---|
| plasmid | Description |
| pET24FspF | SEQ ID No. 34 (FspFNadE*) cloned in pET24a(+) |
| pET24Fg | SEQ ID No. 35 (FgNadE*) cloned in pET24a(+) |
| pET24Fpe | SEQ ID No. 36 (FpeNadE*) cloned in pET24a(+) |
| pET24Mn | SEQ ID No. 28 (MnNadE*) cloned in pET24a(+) |
| pET24Ft-TGV | SEQ ID No. 42 (FtNadE*-TGV) cloned in pET24a(+) |
| pETMn-TGV | SEQ ID No. 43 (MnNadE*-TGV) cloned in pET24a(+) |
| pETFn-TGV | SEQ ID No. 44 (FnNadE*-TGV) cloned in pET24a(+) |
| pETFspT-TGV | SEQ ID No. 45 (FspTNadE*-TGV) cloned in pET24a(+) |
| pET-EcNadE | SEQ ID No. 46 (EcNadE) cloned in pET24a(+) |
| pBS-FnNadE | SEQ ID No. 38 cloned into pUC57 |
| pBS-FtNadE | SEQ ID No. 40 cloned into pUC57 |
| pBS-FspNadE | SEQ ID No. 41 cloned into pUC57 |
| pBS-MnNadE | SEQ ID No. 39 cloned into pUC57 |
| MB4124-FnNadE | SEQ ID No. 47 cloned into MB4124 |

TABLE 9

Figure 6:
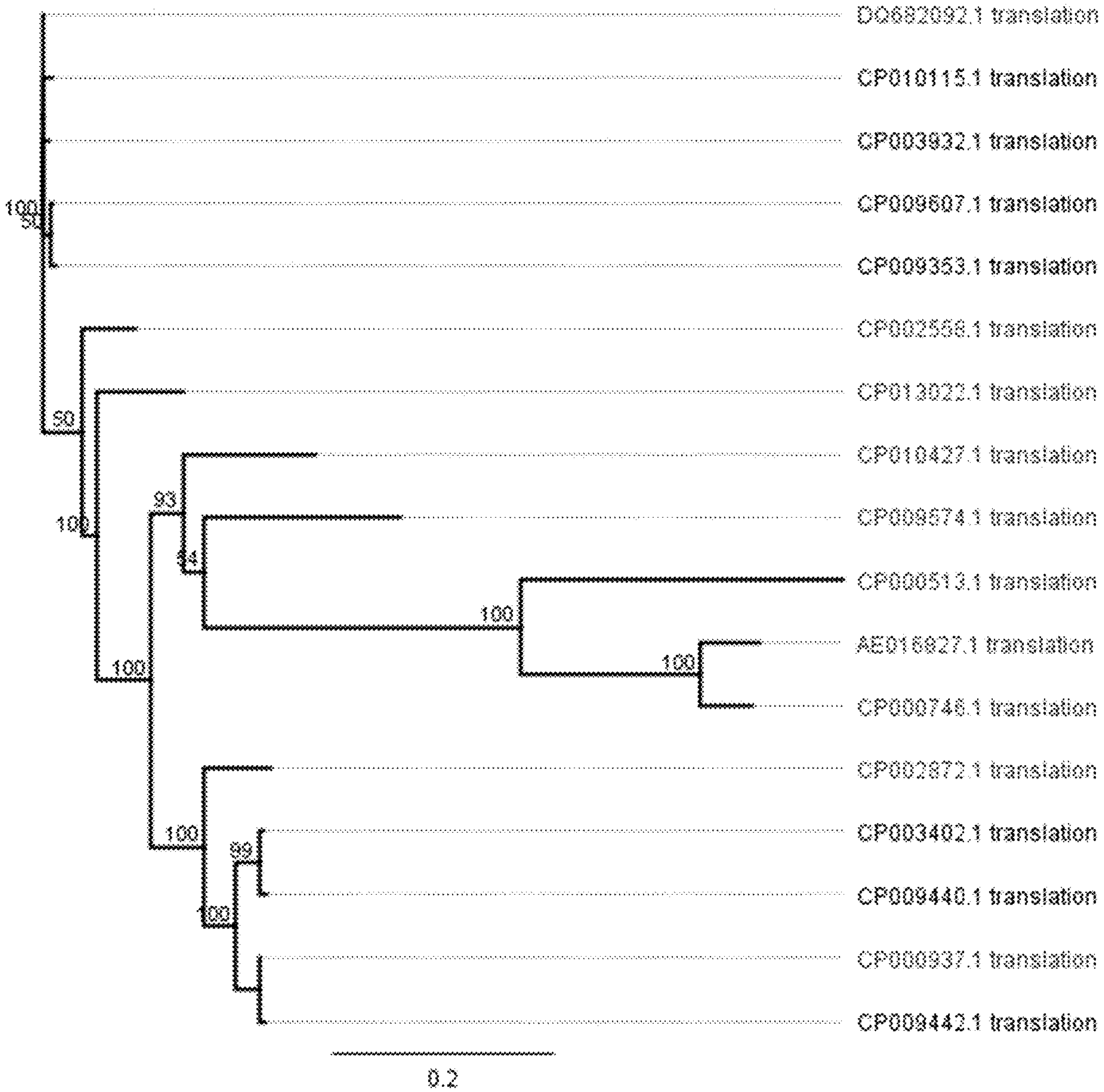
FIG. 6 shows neighbor-joining consensus tree of unique sequences with Y-Q-R motif.

| Look up table of sequences in FIG. 6 | |
|---|---|
| FIG. 6 Sequence Identifier | Seq ID No. |
| DQ682092.1 translation | 4 |
| CP010115.1 translation | 5 |
| CP003932.1 translation | 3 |
| CP009607.1 translation | 8 |
| CP009353.1 translation | 9 |
| CP002558.1 translation | 7 |
| CP013022.1 translation | 6 |
| CP010427.1 translation | 15 |
| CP009574.1 translation | 1 |
| CP000513.1 translation | 17 |
| AE016827.1 translation | 18 |
| CP000746.1 translation | 16 |
| CP002872.1 translation | 14 |
| CP003402.1 translation | 11 |
| CP009440.1 translation | 10 |
| CP000937.1 translation | 12 |
| CP009442.1 translation | 13 |

TABLE 2

| Strains used or described in this study | | |
|---|---|---|
| Strain | Species | Genotype |
| BL21(DE3) | *E. coli* | fhuA2 [lon] ompT gal (λ DE3) [dcm] ΔhsdS λ DE3 = λ sBamHIo ΔEcoRI-B int::(lacI::PlacUV5::T7 gene1) i21 Δnin5 |
| ME407 | *E. coli* | BL21(DE3) pET24Ft |
| ME409 | *E. coli* | BL21(DE3) |
| ME644 | *E. coli* | BL21(DE3) pET24Dn |
| ME645 | *E. coli* | BL21(DE3) pET24As |
| ME646 | *E. coli* | BL21(DE3) pETFph |
| ME647 | *E. coli* | BL21(DE3) pET24 Fn |
| ME648 | *E. coli* | BL21(DE3) pET24FspT |
| ME649 | *E. coli* | BL21(DE3) pET24FspF |
| ME650 | *E. coli* | BL21(DE3) pET24Fg |
| ME651 | *E. coli* | BL21(DE3) pET24Fpe |
| ME652 | *E. coli* | BL21(DE3) pET24Mn |
| ME708 | *E. coli* | BL21(DE3) pETFn-rev |
| ME710 | *E. coli* | BL21(DE3) pETFspT-rev |
| ME712 | *E. coli* | BL21(DE3) pET24Ft-rev |
| ME714 | *E. coli* | BL21(DE3) pETMn-rev |
| ME683 | *E. coli* | BL21(DE3) pETEcNadE |
| BS168 | *B. subtilis* | Wildtype strain |
| BS6209 | *B. subtilis* | BS168 nadR::spec |

TABLE 2-continued

| Strains used or described in this study | | |
|---|---|---|
| Strain | Species | Genotype |
| ME479 | *B. subtilis* | BS168 deoD::tet |
| ME492 | *B. subtilis* | BS168 pupG::neo |
| ME496 | *B. subtilis* | BS168 nadR::spec deoD::tet |
| ME517 | *B. subtilis* | BS168 nadR::spec deoD::tet pupG::neo |
| ME795 | *B. subtilis* | ME517 amyE::cat pVeg-MsNadE* |
| ME805 | *B. subtilis* | ME517 amyE::cat pVeg-rbs4-FnNadE* |
| ME820 | *B. subtilis* | ME517 amyE::cat pVeg-FspNadE* |
| ME824 | *B. subtilis* | ME517 amyE::cat pVeg-rbs4-FtNadE* |
| ATCC13032 | *C. glutamicum* | Wildtype strain |
| ME763 | *C. glutamicum* | ATCC13032 MB4124-FnNadE |

All basic molecular biology and DNA manipulation procedures described herein are generally performed according to Sambrook et al. or Ausubel et al. (J. Sambrook, E. F. Fritsch, T. Maniatis (eds). 1989. *Molecular Cloning: A Laboratory Manual*. Cold Spring Harbor Laboratory Press: New York; and F. M. Ausubel, R. Brent, R. E. Kingston, D. D. Moore, J. G. Seidman, J. A. Smith, K. Struhl (eds.). 1998. *Current Protocols in Molecular Biology*. Wiley: New York).

Example 3

Characterization of *E. coli* Strains Expressing NadE* Enzymes

To test the effect of NadE* expression on NR production, *E. coli* strains were inoculated from single colonies into LB medium and grown overnight (2 mL, 37° C., 15 mL test tube, 250 rpm, 50 ug/mL kanamycin). Precultures (200 μL) were used to inoculate 2 mL M9nC medium with or without 25 μM IPTG and grown in 24 well deep well plates (Whatman Uniplate, 10 mL, round bottom) sealed with an AirPore tape sheet (Qiagen) for three days (Infors Multitron Shaker, 800 rpm, 80% humidity). Samples were analyzed by LC-MS as described herein. Without plasmid, NR production was below the limit of quantification in the presence and absence of induction with 25 μM IPTG. Strains harboring plasmids for expression of NadE* enzymes produced up to 2.7 mg/L NR upon induction (Table 3).

TABLE 3

| Nicotinamide riboside concentratons (mg/L) in *E. coli* shake plate cultures upon IPTG induction (average of 2 cultures) | | | |
|---|---|---|---|
| Strain | Enzyme | No IPTG | 25 uM IPTG |
| ME407 | FtNadE* | <LOQ | 0.11 |
| ME409 | None | <LOQ | <LOQ |
| ME644 | DnNadE* | <LOQ | 0.28 |
| ME645 | AsNadE* | 0.08 | 0.31 |
| ME646 | FphNadE* | 0.02 | <LOQ |
| ME647 | FnNadE* | <LOQ | 1.91 |
| ME648 | FspTNadE* | 0.03 | 1.29 |
| ME649 | FspFNadE* | <LOQ | 0.82 |
| ME650 | FgNadE* | <LOQ | 0.64 |
| ME651 | FpeNadE* | 0.14 | 1.09 |
| ME652 | MnNadE* | 0.1 | 2.73 |

Example 4

Increased NR Production in *E. coli* Requires a NadE* with Y27, Q133 and R236

To demonstrate the importance of the YQR motif for NR production, four of the *E. coli* optimized NadE* sequences were altered to remove the residues which aligned to the *Francisella tularensis* Y27, Q133, R236 residues and replaced with the amino acid resides coded for in the *Bacillus anthracis* NadE (T, G, & V, respectively; SEQ ID NOs: 42 to 45). Site directed mutagenesis of the corresponding pET24a(+) plasmids was performed by GenScript, Inc, resulting in the plasmids in Table 1. Plasmids were transformed into BL21(DE3), allowing for IPTG induction of the nadE-TGV genes and yielding the strains, ME708, ME710, ME712, and ME714 (Table 2). These strains with a NadE-TGV failed to exhibit similar IPTG dependent increases in NR production to strains with NadE* (Table 4).

TABLE 4

Nicotinamide riboside concentrations (mg/L) in *E. coli* shake plate cultures upon IPTG induction

| Strain | enzyme | No IPTG | 50 uM IPTG |
|---|---|---|---|
| BL21(DE3) | none | <LOQ | <LOQ |
| BL21(DE3) | none | <LOQ | <LOQ |
| ME683 | EcNadE | <LOQ | <LOQ |
| ME683 | EcNadE | <LOQ | 0.01 |
| ME647 | FnNadE* | 0.04 | 0.92 |
| ME647 | FnNadE* | 0.02 | 0.75 |
| ME708 | FnNadE-TGV | <LOQ | 0.05 |
| ME708 | FnNadE-TGV | <LOQ | 0.07 |
| ME648 | FspTNadE* | <LOQ | 0.09 |
| ME648 | FspTNadE* | <LOQ | 0.16 |
| ME710 | FspTNadE-TGV | 0.01 | 0.01 |
| ME710 | FspTNadE-TGV | 0.02 | 0.01 |
| ME407 | FtNadE* | <LOQ | 0.1 |
| ME407 | FtNadE* | 0.02 | 0.12 |
| ME714 | FtNadE-TGV | 0.01 | <LOQ |
| ME714 | FtNadE-TGV | <LOQ | <LOQ |
| ME652 | MsNadE* | 0.07 | 1.11 |
| ME652 | MsNadE* | <LOQ | 0.96 |
| ME712 | MsNadE-TGV | <LOQ | 0.1 |
| ME712 | MsNadE-TGV | <LOQ | <LOQ |

Example 5

Overexpression of *E. coli* NadE is not Sufficient to Observe Increased NR Production To demonstrate that high levels of NaAD amidating activity (NadE) are insufficient to produce increased NR accumulation, the wildtype nadE open reading (SEQ ID NO: 46) frame was amplified via PCR from the genome of BL21(DE3) with primers MO11159 and MO11160 (Table 5) that added XhoI/NdeI restriction sites at the start and stop codons respectively. The PCR fragment was ligated into similarly digested pET24a(+), yielding plasmid pET24b+ $nadE_{BL21}$. This plasmid was transformed into BL21(DE3), allowing for IPTG induction of nadE and yielding the strain ME683. When tested for NR production alongside strains expressing NadE* sequences, this strain with additional expression of the *E. coli* NadE failed to exhibit IPTG dependent increases in NR concentration. (Table 4).

TABLE 5

Primers used in strain construction

| Primer | Name | Sequence (5'-3') | Use |
|---|---|---|---|
| 10444 | pDG1662_Pveg-I_pdxP Copy extraction (rev) | CGGTAAGTCCCGTCTAGCCT | Amplification of all 3' flanks |
| 10447 | amyE::nadEstar 5' (reversed) (fwd) | ATGTTTGCAAAACGATTCAAAACCT | Amplification of all 5' flanks |
| 11222 | amyE-FnNadE 3' for | TTACACCGAATTTCTAATAATAACCGGGCAGGCCATG | |
| 11223 | amyE-FnNadE 3' rev | GGCCTGCCCGGTTATTATTAGAAATTCGGTGTAAGAG | |
| 11226 | amyE-FspNadE 3' for | CTTTTACACCGAATTTTTAATAATAACCGGGCAGGCCATG | |
| 11227 | amyE-FspNadE 3' rev | GGCCTGCCCGGTTATTATTAAAAATTCGGTGTAAAAG | |
| 11230 | amyE-MsNadE 3' for | CGGATGAAGCGGAATGTTAATAATAACCGGGCAGGCCATG | |
| 11231 | amyE-MsNadE 3' rev | GGCCTGCCCGGTTATTATTAACATTCCGCTTCATCCG | Amplification of MsNadE gBlock |
| 11232 | PvegI MsNadE 5' amyE for | GAAAGGTGGTGAACTACTATGAAAACAGCAGCATACGC | Amplification of MsNadE gBlock |
| 11233 | PvegI MsNadE 5' amyE rev | GCGTATGCTGCTGTTTTCATAGTAGTTCACCACCTTTCTC | Amplification of MsNadE 5' flank |
| 11234 | amyE-FtNadE 3' for | CACTTACACCGAACTTCTAATAATAACCGGGCAGGCCATG | |
| 11235 | amyE-FtNadE 3' rev | GGCCTGCCCGGTTATTATTAGAAGTTCGGTGTAAGTG | |
| 11341 | rbs4 FnNadE rev | AAGGGAGGTTTCATATGAAAATTGTTAAAGATT | |
| 11342 | rbs4 FnNadE For | TTTAACAATTTTCATATGAAACCTCCCTTAATTCTCG | |
| 11351 | pVegI-FspNadE Rev | GTGAACTACTATGAAAATTGTAAAAAACTTTATTG | |
| 11352 | pVegI-FspNadE For | TTACAATTTTCATAGTAGTTCACCACCTTTCTCTA | |

TABLE 5-continued

| Primers used in strain construction | | | |
|---|---|---|---|
| Primer | Name | Sequence (5'-3') | Use |
| 11353 | rbs4 FtNadE rev | AAGGGAGGTTTCATATGAAAATCGT TAAAGACTTC | |
| 11354 | rbs4 FtNadE For | TAACGATTTTCATATGAAACCTCCC TTAATTCTCG | |
| 11159 | XhoI-3' NadE BL21 | GCTACTTACTCTCGAGTTACTTTTT CCAGAAATCAT | Amplification of EcNadE |
| 11160 | NdeI 5'-NadE-BL21 | GCTAACTTAGCATATGATGACATTG CAACAACA | Amplification of EcNadE |

Example 6

Construction of *B. subtilis* Strains with Increased Basal Levels of NR Accumulation In order to demonstrate efficacy of NadE* enzymes in promoting NR accumulation in a context of higher product accumulation, a host strain was engineered for increased basal levels of NR accumulation. *E. coli* strain DH5a, *Corynebacterium glutamicum* strain ATCC 13032 and *B. subtilis* strain 168 were grown overnight in rich media (LB for *E. coli*, BHI for *C. glutamiucm* and *B. subtilis*) and inoculated 1:10 into 2 mL M9nC medium. After 24 hours, cultures were sampled for MS and relative NR levels were examined. *B. subtilis* NR production was higher than *E. coli* or *C. glutamiucm* and was chosen as the host for further engineering.

Cassettes for the precise deletion of nadR, deoD, and pupG were constructed by long flanking PCR (LF-PCR). Flanking regions for each gene were obtained by amplification of BS168 genomic DNA (Roche High Pure PCR template preparation kit) with primers in Table 5, which were designed such that sequences homologous to the 5' or 3' region of the appropriate antibiotic resistance gene (spectinomycin, tetracycline, and neomycin, respectively, SEQ ID NOs: 48 to 50) were incorporated into the PCR product (Phusion Hot Start Flex DNA Polymerase, 200 nM each primer, initial denaturation 2 min @ 95 C, 30 cycles of: 30 sec @ 95 C; 20 sec @ 50 C; 60 sec @ 72 C, final hold 7 min at 72 C). Antibiotic resistance genes were similarly amplified with primers to incorporate sequences homologous to the 5' and 3' flanking regions. PCR products were gel purified and used for LF-PCR with appropriate primers (Table 5) (Phusion Hot Start Flex DNA Polymerase, 200 nM each primer, 150 ng each PCR product, initial denaturation 30 sec @ 98 C, 35 cycles of: 30 sec @ 98 C; 30 sec @ 55 C; 360 sec @ 72 C). LF-PCR product was purified and used for transformation of *B. subtilis* strains.

BS168 was transformed with LF-PCR product via natural transformation ("Molecular Biological Methods for *Bacillus*". 1990. Edited by C. R Harwood and S. M. Cutting. John Wiley and Sons) yielding BS6209 (nadR::spe), ME479 (deoD::tet), and ME492 (pupG::neo). Genomic DNA (prepared as above) from ME492 was used to transform BS6209, yielding ME496 (nadR::spe pupG::neo). Genomic DNA (prepared as above) from ME479 was used to transform ME496, yielding ME517 (nadR::spe pupG::neo deoD::tet).

Example 7

Construction and Characterization of *B. subtilis* Strains Expressing NadE*

4 sequences encoding NadE* activity were codon optimized for expression in *B. subtilis* (Geneious codon optimization algorithm *B. subtilis* 168 codon usage table, threshold to be rare set at 0.4) and optimized sequences (SEQ ID NOs: 38-41) were synthesized as gBlocks by IDT. Cassettes for the expression of optimized NadE* sequences were generated by LF-PCR. A flanking region containing amyE 5' region, cat (chloramphenicol resistance), pVegI promoter and a flanking region containing the amyE 3' region, were amplified as above using appropriate primers (Table 5) and pDG1662 (*Bacillus* Genetic Stock Center) and gBlocks as templates. Gel purified flanking regions and gBlocks (above) were used for LF-PCR as above, and products were gel purified.

ME517 was transformed as above with the purified DNA and a transformant was colony purified, yielding strains ME795 (MsNadE*), ME805 (FnNadE*), ME820 (FspNadE*) and ME824 (FtNadE*). Strains were used to inoculate duplicate 1 mL cultures of BHI medium, and ME517 was inoculated in quadruplicate, in a 24 well shake plate and incubated at 37 C overnight (as above). After 17 hours, plate was centrifuged, supernatant discarded and pellet was resuspended in 2 mL M9nC medium. Plates were placed back in incubator and grown a further 24 hours. NR was measured and strains harboring NadE* overexpression constructs produced on average between 72 and 133% more NR than the parent strain (Table 6).

TABLE 6

Nicotniamide riboside concentrations in *B. subtilis* shake plate cultures.

| Strain | Enzyme | NR (mg/L) |
|---|---|---|
| ME517 | none | 53.2 |
| ME517 | none | 42.2 |
| ME517 | none | 38.8 |
| ME517 | none | 37.6 |
| ME795 | MsNadE* | 72.3 |
| ME795 | MsNadE* | 75.5 |
| ME814 | FnNadE* | 102.9 |
| ME814 | FnNadE* | 98.0 |
| ME820 | FspNadE* | 99.1 |
| ME820 | FspNadE* | 94.8 |
| ME824 | FtNadE* | 76.8 |
| ME824 | FtNadE* | 79.9 |

Example 8

Construction and Characterization of a *Corynebacterium glutamicum* Strain Expressing NadE*

In order to further demonstrate the general utility of these sequences for production of NR in bacteria, the sequence encoding FnNadE* was codon optimized for expression in *C. glutamicum* (Geneious codon optimization algorithm *C. glutamicum* codon usage table, threshold to be rare set at 0.4) and the optimized sequence (SEQ ID NO: 47) was synthesized as a gBlock by IDT with additional sequence upstream of the open reading frame encoding an EcoRI restriction site and *Corynebacterium glutamicum* consensus RBS and additional sequence downstream encoding a SmaI restriction site. The gBlock was digested with EcoRI/SmaI, yielding a 760 bp fragment which was ligated into similarly digested MB4124 yielding the plasmid MB4124-FnNadE*. MB4124 was derived from the cryptic *C. glutamicum* low-copy pBL1 plasmid (see Santamaria et al. J. Gen. Microbiol, 130:2237-2246, 1984) by combining MB4094 (described in U.S. patent application 60/692,037) with an IPTG inducible promoter from pTrc99a (Gene. 1988 Sep. 30; 69(2):301-15). *C. glutamicum* strain ATCC 13032 was transformed (Follettie, M. T et al. J. Bacteriol. 167:695-702, 1993) with plasmid for IPTG inducible expression of FnNadE*.

Single colonies were inoculated to 2 mL VY medium (+50 μg/mL kanamycin as appropriate) and grown at 30 C overnight. 200 μL of this culture was used to inoculate 2 mL of AZ medium with 2% glucose (+10 μg/mL kanamycin where appropriate) and with varying levels of IPTG. NR was measured and strains harboring FnNadE* overexpression constructs displayed an IPTG dependent increase in NR production (Table 7).

TABLE 7

Nicotinamide riboside concentrations (mg/L) in *Corynebacterium glutamicum* shake plate cultures upon IPTG induction of FnNadE*

| Strain | 0 mM IPTG | 0.25 mM IPTG |
|---|---|---|
| ATCC13032 | 0.02 | 0.03 |
| ME763 | 0.03 | 0.16 |
| ME763 | 0.01 | 0.11 |

Example 9

Detection of Nicotinamide Riboside in Production Cultures

NR was analyzed by liquid chromatography/mass spectrometry (LCMS). After cultivation, 100 μL was diluted in 900 μL MS diluent (10% Water 10 mM Ammonium Acetate pH9.0, 90% acetonitrile) in 96 well deep well plates. Plates were centrifuged (10 min, 3000 rpm) and supernatant was transferred to a new plate for characterization. Supernatant was injected in 5 IA portions onto a HILIC UPLC column (Waters BEH Amide, 2.1×75 mm P/N 1860005657). Compounds were eluted at a flow rate of 400 uL $min^{-1}$, after a 1 minute hold, using a linear gradient from 99.9% (10 mM ammonium acetate at pH 9.0 with 95% acetonitrile/5% Water) mobile phase D, to 70% (10 mM ammonium acetate pH 9.0 50/50 Acetonitrile/Water) mobile phase C, over 12 minutes, followed by a 1 minute hold in mobile phase C, and 5 minutes re-equilibration in mobile phase D (Table 8). Eluting compounds were detected with a triple quadropole mass spectrometer using positive electrospray ionization. The instrument was operated in MRM mode and NR was detected using the transition m/z 123>80. NR was quantified by comparison to standard (Chromadex) injected under the identical condition.

TABLE 8

Gradient program for LCMS quantification of NR

| Time | Flow (mL/min.) | % A | % B | % C | % D | Curve |
|---|---|---|---|---|---|---|
| initial | 0.400 | −0.0 | 0.0 | 0.1 | 99.9 | initial |
| 1.00 | 0.400 | −0.0 | 0.0 | 0.1 | 99.9 | 6 |
| 12.00 | 0.400 | 0.0 | 0.0 | 70.0 | 30.0 | 6 |
| 13.00 | 0.400 | 0.0 | 0.0 | 70.0 | 30.0 | 6 |
| 13.1 | 0.400 | −0.0 | 0.0 | 0.1 | 99.9 | 6 |
| 18.00 | 0.400 | −0.0 | 0.0 | 0.1 | 99.9 | 6 |

Example 10

Media Used for Bacterial Growth and Production Assays 1 liter of VY medium contains 25 g veal infusion broth (Difco), 5 g Bacto yeast extract (Difco)

1 liter of M9nC medium contains 50 g glucose, 6 g $Na_2HPO_4$, 3 g $KH_2PO_4$, 0.5 g NaCl, 1 g $NH_4Cl$, 2 mM $MgSO_4$, 15 mg $Na_2EDTA$, 4.5 mg $ZnSO_4$*7 $H_2O$, 0.3 mg $CoCl_2$*6 $H_2O$, 1 mg $MnCl_2$*4 $H_2O$, 4.5 mg $CaCl_2$*2 $H_2O$, 0.4 mg $Na_2MoO_4$*2 $H_2O$, 1 mg $H_3BO_3$, and 0.1 mg KI.

1 liter of AZ medium contains 20 g glucose, 2 g NaCl, 3 g Na-Citrate, 0.1 g $CaCl_2$*2 $H_2O$, 4 g $K_2HPO_4$, 2 g $KH_2PO_4$, 7.5 g $NH_4SO_4$, 3.75 g urea, 0.5 g $MgSO_4$*7 $H_2O$, 450 μg thiamine, 450 μg biotin, 4 mg pantothenate, 15 mg $Na_2EDTA$, 4.5 mg $ZnSO_4$*7 $H_2O$, 0.3 mg $CoCl_2$*6 $H_2O$, 1 mg $MnCl_2$*4 $H_2O$, 4.5 mg $CaCl_2$*2 $H_2O$, 0.4 mg $Na_2MoO_4$*2 $H_2O$, 1 mg $H_3BO_3$, and 0.1 mg KI.

What is claimed is:

1. A method for producing nicotinamide riboside (NR), comprising culturing a bacterium cell in a medium under conditions effective to produce NR and recovering NR from the medium and thereby producing NR, wherein the bacterium cell comprises the modification of adding the activity of a heterologous nicotinic acid amidating protein (NadE*) and further comprises at least one modification selected from the group consisting of:

a) adding or increasing the activity of a nicotinamide adenine dinucleotide (NAD+) hydrolyzing protein;

b) blocking or reducing the activity of a protein which functions to repress NAD+ biosynthesis by repressing transcription of nadA, nadB, nadC genes or combinations thereof;

c) blocking or reducing the activity of a protein which functions as a nicotinamide riboside transporter protein;

d) blocking or reducing the activity of a protein which functions as a nicotinic acid mononucleotide adenyltransferase;

e) blocking or reducing the activity of a protein which functions as a nicotinamide mononucleotide amidohydrolase;

f) blocking or reducing the activity of a protein which functions as a purine nucleoside phosphorylase;

g) adding or increasing the activity of a protein which functions as a nicotinamide mononucleotide hydrolase; and h) adding or increasing the activity of a protein which functions as a L-aspartate oxidase, a quinolate synthase, a quinolate phosphoribosyltransferase, or combinations thereof.

2. A method for producing nicotinamide riboside (NR), comprising culturing a bacterium cell in a medium under conditions effective to produce NR and recovering NR from the medium and thereby producing NR, wherein the bacterium cell comprises the modification of adding the activity of a heterologous nicotinic acid amidating protein (NadE*) and the modification of:

adding or increasing the activity of a nicotinamide adenine dinucleotide (NAD+) hydrolyzing protein.

3. The method of claim 2, wherein the bacterium cell further comprises at least one modification selected from the group consisting of:

a) blocking or reducing the activity of a protein which functions to repress NAD+ biosynthesis by repressing transcription of nadA, nadB, nadC genes or combinations thereof;

b) blocking or reducing the activity of a protein which functions as a nicotinamide riboside transporter protein;

c) blocking or reducing the activity of a protein which functions as a nicotinic acid mononucleotide adenyltransferase;

d) blocking or reducing the activity of a protein which functions as a nicotinamide mononucleotide amidohydrolase;

e) blocking or reducing the activity of a protein with function which functions as a purine nucleoside phosphorylase;

f) adding or increasing the activity of a protein which functions as a nicotinamide mononucleotide hydrolase; and g) adding or increasing the activity of a protein which functions as a L-aspartate oxidase, a quinolate synthase, a quinolate phosphoribosyltransferase, or combinations thereof.

* * * * *